US008834877B2

(12) United States Patent
O'Shannessy

(10) Patent No.: US 8,834,877 B2
(45) Date of Patent: Sep. 16, 2014

(54) ANTI-FOLATE RECEPTOR ALPHA ANTIBODIES AND USES THEREOF

(71) Applicant: Eisai R&D Management Co., Ltd., Tokyo (JP)

(72) Inventor: Daniel John O'Shannessy, Schwenksville, PA (US)

(73) Assignee: Eisai R&D Managment Co., Ltd., Tokyo (JP)

( * ) Notice: Subject to any disclaimer, the term of this patent is extended or adjusted under 35 U.S.C. 154(b) by 0 days.

(21) Appl. No.: 13/800,575

(22) Filed: Mar. 13, 2013

(65) Prior Publication Data

US 2013/0183299 A1 Jul. 18, 2013

Related U.S. Application Data

(62) Division of application No. 13/548,775, filed on Jul. 13, 2012, now Pat. No. 8,475,795.

(60) Provisional application No. 61/604,954, filed on Feb. 29, 2012, provisional application No. 61/604,412, filed on Feb. 28, 2012, provisional application No. 61/508,444, filed on Jul. 15, 2011.

(51) Int. Cl.
*C07K 16/28* (2006.01)
*G01N 33/574* (2006.01)
*G01N 33/82* (2006.01)

(52) U.S. Cl.
CPC ............ *C07K 16/28* (2013.01); *G01N 2800/56* (2013.01); *G01N 33/57419* (2013.01); *G01N 2800/52* (2013.01); *G01N 33/82* (2013.01); *G01N 33/57449* (2013.01); *G01N 33/57407* (2013.01); *G01N 33/57415* (2013.01); *C07K 2317/92* (2013.01); *G01N 33/57442* (2013.01); *C07K 2317/34* (2013.01); *G01N 33/57484* (2013.01); *G01N 33/57423* (2013.01)
USPC ..................................... 424/133.1; 435/320.1

(58) Field of Classification Search
None
See application file for complete search history.

(56) References Cited

U.S. PATENT DOCUMENTS

| 6,348,195 | B1 | 2/2002 | Wallace et al. |
| 6,770,445 | B1 | 8/2004 | Scholler et al. |
| 7,270,960 | B2 | 9/2007 | Hellstrom et al. |
| 7,754,698 | B2 | 7/2010 | Freier |
| 2004/0235108 | A1 | 11/2004 | Grasso et al. |
| 2005/0232919 | A1 | 10/2005 | Grasso et al. |
| 2006/0239910 | A1 | 10/2006 | Nicolaides et al. |
| 2008/0131366 | A1 | 6/2008 | Ratnam |
| 2009/0081710 | A1 | 3/2009 | Low et al. |
| 2010/0055034 | A1 | 3/2010 | Martin et al. |
| 2011/0177525 | A1 | 7/2011 | Shuber et al. |
| 2012/0207771 | A1 | 8/2012 | O'Shannessy |

FOREIGN PATENT DOCUMENTS

| WO | WO 2004/082463 | A2 | 9/2004 |
| WO | WO 2006/105141 | A1 | 10/2006 |
| WO | WO 2006/116592 | A2 | 11/2006 |
| WO | WO 2008/031577 | A1 | 3/2008 |
| WO | WO 2009/132081 | | 10/2009 |
| WO | WO 2009/132081 | A2 | 10/2009 |

OTHER PUBLICATIONS

Alberti, et al., "The CA-MOv18 Molecule, a Cell-Surface Marker of Human Ovarian Carcinomas, is Anchored to the Cell Membrane by Phosphatidylinositol," Biochemical and Biophysical Research Communications, 171, 1990, (3):1051-1055.
Armstrong, et al., "Exploratory phase II efficacy study of MORAb-003,a monoclonal antibody against folate receptor alpha, in platinum-sensitive ovarian cancer in first relapse," 2008,*J Clin. Oncology, ASCO Annual Meeting Proceedings*,26, No. 15S, 5500.
Basal et al, "Functional Folate Receptor Alpha Is Elevated in the Blood of Ovarian Cancer Patients" PloS one, Jul. 2009, 4(7), e6292.
Belloni, Carlo, et al., "MOv18 Monoclonal Antibody in Diagnostic Applications: Capability to Recognize the Histotype of the Original Tumor," Feb. 1990, Tumori 76:10-13.
Bottero, Federica, et al,. "Gene Transfection and Expression of the Ovarian Carcinoma Marker Folate Binding Protein NIH/3T3 Cells Increases Cell Growth in Vitro and in Vivo," Cancer Research, Dec. 1993, 53:5791-5796.
Brawer et al., "Measurement of complexed PSA improves specificity for early detection of prostate cancer", Sep. 1998, Urology, 52, p. 372-378.
Budman et al., "Biomarkers for detection and surveillance of bladder cancer", Jun. 2008, CUAJ, 2(3), p. 212-221.
Bueno et al, "The A Folate Receptor Is Highly Activated in Malignant Pleural Mesothelioma" The Journal of thoraicic and Cardiovascular Surgery, Feb. 2001, 121(2), 225-233.
BIOcare Medical, Folate Receptor Alpha IHC Assay Kit, Prediluted Monoclonal Antibody with HRP Detection Kit, Control No. 901-BR14006K-112111, Biocare Medical, LLC, Concord, CA, 94520, 2012, Mar. 20, 2012, pp. 4, www.biocare.net.
BIOcare Medical, Folate Receptor Alpha IHC Assay Kit, Prediluted Monoclonal Antibody with HRP Detection Kit, Control No. 901-BR14006K-030612, Biocare Medical, LLC, Concord, CA, 94520, 2012, Mar. 20, 2012, pp. 4, www.biocare.net.

(Continued)

*Primary Examiner* — Brian J Gangle
*Assistant Examiner* — Andrea McCollum
(74) *Attorney, Agent, or Firm* — Baker Hostetler LLP

(57) ABSTRACT

Described herein are antibodies, and antigen-binding fragments thereof, that are specific for folate receptor alpha, related polynucleotides, expression vectors, and cells that express the described antibodies. Also provided are methods of using the described antibodies, and antigen-binding fragments thereof, and related kits. Provided herein are also methods for diagnosing cancers, such as breast cancer, thyroid cancer, colorectal cancer, endometrial cancer, fallopian tube cancer, ovarian cancer, or lung cancer, using the described antibodies, and antigen-binding fragments thereof. The methods involve determining the amount of folate receptor alpha in a sample derived from a subject and comparing this level with the level of folate receptor alpha in a control sample or reference sample.

13 Claims, 21 Drawing Sheets

(56) References Cited

OTHER PUBLICATIONS

Campbell, Ian G., et al., "Folate-binding Protein Is a Marker for Ovarian Cancer," *Cancer Research*, Oct. 1991, 51:5329-5338.
Colman et al., "Effects of amino acid sequence changes on antibody-antigen interactions", Jan. 1994, Research in Immunology, 145, p. 33-36.
Coney L et al, "Chimeric murine-human antibodies directed against folate binding receptor are efficient mediators of ovarian carcinoma cell killing", Cancer Research, American Association for Cancer Research, Jan. 1, 1994, 54(9), p. 2450.
Cuijpers, Vincent M. J. l., et al., "Immunocytochemical Detection of Ovarian Carcinoma Cells in Serous Effusions," Acta cytologica, May-Jun. 1993, 37(3):272-279.
Dolo, Vincenza, et al., "Matrix-degrading proteinases are shed in membrane vesicles by ovarian cancer cells in vivo and in vitro," *Clinical & Experimental Metastasis*, Mar. 1999, 17:131-140.
Forster, Martin D., et al., "Flow Cytometric Method for Determining Folate Receptor Expression Ovarian Carcinoma Cells," Nov. 2007, *Cytometry Part A*, 71A:945-950.
Gadina, Massimo, et al., "Preclinical Pharmacokinetics and Localization Studies of the Radioiodinated Anti-Ovarian Carcinoma Mab MOv18," *Nuclear Medicine Biology*, 1991,18(4):403-408.
Harris et al., "Assessing genetic heterogeneity in production cell lines: Detection by peptide mapping of a low level Tyr to Gln sequence variant in a recombinant antibody", Nov. 1993, Biotechnology, 11, p. 1293-1297.
Henne, Walter A., et al., "Detection of Folate Binding Protein with Enhanced Sensitivity Using a Functionalized Quartz Crystal Microbalance Sensor," *Anal. Chem.* Jul. 2006, 78:4880-4884.
International Search Report for Application No. PCT/US2011/059411, dated May 21, 2012.
Ke, Chun-Yen, et al., "The Folate Receptor as a Molecular Target for Tumor-Selective Radionuclide Delivery," *Nuclear Medicine and Biology*, Nov. 2003, 30:811-817.
Kelemen, Linda E., et al., "The role of folate receptor a in cancer development, progression and treatment: Cause, consequence or innocent bystander?," *Int. J Cancer*, Jul. 2006, 119:243-250.
Kumar et al., "Protein Stiffening and Entropic Stabilization in the Subdenaturing Limit of Guanidine Hydrochloride", Oct. 2004, Biophysical Journal, 87, p. 2656-2662.
Low, Philip S., et al., "Discovery and Development of Folic-Acid-Based Receptor Targeting for Imaging and Therapy of Cancer and Inflammatory Diseases," *Accounts of Chemical Research*, Jan. 2008, 4 1(1 ): 120-129.
Ludwig et al., Biomarkers in cancer staging, prognosis and treatment selection, Nov. 2005, Nature Reviews: Cancer, vol. 5, p. 845-856.
Iwakiri, Shotaro, et al., "Expression Status of Folate Receptor a Is Significantly Correlated with Prognosis in Non-Small-Cell Lung Cancers," *Annals of Surgical Oncology*, Mar. 2008,15(3):889-899.
Mettlin et al., "Relative sensitivity and specificity of serum prostate specific antigen (PSA) level compared with age-referenced PSA, PSAdensity, and PSAchange", Sep. 1994, Cancer, 74 (5), p. 1615-1620.
Miotti et al., Characterization of human ovarian carcinoma-associated antigens defintged by novel monoclonal antibodies with tumor-restricted specificity, 1987, International Journal of Cancer, 39, p. 297-303.
Mottolese, Marcella, et al., "The Use of a Panel of Monoclonal Antibodies Can Lower False-C7 Negative Diagnoses of Peritoneal Washings in Ovarian Tumors," Cancer, 68:1803-1807, Oct. 1991.
Rudikoff et al., "Single amino acid substitution altering antigen-binding specificity, Mar. 1982, Proceedings of the National Academy of Science", U.S.A., 79, p. 1979-1983.
Smith-Jones, Peter M., et al., "Preclinical radioimmunotargeting of folate receptor alpha using the monoclonal antibody conjugate DOTA-MORAb-003," *Nuclear Medicine and Biology*, Apr. 2008, 35:343-351.

Smith et al,"A novel monoclonal antibody for detection of folate receptor alpha in paraffin-embedded tissues", Hybridoma, Oct. 2007, 26(5), 281-288.
Sudimack, Jennifer, et al., "Targeted Drug Delivery Via the Folate Receptor," *Advanced Drug Delivery Reviews*, Mar. 2000, 41:147-162.
Tran, et al. "Enhancement of Folate Receptor A Expression in Tumor CellsThrough the Glucocorticoid Receptor: A Promising Means to ImprovedTumor Detections and TarQetinQ," Cancer Res, May 2005, 65(10):4431-4441.
Konner e t a l , "Farletuzumab, a humanized monoclonal antibody against folate ovarian receptor alpha, in epithelial cancer: a phase I study", Clinical Cancer Research, The American Association for Cancer Research, Nov. 1, 2010, 16(21), 5288-5295.
Cline, "Perspectives for gene therapy: inserting new genetic information into mammalian cells by physical techniques and viral vectors", Pharmacology & Therapeutics, 1985, 29(1), 69-92.
Davis e t a l , I . Antibody-independent ApoStream technology isolates folate receptor alpha (FRA)-positive circulating tumor cells from blood of non-small cell lung adenocarcinoma patients, Journal of Clinical Oncology, 30, Suppl. Abstract e21028, May 20, 2012, ASCO Annual Meeting, p. 2.
Ebel e t a l , "Preclinical evaluation of MORAb-003, a humanized monoclonal antibody antagonizing folate receptor-alpha", Cancer Immunity, Mar. 9, 2007, 7(6), 1-8.
Elnakat, Hala and Manohar, Ratnam, "Role of folate receptor genes in reproduction and related cancers" Frontiers in Bioscience, Jan. 1, 2006, 11, 506-519.
Franklin, Wa et al, New anti-lung-cancer antibody cluster 12 reacts with human folate receptors present on adenocarcinoma, INT J. Cancer, 1994, Suppl 8,89-95.
Gadi et al, In vivo sensitization of ovarian tumors to chemotherapy by expression of *E. coli* purine nucleoside phosphorylase in a small fraction of cells, Oct. 2000, Gene Therapy, 7(20), 1738-1743.
Hartmann et al, "Folate receptor overexpression is associated with poor outcome in breast cancer" International Journal of Cancer, Sep. 2007, 121(5), 938-942.
Holme et al, "A Folate Binding Protein in Ascitic Fluid, Serum and Ovarian Tissue of Patients with Ovarian Adenocarcinoma Immunoreacts with Antibodies Against Human Milk Folate Binding Protein", Bioscience reports, Apr. 1998, 18(2), 49-57.
IntelliPATH, Folate Receptor Alpha IHC Assay Kit, Prediluted Monoclonal Antibody with HRP Detection Kit, Biocare Medical, LLC, Concord, CA, 94520, 2012, Mar. 20, 2012, pp. 4, www.biocare.net.
Iwakiri Setal, "Expression status of folate receptor alpha is significantly correlated with prognosis in non-small-cell lung cancers" Annals of Surgical Oncology, 2008, 15(3),889-899.
Mantovani e t a l , "Folate Binding Protein Distribution in Normal Tissues and Biological Fluids From Ovarian Carcinoma Patients as Detected by the Monoclonal Antibodies MOv18 and MOv19", European Journal of Cancer, 1994, 30A(3), 363-369.
Okayama and Berg, "A eDNA Cloning Vector That Permits Expression of eDNA Inserts in Mammalian Cells", Molecular and Cellular Biology, Feb. 1983, 3(2), 280-289.
Biocare Press Release Mar. 20, 2012, "Biocare Medical Launches Key Diagnostic Kit to Identify Folate Receptor Alpha Expression", http://biocare.net/news/biocare-medical-launches-key-diagnostic-kit-to-identify-folate-receptor-alpha-expression.
Fisher, "Exploratory Study of 99mTc-EC20 Imaging for Identifying Patients with Folate Receptor-Positive Solid Tumors" The Journal of Nuclear Medicine, Jun. 2008, 49(6), 899-906.
International Patent Application No. PCT/US2012/046672: International Search Report and Written Opinion datred Oct. 2, 2012, 16 pages.
O'Shannessy et al, "Characterization of the Human Folate Receptor Alpha Via Novel Antibody-Based Probes" Oncotarget, Dec. 2011, 2(12), 1227-1243.
O'shannessy et al, "Folate Receptor Alpha Expression in Lung Cancer: Diagnostic and Prognostic Significance", Oncotarget, Apr. 2012, 3(4), 414-425.

(56) References Cited

OTHER PUBLICATIONS

O'shannessy et al, Poster Presentations—Antibody Therapeutics Abstract 2516: Immunohistochemical characterization of a novel, highly sensitive monoclonal antibody to folate receptor a, Proceedings: AACR 103rd Annual Meeting 2012—Mar. 31-Apr. 4, 2012; Chicago, IL, Cancer Research, Apr. 15, 2012, 72(8), Supplement 1, pp. 2.

Parker et al, "Folate receptor expression in carcinomas and normal tissues determined by a quantitative radioligand binding assay" Analytical Biochemistry, Mar. 2005, 338(2), 284-293.

Saba et al, "Examining expression of folate receptor in squamous cell carcinoma of the head and neck as a target for a novel nanotherapeutic drug" Head Neck, Apr. 2009, 31(4), 475-481.

U.S. Appl. No. 13/289,892: Office Action dated Oct. 24, 2012, 28 pages.

Weitman et al, "Cellular Localization of the Folate Receptor: Potential Role in Drug Toxicity and Folate Homeostasis" Cancer Research, Dec. 1, 1992, 52, 6708-6711.

Weitman et al, "Distribution of the Folate Receptor GP38 in Normal and Malignant Cell Lines and Tissues1", Cancer Research 52, Jun. 15, 1992, 52(12), 3396-3401.

Yang et al, "The Folate ReceptorA Is FrequentlyOverexpressedinOsteosarcoma Samples andPiaysaRoleintheUptakeof the Physiologic Substrate 5-Methyltetrahydrofolate" Clinical Cancer Research, May 1, 2007, 13(9), 2557-2567.

Zanten-Przybysz, Iwona van, et al., "Influence of the Route of Administration on Targeting of Ovarian Cancer with the Chimeric Monoclonal Antibody MOv18: I.V. VS. I.P.," *Internationa/Journal of Cancer*, Apr. 2001, 92:106-114.

```
         10          20          30          40          50          60
MAQRMTTQLL  LLLVWVAVVG  EAQTRIAWAR  TELLNVCMNA  KHHKEKPGPE  DKLHEQCRPW 70          80          90         100         110         120
RKNACCSTNT  SQEAHKDVSY  LYRFNWNHCG  EMAPACKRHF  IQDTCLYECS  PNLGPWIQQV 130         140         150         160         170         180
DQSWRKERVL  NVPLCKEDCE  QWWEDCRTSY  TCKSNWHKGW  NWTSGFNKCA  VGAACQPFHF 190         200         210         220         230         240
YFPTPTVLCN  EIWTHSYKVS  NYSRGSGRCI  QMWFDPAQGN  PNEEVARFYA  AAMSGAGPWA

250
AWPFLLSLAL  MLLWLLS       (SEQ ID NO:1)
```

Legend
Residues 1-24 (double underscore) = Signal Sequence (not present in rh-FRα)
Residues 41-53 (shaded) = MAb 9F3 (PTA-11887) epitope
Residues 68-80 and 92-105 (shaded) = MAb 24F12 (PTA-11886) epitope
Residues 199-209 (shaded) = MAb 26B3 (PTA-11885) epitope
Residues 236-257 (underscore) = GPI-anchor Sequence (not present in rh-FRα)

Figure 2

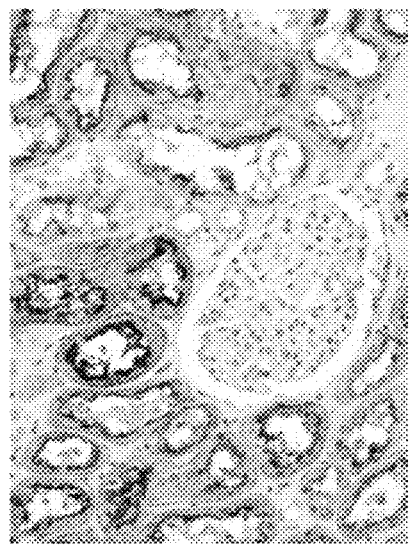
B.
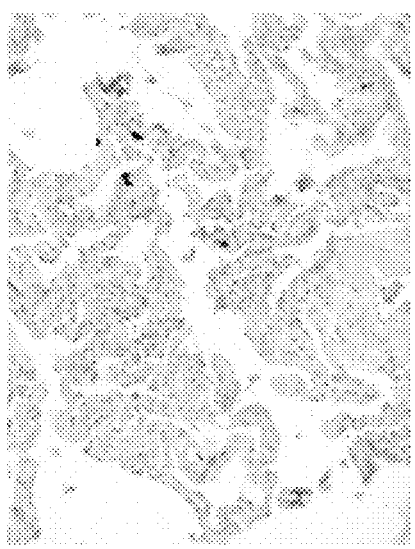
A.
Figure 5

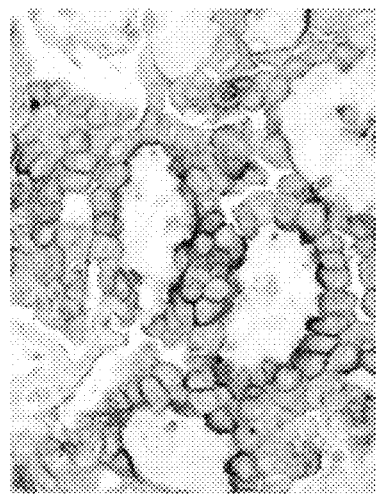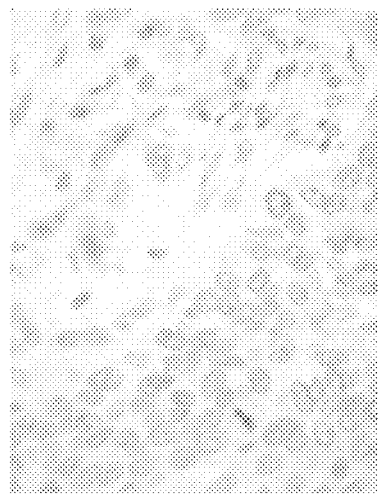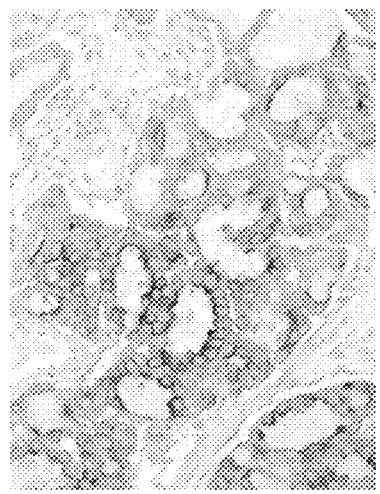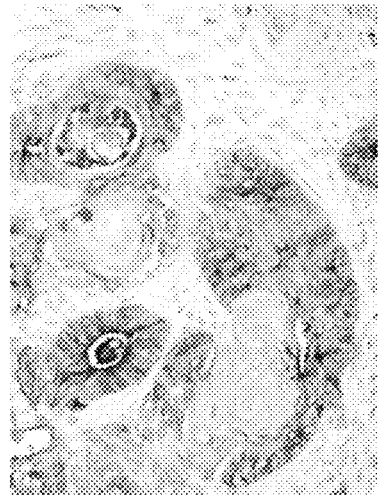
Figure 7

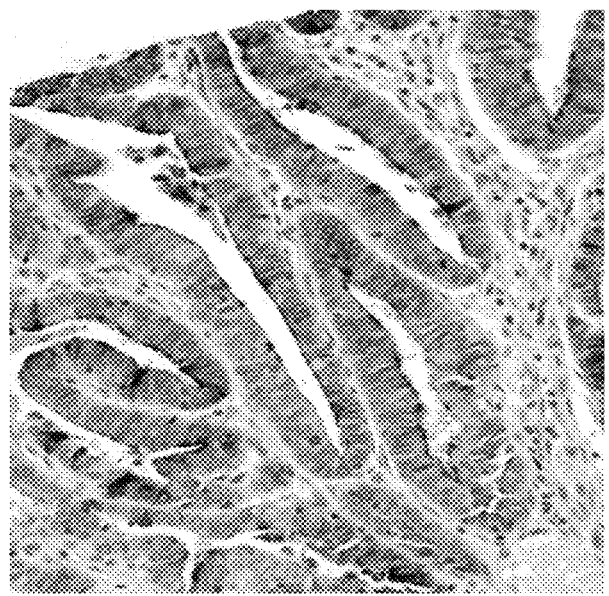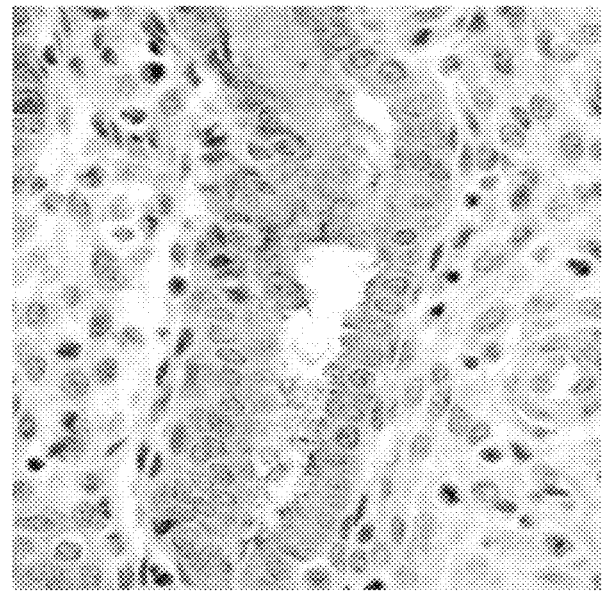
Figure 17

SEQUENCE LISTING

```
<160> NUMBER OF SEQ ID NOS: 66

<210> SEQ ID NO 1
<211> LENGTH: 257
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Ala Gln Arg Met Thr Thr Gln Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
                100                 105                 110

Leu Gly Pro Trp Ile Gln Gln Val Asp Gln Ser Trp Arg Lys Glu Arg
            115                 120                 125
```

```
Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 2
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

```
Arg Ala Ser Ser Thr Val Ser Tyr Ser Tyr Leu His
1               5                   10
```

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

```
Gly Thr Ser Asn Leu Ala Ser
1               5
```

<210> SEQ ID NO 4
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

```
Gln Gln Tyr Ser Gly Tyr Pro Leu Thr
1               5
```

<210> SEQ ID NO 5
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 5

Pro Ala Ile Met Ser Ala Ser Pro Gly Glu Lys Val Thr Met Thr Cys
1               5                   10                  15

Arg Ala Ser Ser Thr Val Ser Tyr Ser Tyr Leu His Trp Tyr Gln Gln
            20                  25                  30

Lys Ser Gly Ala Ser Pro Gln Leu Trp Ile Tyr Gly Thr Ser Asn Leu
        35                  40                  45

Ala Ser Gly Val Pro Ala Arg Phe Ser Gly Ser Gly Ser Gly Thr Ser
    50                  55                  60

Tyr Ser Leu Thr Ile Ser Ser Val Glu Ala Glu Asp Ala Ala Thr Tyr
65                  70                  75                  80

Tyr Cys Gln Gln Tyr Ser Gly Tyr Pro Leu Thr Phe Gly Ala Gly Thr
                85                  90                  95

Lys Leu Glu Leu Lys Arg Ala Asp Ala Ala Pro
            100                 105

<210> SEQ ID NO 6
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ser Gly Tyr Tyr Trp Asn
1               5

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Tyr Ile Lys Ser Asp Gly Ser Asn Asn Tyr Asn Pro Ser Leu Lys Asn
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Glu Trp Lys Ala Met Asp Tyr
1               5

<210> SEQ ID NO 9
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Ser Gly Pro Gly Leu Val Arg Pro Ser Gln Ser Leu Ser Leu Thr
1               5                   10                  15

Cys Ser Val Thr Gly Tyr Ser Ile Thr Ser Gly Tyr Tyr Trp Asn Trp
            20                  25                  30

Ile Arg Gln Phe Pro Gly Ser Arg Leu Glu Trp Met Gly Tyr Ile Lys
        35                  40                  45

Ser Asp Gly Ser Asn Asn Tyr Asn Pro Ser Leu Lys Asn Arg Ile Ser
    50                  55                  60

Ile Thr Arg Asp Thr Ser Lys Asn Gln Phe Phe Leu Lys Leu Asn Ser
65                  70                  75                  80

Val Thr Thr Glu Asp Thr Ala Thr Tyr Phe Cys Thr Arg Glu Trp Lys
                85                  90                  95

Ala Met Asp Tyr Trp Gly Gln Gly Thr Ser Val Thr Val Ser Ser Ala
                100                 105                 110

Lys Thr Thr Pro Pro Ser Val Tyr Pro Leu Ala Pro Gly Cys Gly Asp
        115                 120                 125

Thr

<210> SEQ ID NO 10
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Arg Ala Ser Glu Ser Val Asp Thr Tyr Gly Asn Asn Phe Ile His
1               5                   10                  15

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Leu Ala Ser Asn Leu Glu Ser
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Gln Asn Asn Gly Asp Pro Trp Thr
1               5

<210> SEQ ID NO 13
<211> LENGTH: 110
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 13

Pro Ala Ser Leu Ala Val Ser Leu Gly Gln Arg Ala Thr Ile Ser Cys
1               5                   10                  15

Arg Ala Ser Glu Ser Val Asp Thr Tyr Gly Asn Asn Phe Ile His Trp
            20                  25                  30

Tyr Gln Gln Lys Pro Gly Gln Pro Pro Lys Leu Leu Ile Tyr Leu Ala
        35                  40                  45

Ser Asn Leu Glu Ser Gly Val Pro Ala Arg Phe Ser Gly Ser Gly Ser
    50                  55                  60

Arg Thr Asp Phe Thr Leu Thr Ile Asp Pro Val Glu Ala Asp Asp Ala
65                  70                  75                  80

Ala Thr Tyr Tyr Cys Gln Gln Asn Asn Gly Asp Pro Trp Thr Phe Gly
                85                  90                  95

Gly Gly Thr Lys Leu Glu Ile Lys Arg Ala Asp Ala Ala Pro
            100                 105                 110

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

His Pro Tyr Met His
1               5

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Arg Ile Asp Pro Ala Asn Gly Asn Thr Lys Tyr Asp Pro Lys Phe Gln
1               5                   10                  15

Gly

<210> SEQ ID NO 16
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Glu Glu Val Ala Asp Tyr Thr Met Asp Tyr
1               5                   10

<210> SEQ ID NO 17
<211> LENGTH: 126
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gly Ala Glu Leu Val Lys Pro Gly Ala Ser Val Lys Leu Ser Cys Thr
1               5                   10                  15

Ala Ser Gly Phe Asn Ile Lys His Pro Tyr Met His Trp Val Lys Gln
            20                  25                  30

Arg Pro Asp Gln Gly Leu Glu Trp Ile Gly Arg Ile Asp Pro Ala Asn
        35                  40                  45

Gly Asn Thr Lys Tyr Asp Pro Lys Phe Gln Gly Lys Ala Thr Ile Thr
    50                  55                  60

Ala Asp Thr Ser Ser Asn Thr Ala Tyr Leu Gln Leu Ser Ser Leu Thr
65                  70                  75                  80

Ser Glu Asp Thr Ala Val Tyr Tyr Cys Gly Arg Glu Glu Val Ala Asp
                85                  90                  95

Tyr Thr Met Asp Tyr Trp Gly Gln Gly Thr Ser Val Thr Val Ser Ser
            100                 105                 110

Ala Lys Thr Thr Ala Pro Ser Val Tyr Pro Leu Ala Pro Val
        115                 120                 125

<210> SEQ ID NO 18
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ser Ala Ser Gln Gly Ile Asn Asn Phe Leu Asn
1               5                   10

<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Tyr Thr Ser Ser Leu His Ser
1               5

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gln His Phe Ser Lys Leu Pro Trp Thr
1               5

<210> SEQ ID NO 21
```

<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

Thr Ser Ser Leu Ser Ala Ser Leu Gly Asp Arg Val Thr Ile Ser Cys
1               5                   10                  15

Ser Ala Ser Gln Gly Ile Asn Asn Phe Leu Asn Trp Tyr Gln Gln Lys
            20                  25                  30

Pro Asp Gly Thr Val Lys Leu Leu Ile Tyr Tyr Thr Ser Ser Leu His
        35                  40                  45

Ser Gly Val Pro Ser Arg Phe Ser Gly Ser Gly Ser Gly Thr Asp Tyr
    50                  55                  60

Ser Leu Thr Ile Ser Asn Leu Glu Pro Glu Asp Ile Ala Ile Tyr Tyr
65                  70                  75                  80

Cys Gln His Phe Ser Lys Leu Pro Trp Thr Phe Gly Gly Gly Thr Lys
                85                  90                  95

Leu Glu Ile Lys Arg Ala Asp Ala Ala Pro
            100                 105

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

Ser Tyr Ala Met Ser
1               5

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 23

Glu Ile Gly Ser Gly Gly Ser Tyr Thr Tyr Tyr Pro Asp Thr Val Thr
1               5                   10                  15

Gly

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 24

Glu Thr Thr Ala Gly Tyr Phe Asp Tyr
1               5

```
<210> SEQ ID NO 25
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ser Gly Gly Gly Leu Val Arg Pro Gly Ser Leu Lys Leu Ser Cys
1               5                   10                  15

Ala Ala Ser Gly Phe Thr Phe Ser Ser Tyr Ala Met Ser Trp Val Arg
                20                  25                  30

Gln Ser Pro Glu Lys Arg Leu Glu Trp Val Ala Glu Ile Gly Ser Gly
            35                  40                  45

Gly Ser Tyr Thr Tyr Tyr Pro Asp Thr Val Thr Gly Arg Phe Thr Ile
        50                  55                  60

Ser Arg Asp Asn Ala Lys Ser Thr Leu Tyr Leu Glu Met Ser Ser Leu
65                  70                  75                  80

Arg Ser Glu Asp Thr Ala Ile Tyr Tyr Cys Ala Arg Glu Thr Thr Ala
                85                  90                  95

Gly Tyr Phe Asp Tyr Trp Gly Gln Gly Thr Thr Leu Thr Val Ser Ser
                100                 105                 110

<210> SEQ ID NO 26
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Arg Thr Ser Glu Asn Ile Phe Ser Tyr Leu Ala
1               5                   10

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asn Ala Lys Thr Leu Ala Glu
1               5

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gln His His Tyr Ala Phe Pro Trp Thr
1               5

<210> SEQ ID NO 29
```

```
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Pro Ala Ser Leu Ser Ala Ser Val Gly Glu Thr Val Thr Ile Thr Cys
1               5                   10                  15

Arg Thr Ser Glu Asn Ile Phe Ser Tyr Leu Ala Trp Tyr Gln Gln Lys
            20                  25                  30

Gln Gly Ile Ser Pro Gln Leu Leu Val Tyr Asn Ala Lys Thr Leu Ala
        35                  40                  45

Glu Gly Val Pro Ser Arg Phe Ser Gly Ser Gly Ser Gly Thr Gln Phe
    50                  55                  60

Ser Leu Lys Ile Asn Ser Leu Gln Pro Glu Asp Phe Gly Ser Tyr Tyr
65                  70                  75                  80

Cys Gln His His Tyr Ala Phe Pro Trp Thr Phe Gly Gly Gly Ser Lys
                85                  90                  95

Leu Glu Ile Lys Arg Ala Asp Ala Ala Pro
            100                 105

<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Tyr Phe Met Asn
1               5

<210> SEQ ID NO 31
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Arg Ile Phe Pro Tyr Asn Gly Asp Thr Phe Tyr Asn Gln Lys Phe Lys
1               5                   10                  15

Gly

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Thr His Tyr Phe Asp Tyr
1               5
```

```
<210> SEQ ID NO 33
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gly Pro Glu Leu Val Lys Pro Gly Ala Ser Val Lys Ile Ser Cys Lys
1               5                   10                  15

Ala Ser Asp Tyr Ser Phe Thr Gly Tyr Phe Met Asn Trp Val Met Gln
            20                  25                  30

Ser His Gly Lys Ser Leu Glu Trp Ile Gly Arg Ile Phe Pro Tyr Asn
        35                  40                  45

Gly Asp Thr Phe Tyr Asn Gln Lys Phe Lys Gly Arg Ala Thr Leu Thr
    50                  55                  60

Val Asp Lys Ser Ser Ser Thr Ala His Met Glu Leu Arg Ser Leu Ala
65                  70                  75                  80

Ser Glu Asp Ser Ala Val Tyr Phe Cys Ala Arg Gly Thr His Tyr Phe
                85                  90                  95

Asp Tyr Trp Gly Gln Gly Thr Thr Leu Thr Val Ser Ser Ala Lys Thr
            100                 105                 110

Thr Pro Pro Ser Val Tyr Pro Leu Ala Pro Gly Ser Ala Ala Gln Thr
        115                 120                 125

<210> SEQ ID NO 34
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
agggccagct caactgtaag ttacagttac ttgcac                              36

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
ggcacatcca acttggcttc t                                              21

<210> SEQ ID NO 36
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
cagcagtaca gtggttaccc actcacg                                        27

<210> SEQ ID NO 37
```

```
<211> LENGTH: 323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
ccagcaatca tgtctgcatc tccaggggaa aaggtcacca tgacctgcag ggccagctca    60
actgtaagtt acagttactt gcactggtac cagcagaagt caggtgcctc cccccaactc   120
tggatttatg gcacatccaa cttggcttct ggagtccctg ctcgcttcag tggcagtggg   180
tctgggacct cttactctct cacaatcagc agtgtggagg ctgaagatgc tgccacttat   240
tactgccagc agtacagtgg ttacccactc acgttcggtg ctgggaccaa gctggagctg   300
aaacgggctg atgctgcacc aac                                          323

<210> SEQ ID NO 38
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
agtggttatt actggaac                                                 18

<210> SEQ ID NO 39
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
tacataaagt ccgacggtag caataattac aacccatctc tcaaaaat                48

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gagtggaagg ctatggacta c                                             21

<210> SEQ ID NO 41
<211> LENGTH: 389
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
gagtcaggac ctggcctcgt gagaccttct cagtctctgt ctctcacctg ctctgtcact    60
ggctactcca tcaccagtgg ttattactgg aactggatcc ggcagtttcc aggaagcaga   120
```

```
ctggaatgga tgggctacat aaagtccgac ggtagcaata attacaaccc atctctcaaa    180
aatcgaatct ccatcactcg tgacacatct aagaaccagt ttttcctgaa gttgaattct    240
gtgactactg aggacacagc tacatatttc tgtacaaggg agtggaaggc tatggactac    300
tggggtcagg gaacctcagt caccgtctcc tcagccaaaa caacaccccc atcagtctat    360
ccactggccc ctgggtgtgg agatacaac                                      389

<210> SEQ ID NO 42
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
agagccagtg aaagtgttga tacttatggc aataatttta tacac                    45

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
cttgcatcca acctagaatc t                                              21

<210> SEQ ID NO 44
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cagcaaaata atggggatcc gtggacg                                        27

<210> SEQ ID NO 45
<211> LENGTH: 331
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
ccagcttctt tggctgtgtc tctagggcag agggccacca tatcctgcag agccagtgaa    60
agtgttgata cttatggcaa taattttata cactggtacc agcagaaacc aggacagcca    120
cccaaactcc tcatttatct tgcatccaac ctagaatctg ggtccctgc aggttcagt      180 ggcagtgggt ctaggacaga cttcaccctc accattgatc ctgtggaggc tgatgatgct    240
gcaacctatt actgtcagca aaataatggg gatccgtgga cgttcggtgg aggcaccaag    300
ctggagatca aacgggctga tgctgcacca a                                   331

<210> SEQ ID NO 46
```

<210> SEQ ID NO 46
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 46
cacccctata tgcac        15

<210> SEQ ID NO 47
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 47
aggattgatc ctgcgaatgg taatactaaa tatgacccga agttccaggg c        51

<210> SEQ ID NO 48
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 48
gaggaggtgg cggactatac tatggactac        30

<210> SEQ ID NO 49
<211> LENGTH: 380
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 49
ggggcagagc ttgtgaagcc aggggcctca gtcaagttgt cctgcacagc ttctggcttc        60
aacattaaac acccctatat gcactgggtg aagcagaggc ctgaccaggg cctggagtgg       120
attggaagga ttgatcctgc gaatggtaat actaaatatg acccgaagtt ccagggcaag       180
gccactataa cagcagacac atcctccaac acagcctacc tacagctcag cagcctgaca       240
tctgaggaca ctgccgtcta ttactgtggt agagaggagg tggcggacta tactatggac       300
tactggggtc aaggaacctc agtcaccgtc tcctcagcca aaacaacagc ccatcggtc        360
tatccactgg cccctgtgtg       380

<210> SEQ ID NO 50
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 50
agtgcaagtc agggcattaa caattttta aac        33

<210> SEQ ID NO 51
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 51
tacacatcaa gtttacactc a                                        21

<210> SEQ ID NO 52
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 52
cagcacttta gtaagcttcc gtggacg                                  27

<210> SEQ ID NO 53
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 53
acatcctccc tgtctgcctc tctgggagac agagtcacca tcagttgcag tgcaagtcag    60
ggcattaaca attttttaaa ctggtatcag cagaaaccag atggcactgt taaactcctg   120
atctattaca catcaagttt acactcagga gtcccatcaa ggttcagtgg cagtgggtct   180
gggacagatt attctctcac catcagcaac ctggaacctg aagatattgc catatactat   240
tgtcagcact ttagtaagct tccgtggacg ttcggtggag gcaccaagct ggaaatcaaa   300
cgggctgatg ctgcaccaac                                              320

<210> SEQ ID NO 54
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 54
agctatgcca tgtct                                               15

<210> SEQ ID NO 55
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 55

```
gaaattggta gtggtggtag ttacacctac tatccagaca ctgtgacggg c        51
```

<210> SEQ ID NO 56
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56

```
gaaactacgg cgggctactt tgactac                                   27
```

<210> SEQ ID NO 57
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57

```
tctggggag gcttagtgag gcctggaggg tccctgaaac tctcctgtgc agcctctgga    60
ttcactttca gtagctatgc catgtcttgg gttcgccagt ctccagagaa gaggctggag  120
tgggtcgcag aaattggtag tggtggtagt tacacctact atccagacac tgtgacgggc  180
cgattcacca tctccagaga caatgccaag agcaccctgt acctggaaat gagcagtctg  240
aggtctgagg acacggccat ctattactgt gcaaggaaa ctacggcggg ctactttgac   300
tactggggcc aaggcaccac tctcacagtc tcctca                            336
```

<210> SEQ ID NO 58
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58

```
cgaacaagtg agaatatttt cagttattta gca                            33
```

<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59

```
aatgcaaaaa ccttagcaga g                                         21
```

<210> SEQ ID NO 60
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
caacatcatt atgctttcc gtggacg 27

<210> SEQ ID NO 61
<211> LENGTH: 320
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61
ccagcctccc tatctgcatc tgtgggagaa actgtcacca tcacatgtcg aacaagtgag      60
aatattttca gttatttagc atggtatcag cagaaacagg gaatatctcc tcagctcctg     120
gtctataatg caaaaacctt agcagagggt gtgccatcaa ggttcagtgg cagtggatca     180
ggcacacagt tttctctgaa gatcaacagc ctgcagcctg aagattttgg gagttattac     240
tgtcaacatc attatgcttt tccgtggacg ttcggtggag ctccaagct ggaaatcaaa     300 cgggctgatg ctgcaccaac                                                 320

<210> SEQ ID NO 62
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ggctacttta tgaac                                                      15

<210> SEQ ID NO 63
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63 cgtattttc cttacaatgg tgatactttc tacaaccaga gttcaaggg c                 51

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
gggactcatt actttgacta c                                               21

<210> SEQ ID NO 65
<211> LENGTH: 386
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 65
ggacctgagc tggtgaagcc tggggcttca gtgaagatat cctgcaaggc ttctgattac      60
tcttttactg gctactttat gaactgggtg atgcagagcc atggaaagag ccttgagtgg     120
attggacgta tttttcctta caatggtgat actttctaca accagaagtt caagggcagg     180
gccacattga ctgtagacaa atcctctagc acagcccaca tggagctccg gagcctggca     240
tctgaggact ctgcagtcta tttttgtgca agagggactc attactttga ctactggggc     300
caaggcacca ctctcactgt ctcctcagcc aaaacgacac ccccatctgt ctatccactg     360
gcccctggat ctgctgccca aactaa                                          386

<210> SEQ ID NO 66
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 66

His His His His His His
1               5
```

US 8,834,877 B2

ANTI-FOLATE RECEPTOR ALPHA ANTIBODIES AND USES THEREOF

CROSS-REFERENCE TO RELATED APPLICATIONS

This application is a divisional of U.S. application Ser. No. 13/548,775, filed Jul. 13, 2012, which claims the benefit of U.S. provisional application No. 61/508,444, filed Jul. 15, 2011; U.S. provisional application No. 61/604,412, filed Feb. 28, 2012; and U.S. provisional application No. 61/604,954, filed Feb. 29, 2012, each of which is incorporated by reference herein in its entirety.

TECHNICAL FIELD

The subject matter provided herein relates to folate receptor alpha (FRα)-specific antibodies as well as methods of producing and using the antibodies.

BACKGROUND

In humans, the high affinity receptor for folate comes in four isoforms: alpha, beta, gamma, and delta. The alpha, beta and delta forms are typically bound to the membranes of cells by a glycosyl phosphatidylinositol (GPI) anchor. They recycle between extracellular and endocytic compartments and are capable of transporting folate into the cell. Soluble forms of folate receptor may be derived by the action of proteases or phospholipase on membrane anchored folate receptors.

Folate receptor alpha (also referred to as FRα, FR-alpha, FOLR-1 or FOLR1) is expressed in a variety of epithelial tissues, including those of the choroid plexus, lung, thyroid, kidney, uterus, breast, Fallopian tube, epididymis, and salivary glands. Weitman, S D et al., *Cancer Res* 52: 3396-3401 (1992); Weitman S D et al., *Cancer Res* 52: 6708-6711 (1992). Overexpression of FRα has been observed in various cancers, including lung cancer (e.g., carcinoid tumors, and non-small cell lung cancers, such as adenocarcinomas); mesothelioma; ovarian cancer; renal cancer; brain cancer (e.g., anaplastic ependymoma, cerebellar juvenile pilocytic astrocytoma, and brain metastases); cervical cancer; nasopharyngeal cancer; mesodermally derived tumor; squamous cell carcinoma of the head and neck; endometrial cancer; papillary serous and endometrioid adenocarcinomas of the ovary, serous cystadenocarcinomas of the ovary, breast cancer; bladder cancer; pancreatic cancer; bone cancer (e.g., high-grade osteosarcoma); pituitary cancer (e.g., pituitary adenomas); colorectal cancer and medullary thyroid cancer. See e.g., U.S. Pat. No. 7,754,698; U.S. Patent Application No. 2005/0232919; Intl. Publ. No. WO 2009/132081; Bueno R et al., *J of Thoracic and Cardiovascular Surgery*, 121(2): 225-233 (2001); Elkanat H & Ratnam M. *Frontiers in Bioscience*, 11, 506-519 (2006); Basal et al., PLoS ONE, 4(7):6292 (2009); Fisher R E *J Nucl Med*, 49: 899-906 (2008); Franklin, W A et al., *Int J Cancer*, Suppl 8: 89-95 (1994); Hartmann L C et al., *Int J Cancer* 121: 938-942 (2007); Iwakiri S et al., *Annals of Surgical Oncology*, 15(3): 889-899 (2008); European patent publication EP 2199796, Parker N. et al., *Analytical Biochemistry*, 338: 284-293 (2005); Weitman, S D et al., *Cancer Res* 52: 3396-3401 (1992); Saba N F et al., *Head Neck*, 31(4): 475-481 (2009); Yang R et al., *Clin Cancer Res* 13: 2557-2567 (2007). In some types of cancers (e.g., squamous cell carcinoma of the head and neck), a high level of FRα expression is associated with a poor prognosis, whereas in other types of cancers (e.g., non-small-cell lung cancers), a higher level of FRα expression is associated with a more favorable prognosis. See, e.g., Iwakiri S et al., *Annals of Surgical Oncology*, 15(3): 889-899; Saba N F et al., *Head Neck*, 31(4): 475-481 (2009).

Earlier detection of cancer improves survival rates and quality of life. To improve the likelihood of early detection and treatment, a pressing need exists for non-invasive methods for diagnosing FRα-expressing cancers and for monitoring existing FRα-expressing cancers.

SUMMARY

Provided herein are antibodies that specifically bind to FRα. Also described are related polynucleotides capable of encoding the provided antibodies, cells expressing the provided antibodies, as well as associated vectors and detectable antibody labels. In addition, methods of using the provided antibodies are described. For example, the provided antibodies may be used to diagnose cancer; monitor cancer progression, regression, or stable disease; develop a prognosis for cancer in a subject; to determine whether or not a patient should be treated for cancer, or to determine whether or not a subject is afflicted with FRα-expressing cancer and thus may be amenable to treatment with a FRα-specific anti-cancer therapeutic.

Folate Receptor Alpha (FRα)-Specific Antibodies

Described herein are isolated antibodies and antigen-binding fragments that specifically bind to FRα. In some embodiments, the antibodies or antigen-binding fragments are murine IgG, or derivatives thereof.

In some embodiments, antibodies or antigen-binding fragments may include a light chain CDR1 amino acid sequence substantially the same as, or identical to, SEQ ID NO: 2. In some embodiments, antibodies or antigen-binding fragments may include a light chain CDR2 amino acid sequence substantially the same as, or identical to, SEQ ID NO: 3. In some embodiments, antibodies or antigen-binding fragments may include a light chain CDR3 amino acid sequence substantially the same as, or identical to, SEQ ID NO: 4. In some embodiments, antibodies or antigen-binding fragments may include a heavy chain CDR1 amino acid sequence substantially the same as, or identical to, SEQ ID NO: 6. In some embodiments, antibodies or antigen-binding fragments may include a heavy chain CDR2 amino acid sequence substantially the same as, or identical to, SEQ ID NO: 7. In some embodiments, antibodies or antigen-binding fragments may include a heavy chain CDR3 amino acid sequence substantially the same as, or identical to, SEQ ID NO: 8. The antibodies or antigen-binding fragments may include a light chain having a CDR1 amino acid sequence substantially the same as, or identical to, SEQ ID NO: 2; a CDR2 amino acid sequence substantially the same as, or identical to, SEQ ID NO: 3; and a CDR3 amino acid sequence substantially the same as, or identical to, SEQ ID NO: 4. The antibodies or antigen-binding fragments may include a heavy chain having a CDR1 amino acid sequence substantially the same as, or identical to, SEQ ID NO: 6; a CDR2 amino acid sequence substantially the same as, or identical to, SEQ ID NO: 7; and a CDR3 amino acid sequence substantially the same as, or identical to, SEQ ID NO: 8. The antibodies or antigen-binding fragments may include a light chain having a CDR1 amino acid sequence substantially the same as, or identical to, SEQ ID NO: 2; a CDR2 amino acid sequence substantially the same as, or identical to, SEQ ID NO: 3; and a CDR3 amino acid sequence substantially the same as, or identical to, SEQ ID NO: 4, and also have a heavy chain having a CDR1 amino acid sequence substantially the same as, or identical to, SEQ ID NO: 6; a CDR2 amino acid sequence substantially the same as, or identical to, SEQ ID NO: 7; and a CDR3 amino acid sequence substantially the same as, or identical to, SEQ ID NO: 8.

The described antibodies or antigen-binding fragments may include a light chain variable domain that includes an amino acid sequence substantially the same as, or identical to, SEQ ID NO: 5. In some embodiments, an isolated polynucleotide that includes a sequence substantially the same as, or identical to, SEQ ID NO: 37 may encode this light chain variable domain amino acid sequence. The described antibodies or antigen-binding fragments may include a heavy chain variable domain that includes an amino acid sequence substantially the same as, or identical to, SEQ ID NO: 9. In some embodiments, an isolated polynucleotide that includes a sequence substantially the same as, or identical to, SEQ ID NO: 41 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 5, and the heavy chain variable domain includes an amino acid sequence substantially the same as, or identical to, SEQ ID NO: 9. In some embodiments are provided the 9F3.H9.H3.H3.B5.G2 (9F3) antibody or antigen-binding fragments thereof, capable of binding either a native or non-reduced forms of FRα.

In some embodiments, the 9F3 antibody is produced by antibody-producing cells deposited with the American Type Culture Collection (10801 University Blvd., Manassas, Va. 20110-2209) on May 19, 2011 and have been assigned Accession No. PTA-11887. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to native or nonreduced forms of FRα. In some embodiments, the isolated polynucleotides encode an antibody or antigen-binding fragment thereof having a light chain CDR1 sequence substantially the same as, or identical to, SEQ ID NO: 2, for example SEQ ID NO: 34. In some embodiments, the isolated polynucleotides encode an antibody or antigen-binding fragment thereof having a light chain CDR2 substantially the same as, or identical to, SEQ ID NO: 3, for example SEQ ID NO: 35. In some embodiments, the isolated polynucleotides encode an antibody or antigen-binding fragment thereof having a light chain CDR3 substantially the same as, or identical to, SEQ ID NO: 4, for example SEQ ID NO: 36. In some embodiments, the isolated polynucleotides encode an antibody or antigen-binding fragment thereof having a heavy chain CDR1 substantially the same as, or identical to, SEQ ID NO: 6, for example SEQ ID NO: 38. In some embodiments, the isolated polynucleotides encode an antibody or antigen-binding fragment thereof having a heavy chain CDR2 substantially the same as, or identical to, SEQ ID NO: 7, for example SEQ ID NO: 39. In some embodiments, the isolated polynucleotides encode an antibody or antigen-binding fragment thereof having a heavy chain CDR3 substantially the same as, or identical to, SEQ ID NO: 8, for example SEQ ID NO: 40. The isolated polynucleotides may encode an antibody or antigen-binding fragment thereof having a light chain with a CDR1 substantially the same as, or identical to, SEQ ID NO: 2, for example SEQ ID NO: 34; a CDR2 substantially the same as, or identical to, SEQ ID NO: 3, for example SEQ ID NO: 35; and a CDR3 substantially the same as, or identical to, SEQ ID NO: 4, for example SEQ ID NO: 36. The isolated polynucleotides may encode an antibody or antigen-binding fragment thereof having a heavy chain CDR1 substantially the same as, or identical to, SEQ ID NO: 6, for example SEQ ID NO: 38; a CDR2 substantially the same as, or identical to, SEQ ID NO: 7, for example SEQ ID NO: 39; and a CDR3 substantially the same as, or identical to, SEQ ID NO: 8, for example SEQ ID NO: 40. The isolated polynucleotides may encode an antibody or antigen-binding fragment thereof having a light chain CDR1 substantially the same as, or identical to, SEQ ID NO: 2, for example SEQ ID NO: 34; a CDR2 encoded by a nucleotide sequence substantially the same as, or identical to, SEQ ID NO: 3, for example SEQ ID NO: 35; and a CDR3 encoded by a nucleotide sequence substantially the same as, or identical to, SEQ ID NO: 4, for example SEQ ID NO: 36; and a heavy chain CDR1 substantially the same as, or identical to, SEQ ID NO: 6, for example SEQ ID NO: 38; a CDR2 substantially the same as, or identical to, SEQ ID NO: 7, for example SEQ ID NO: 39; and a CDR3 substantially the same as, or identical to, SEQ ID NO: 8, for example SEQ ID NO: 40. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 5, for example SEQ ID NO: 37. In some embodiments the described isolated polynucleotides may encode antibodies or antigen-binding fragments that have a heavy chain variable domain segment that includes an amino acid sequence substantially the same as, or identical to, SEQ ID NO: 9, for example SEQ ID NO: 41. In some embodiments the described isolated polynucleotides may encode antibodies or antigen-binding fragments that have a light chain variable domain segment that includes an amino acid sequence substantially the same as, or identical to, SEQ ID NO: 5, for example SEQ ID NO: 37; and a heavy chain variable domain segment that includes an amino acid sequence substantially the same as, or identical to, SEQ ID NO: 9, for example SEQ ID NO: 41. The isolated polynucleotides capable of encoding the variable domain segments provided herein may be included on the same, or different, vectors to produce an antibodies or antigen-binding fragments. Polynucleotides described herein may encode the 9F3 antibody or antigen-binding fragments thereof, capable of binding native or non-reduced forms of FRα.

Described herein are isolated antibodies and antigen-binding fragments that specifically bind to native or nonreduced forms of FRα. In some embodiments, the antibodies or antigen-binding fragments are murine IgG, or derivatives thereof. While the antibodies or antigen-binding fragments may be human, humanized, or chimeric, the antibodies or antigen-binding fragments exemplified herein are murine. In some embodiments, antibodies or antigen-binding fragments may include a light chain CDR1 amino acid sequence substantially the same as, or identical to, SEQ ID NO: 10. In some embodiments, antibodies or antigen-binding fragments may include a light chain CDR2 amino acid sequence substantially the same as, or identical to, SEQ ID NO: 11. In some embodiments, antibodies or antigen-binding fragments may include a light chain CDR3 amino acid sequence substantially the same as, or identical to, SEQ ID NO: 12. In some embodiments, antibodies or antigen-binding fragments may include a heavy chain CDR1 amino acid sequence substantially the same as, or identical to, SEQ ID NO: 14. In some embodiments, antibodies or antigen-binding fragments may include a heavy chain CDR2 amino acid sequence substantially the same as, or identical to, SEQ ID NO: 15. In some embodiments, antibodies or antigen-binding fragments may include a heavy chain CDR3 amino acid sequence substantially the same as, or identical to, SEQ ID NO: 16. The antibodies or antigen-binding fragments may include a light chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12. The antibodies or antigen-binding fragments may include a heavy chain having a CDR1 amino acid sequence substantially the same as, or identical to, SEQ ID NO: 14; a CDR2 amino acid sequence substantially the same as, or identical to, SEQ ID NO: 15; and a CDR3 amino acid sequence substantially the same as, or identical to, SEQ ID NO: 16. The antibodies or antigen-binding fragments may include a light chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12, and also have a heavy chain having a CDR1 amino acid sequence substantially the same as, or identical to, SEQ ID NO: 14; a CDR2 amino acid sequence substantially the same as, or identical to, SEQ ID NO: 15; and a CDR3 amino acid sequence substantially the same as, or identical to, SEQ ID NO: 16.

The described antibodies or antigen-binding fragments may include a light chain variable domain that includes an amino acid sequence substantially the same as, or identical to, SEQ ID NO: 13. In some embodiments, an isolated polynucleotide that includes a sequence substantially the same as, or identical to, SEQ ID NO: 45 may encode this light chain variable domain amino acid sequence. The described antibodies or antigen-binding fragments may include a heavy chain variable domain that includes an amino acid sequence substantially the same as, or identical to, SEQ ID NO: 17. In some embodiments, an isolated polynucleotide that includes a sequence substantially the same as, or identical to, SEQ ID NO: 49 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 13, and the heavy chain variable domain includes an amino acid sequence substantially the same as, or identical to, SEQ ID NO: 17. In some embodiments are provided the 19D4.B7 (19D4) antibody or antigen-binding fragments thereof, capable of binding either a native or nonreduced forms of FRα.

In some embodiments, the 19D4 antibody is produced by antibody-producing cells deposited with the American Type Culture Collection (10801 University Blvd., Manassas, Va. 20110-2209) on May 19, 2011 and have been assigned Accession No. PTA-11884. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to either a native or nonreduced forms of FRα. In some embodiments, the isolated polynucleotides encode an antibody or antigen-binding fragment thereof having a light chain CDR1 sequence substantially the same as, or identical to, SEQ ID NO: 10, for example SEQ ID NO: 42. In some embodiments, the isolated polynucleotides encode an antibody or antigen-binding fragment thereof having a light chain CDR2 substantially the same as, or identical to, SEQ ID NO: 11, for example SEQ ID NO: 43. In some embodiments, the isolated polynucleotides encode an antibody or antigen-binding fragment thereof having a light chain CDR3 substantially the same as, or identical to, SEQ ID NO: 12, for example SEQ ID NO: 44. In some embodiments, the isolated polynucleotides encode an antibody or antigen-binding fragment thereof having a heavy chain CDR1 substantially the same as, or identical to, SEQ ID NO: 14, for example SEQ ID NO: 46. In some embodiments, the isolated polynucleotides encode an antibody or antigen-binding fragment thereof having a heavy chain CDR2 substantially the same as, or identical to, SEQ ID NO: 15, for example SEQ ID NO: 47. In some embodiments, the isolated polynucleotides encode an antibody or antigen-binding fragment thereof having a heavy chain CDR3 substantially the same as, or identical to, SEQ ID NO: 16, for example SEQ ID NO: 48. The polynucleotides may encode an antibody or antigen-binding fragment thereof having a light chain with a CDR1 substantially the same as, or identical to, SEQ ID NO: 10, for example SEQ ID NO: 42; a CDR2 substantially the same as, or identical to, SEQ ID NO: 11, for example SEQ ID NO: 43; and a CDR3 substantially the same as, or identical to, SEQ ID NO: 12, for example SEQ ID NO: 44. The polynucleotides may encode an antibody or antigen-binding fragment thereof having a heavy chain CDR1 substantially the same as, or identical to, SEQ ID NO: 14, for example SEQ ID NO: 46; a CDR2 substantially the same as, or identical to, SEQ ID NO: 15, for example SEQ ID NO: 47; and a CDR3 substantially the same as, or identical to, SEQ ID NO: 16, for example SEQ ID NO: 48. The polynucleotides may encode an antibody or antigen-binding fragment thereof having a light chain CDR1 substantially the same as, or identical to, SEQ ID NO: 10, for example SEQ ID NO: 42; a CDR2 encoded by a nucleotide sequence substantially the same as, or identical to, SEQ ID NO: 11, for example SEQ ID NO: 43; and a CDR3 encoded by a nucleotide sequence substantially the same as, or identical to, SEQ ID NO: 12, for example SEQ ID NO: 44; and a heavy chain CDR1 substantially the same as, or identical to, SEQ ID NO: 14, for example SEQ ID NO: 46; a CDR2 substantially the same as, or identical to, SEQ ID NO: 15, for example SEQ ID NO: 47; and a CDR3 substantially the same as, or identical to, SEQ ID NO: 16, for example SEQ ID NO: 48. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 13, for example SEQ ID NO: 45. In some embodiments the described polynucleotides may encode antibodies or antigen-binding fragments that have a heavy chain variable domain segment that includes an amino acid sequence substantially the same as, or identical to, SEQ ID NO: 17, for example SEQ ID NO: 49. In some embodiments the described polynucleotides may encode antibodies or antigen-binding fragments that have a light chain variable domain segment that includes an amino acid sequence substantially the same as, or identical to, SEQ ID NO: 13, for example SEQ ID NO: 45; and a heavy chain variable domain segment that includes an amino acid sequence substantially the same as, or identical to, SEQ ID NO: 17, for example SEQ ID NO: 49. The polynucleotides capable of encoding the variable domain segments provided herein may be included on the same, or different, vectors to produce an antibodies or antigen-binding fragments. Polynucleotides described herein may encode the 19D4 antibody or antigen-binding fragments thereof, capable of binding native or nonreduced forms of FRα.

Described herein are isolated antibodies and antigen-binding fragments that specifically bind to FRα, capable of binding native or nonreduced forms of FRα. In some embodiments, the antibodies or antigen-binding fragments are murine IgG, or derivatives thereof. While the antibodies or antigen-binding fragments may be human, humanized, or chimeric, the antibodies or antigen-binding fragments exemplified herein are murine. In some embodiments, antibodies or antigen-binding fragments may include a light chain CDR1 amino acid sequence substantially the same as, or identical to, SEQ ID NO: 18. In some embodiments, antibodies or antigen-binding fragments may include a light chain CDR2 amino acid sequence substantially the same as, or identical to, SEQ ID NO: 19. In some embodiments, antibodies or antigen-binding fragments may include a light chain CDR3 amino acid sequence substantially the same as, or identical to, SEQ ID NO: 20. In some embodiments, antibodies or antigen-binding fragments may include a heavy chain CDR1 amino acid sequence substantially the same as, or identical to, SEQ ID NO: 22. In some embodiments, antibodies or antigen-binding fragments may include a heavy chain CDR2 amino acid sequence substantially the same as, or identical to, SEQ ID NO: 23. In some embodiments, antibodies or antigen-binding fragments may include a heavy chain CDR3 amino acid sequence substantially the same as, or identical to, SEQ ID NO: 24. The antibodies or antigen-binding fragments may include a light chain having a CDR1 amino acid sequence substantially the same as, or identical to, SEQ ID NO: 18; a CDR2 amino acid sequence substantially the same as, or identical to, SEQ ID NO: 19; and a CDR3 amino acid sequence substantially the same as, or identical to, SEQ ID NO: 20. The antibodies or antigen-binding fragments may include a heavy chain having a CDR1 amino acid sequence substantially the same as, or identical to, SEQ ID NO: 22; a CDR2 amino acid sequence substantially the same as, or identical to, SEQ ID NO: 23; and a CDR3 amino acid sequence substantially the same as, or identical to, SEQ ID NO: 24. The antibodies or antigen-binding fragments may include a light chain having a CDR1 amino acid sequence substantially the same as, or identical to, SEQ ID NO: 18; a CDR2 amino acid sequence substantially the same as, or identical to, SEQ ID NO: 19; and a CDR3 amino acid sequence substantially the same as, or identical to, SEQ ID NO: 20, and also have a heavy chain having a CDR1 amino acid sequence substantially the same as, or identical to, SEQ ID NO: 22; a CDR2 amino acid sequence substantially the same as, or identical to, SEQ ID NO: 23; and a CDR3 amino acid sequence substantially the same as, or identical to, SEQ ID NO: 24.

The described antibodies or antigen-binding fragments may include a light chain variable domain that includes an amino acid sequence substantially the same as, or identical to, SEQ ID NO: 21. In some embodiments, an isolated polynucleotide that includes a sequence substantially the same as, or identical to, SEQ ID NO: 53 may encode this light chain variable domain amino acid sequence. The described antibodies or antigen-binding fragments may include a heavy chain variable domain that includes an amino acid sequence substantially the same as, or identical to, SEQ ID NO: 25. In some embodiments, an isolated polynucleotide that includes a sequence substantially the same as, or identical to, SEQ ID NO: 57 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 21, and the heavy chain variable domain includes an amino acid sequence substantially the same as, or identical to, SEQ ID NO: 25. In some embodiments are provided the 24F12.B1 (24F12) antibody or antigen-binding fragments thereof, capable of binding either native or nonreduced forms of FRα.

In some embodiments, the 24F12 antibody is produced by antibody-producing cells deposited with the American Type Culture Collection (10801 University Blvd., Manassas, Va. 20110-2209) on May 19, 2011 and have been assigned Accession No. PTA-11886. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are polynucleotides that encode antibodies or antigen-binding fragments that specifically bind to FRα. In some embodiments, the isolated polynucleotides encode an antibody or antigen-binding fragment thereof having a light chain CDR1 sequence substantially the same as, or identical to, SEQ ID NO: 18, for example SEQ ID NO: 50. In some embodiments, the isolated polynucleotides encode an antibody or antigen-binding fragment thereof having a light chain CDR2 substantially the same as, or identical to, SEQ ID NO: 19, for example SEQ ID NO: 51. In some embodiments, the isolated polynucleotides encode an antibody or antigen-binding fragment thereof having a light chain CDR3 substantially the same as, or identical to, SEQ ID NO: 20, for example SEQ ID NO: 52. In some embodiments, the isolated polynucleotides encode an antibody or antigen-binding fragment thereof having a heavy chain CDR1 substantially the same as, or identical to, SEQ ID NO: 22, for example SEQ ID NO: 54. In some embodiments, the isolated polynucleotides encode an antibody or antigen-binding fragment thereof having a heavy chain CDR2 substantially the same as, or identical to, SEQ ID NO: 23, for example SEQ ID NO: 55. In some embodiments, the isolated polynucleotides encode an antibody or antigen-binding fragment thereof having a heavy chain CDR3 substantially the same as, or identical to, SEQ ID NO: 24, for example SEQ ID NO: 56. The polynucleotides may encode an antibody or antigen-binding fragment thereof having a light chain with a CDR1 substantially the same as, or identical to, SEQ ID NO: 18, for example SEQ ID NO: 50; a CDR2 substantially the same as, or identical to, SEQ ID NO:

19, for example SEQ ID NO: 51; and a CDR3 substantially the same as, or identical to, SEQ ID NO: 20, for example SEQ ID NO: 52. The polynucleotides may encode an antibody or antigen-binding fragment thereof having a heavy chain CDR1 substantially the same as, or identical to, SEQ ID NO: 22, for example SEQ ID NO: 54; a CDR2 substantially the same as, or identical to, SEQ ID NO: 23, for example SEQ ID NO: 55; and a CDR3 substantially the same as, or identical to, SEQ ID NO: 24, for example SEQ ID NO: 56. The polynucleotides may encode an antibody or antigen-binding fragment thereof having a light chain CDR1 substantially the same as, or identical to, SEQ ID NO: 18, for example SEQ ID NO: 50; a CDR2 encoded by a nucleotide sequence substantially the same as, or identical to, SEQ ID NO: 19, for example SEQ ID NO: 51; and a CDR3 encoded by a nucleotide sequence substantially the same as, or identical to, SEQ ID NO: 20, for example SEQ ID NO: 52; and a heavy chain CDR1 substantially the same as, or identical to, SEQ ID NO: 22, for example SEQ ID NO: 54; a CDR2 substantially the same as, or identical to, SEQ ID NO: 23, for example SEQ ID NO: 55; and a CDR3 substantially the same as, or identical to, SEQ ID NO: 24, for example SEQ ID NO: 56. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 21, for example SEQ ID NO: 53. In some embodiments the described polynucleotides may encode antibodies or antigen-binding fragments that have a heavy chain variable domain segment that includes an amino acid sequence substantially the same as, or identical to, SEQ ID NO: 25, for example SEQ ID NO: 57. In some embodiments the described polynucleotides may encode antibodies or antigen-binding fragments that have a light chain variable domain segment that includes an amino acid sequence substantially the same as, or identical to, SEQ ID NO: 21, for example SEQ ID NO: 53; and a heavy chain variable domain segment that includes an amino acid sequence substantially the same as, or identical to, SEQ ID NO: 25, for example SEQ ID NO: 57. The polynucleotides capable of encoding the variable domain segments provided herein may be included on the same, or different, vectors to produce an antibodies or antigen-binding fragments. Polynucleotides described herein may encode the 24F12 antibody or antigen-binding fragments thereof, capable of binding either native or nonreduced forms of FRα.

Described herein are isolated antibodies and antigen-binding fragments that specifically bind to FRα in either a native, nonreduced, or chemically preserved form. In some embodiments, the antibodies or antigen-binding fragments are murine IgG, or derivatives thereof. While the antibodies or antigen-binding fragments may be human, humanized, or chimeric, the antibodies or antigen-binding fragments exemplified herein are murine. In some embodiments, antibodies or antigen-binding fragments may include a light chain CDR1 amino acid sequence substantially the same as, or identical to, SEQ ID NO: 26. In some embodiments, antibodies or antigen-binding fragments may include a light chain CDR2 amino acid sequence substantially the same as, or identical to, SEQ ID NO: 27. In some embodiments, antibodies or antigen-binding fragments may include a light chain CDR3 amino acid sequence substantially the same as, or identical to, SEQ ID NO: 28. In some embodiments, antibodies or antigen-binding fragments may include a heavy chain CDR1 amino acid sequence substantially the same as, or identical to, SEQ ID NO: 30. In some embodiments, antibodies or antigen-binding fragments may include a heavy chain CDR2 amino acid sequence substantially the same as, or identical to, SEQ ID NO: 31. In some embodiments, antibodies or antigen-binding fragments may include a heavy chain CDR3 amino acid sequence substantially the same as, or identical to, SEQ ID NO: 32. The antibodies or antigen-binding fragments may include a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28. The antibodies or antigen-binding fragments may include a heavy chain having a CDR1 amino acid sequence substantially the same as, or identical to, SEQ ID NO: 30; a CDR2 amino acid sequence substantially the same as, or identical to, SEQ ID NO: 31; and a CDR3 amino acid sequence substantially the same as, or identical to, SEQ ID NO: 32. The antibodies or antigen-binding fragments may include a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28, and also have a heavy chain having a CDR1 amino acid sequence substantially the same as, or identical to, SEQ ID NO: 30; a CDR2 amino acid sequence substantially the same as, or identical to, SEQ ID NO: 31; and a CDR3 amino acid sequence substantially the same as, or identical to, SEQ ID NO: 32.

The described antibodies or antigen-binding fragments may include a light chain variable domain that includes an amino acid sequence substantially the same as, or identical to, SEQ ID NO: 29. In some embodiments, an isolated polynucleotide that includes a sequence substantially the same as, or identical to, SEQ ID NO: 61 may encode this light chain variable domain amino acid sequence. The described antibodies or antigen-binding fragments may include a heavy chain variable domain that includes an amino acid sequence substantially the same as, or identical to, SEQ ID NO: 33. In some embodiments, an isolated polynucleotide that includes a sequence substantially the same as, or identical to, SEQ ID NO: 65 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 29, and the heavy chain variable domain includes an amino acid sequence substantially the same as, or identical to, SEQ ID NO: 33. In some embodiments are provided the 26B3.F2 (26B3) antibody or antigen-binding fragments thereof, which is capable of binding to the native, nonreduced, or chemically preserved forms of FRα.

In some embodiments, the 26B3 antibody is produced by antibody-producing cells deposited with the American Type Culture Collection (10801 University Blvd., Manassas, Va. 20110-2209) on May 19, 2011 and have been assigned Accession No. PTA-11885. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are polynucleotides that encode antibodies or antigen-binding fragments that specifically bind to the native, nonreduced, or chemically preserved forms of FRα. In some embodiments, the isolated polynucleotides encode an antibody or antigen-binding fragment thereof having a light chain CDR1 sequence substantially the same as, or identical to, SEQ ID NO: 26, for example SEQ ID NO: 58. In some embodiments, the isolated polynucleotides encode an antibody or antigen-binding fragment thereof having a light chain CDR2 substantially the same as, or identical to, SEQ ID NO: 27, for example SEQ ID NO: 59. In some embodiments, the isolated polynucleotides encode an antibody or antigen-binding fragment thereof having a light chain CDR3 substantially the same as, or identical to, SEQ ID NO: 28, for example SEQ ID NO: 60. In some embodiments, the isolated polynucleotides encode an antibody or antigen-binding fragment thereof having a heavy chain CDR1 substantially the same as, or identical to, SEQ ID NO: 30, for example SEQ ID NO: 62. In some embodiments, the isolated polynucleotides encode an antibody or antigen-binding fragment thereof having a heavy chain CDR2 substantially the same as, or identical to, SEQ ID NO: 31, for example SEQ ID NO: 63. In some embodiments, the isolated polynucleotides encode an antibody or antigen-binding fragment thereof having a heavy chain CDR3 substantially the same as, or identical to, SEQ ID NO: 32, for example SEQ ID NO: 64. The polynucleotides may encode an antibody or antigen-binding fragment thereof having a light chain with a CDR1 substantially the same as, or identical to, SEQ ID NO: 26, for example SEQ ID NO: 58; a CDR2 substantially the same as, or identical to, SEQ ID NO: 27, for example SEQ ID NO: 59; and a CDR3 substantially the same as, or identical to, SEQ ID NO: 28, for example SEQ ID NO: 60. The polynucleotides may encode an antibody or antigen-binding fragment thereof having a heavy chain CDR1 substantially the same as, or identical to, SEQ ID NO: 30, for example SEQ ID NO: 62; a CDR2 substantially the same as, or identical to, SEQ ID NO: 31, for example SEQ ID NO: 63; and a CDR3 substantially the same as, or identical to, SEQ ID NO: 32, for example SEQ ID NO: 64. The polynucleotides may encode an antibody or antigen-binding fragment thereof having a light chain CDR1 substantially the same as, or identical to, SEQ ID NO: 26, for example SEQ ID NO: 58; a CDR2 encoded by a nucleotide sequence substantially the same as, or identical to, SEQ ID NO: 27, for example SEQ ID NO: 59; and a CDR3 encoded by a nucleotide sequence substantially the same as, or identical to, SEQ ID NO: 28, for example SEQ ID NO: 60; and a heavy chain CDR1 substantially the same as, or identical to, SEQ ID NO: 30, for example SEQ ID NO: 62; a CDR2 substantially the same as, or identical to, SEQ ID NO: 31, for example SEQ ID NO: 63; and a CDR3 substantially the same as, or identical to, SEQ ID NO: 32, for example SEQ ID NO: 64. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 29, for example SEQ ID NO: 61. In some embodiments the described polynucleotides may encode antibodies or antigen-binding fragments that have a heavy chain variable domain segment that includes an amino acid sequence substantially the same as, or identical to, SEQ ID NO: 33, for example SEQ ID NO: 65. In some embodiments the described polynucleotides may encode antibodies or antigen-binding fragments that have a light chain variable domain segment that includes an amino acid sequence substantially the same as, or identical to, SEQ ID NO: 29, for example SEQ ID NO: 61; and a heavy chain variable domain segment that includes an amino acid sequence substantially the same as, or identical to, SEQ ID NO: 33, for example SEQ ID NO: 65. The polynucleotides capable of encoding the variable domain segments provided herein may be included on the same, or different, vectors to produce an antibodies or antigen-binding fragments. Polynucleotides described herein may encode the 26B3 antibody or antigen-binding fragments thereof, capable of binding the native, nonreduced, or chemically preserved forms of FRα.

Vectors comprising the antibody- and antigen-binding fragment-encoding polynucleotides are provided, as are cells expressing the antibodies or antigen-binding fragments that specifically bind to FRα. Also provided are cells capable of expressing the described vectors. These cells may be mammalian cells (such as CHO—K1 cells), insect cells (such as Sf7 cells), yeast cells, plant cells, or bacteria cells (such as *E. coli*). The described antibodies may also be produced by hybridoma cells, as described herein.

Methods for Diagnosing Cancer

Provided herein are methods for diagnosing breast, thyroid, colorectal, endometrial, fallopian tube, ovarian or lung cancer of epithelial origin in a subject. In some embodiments the described methods involve assessing whether a subject is afflicted with FRα-expressing cancer by determining the level of FRα that is present in a sample derived from the subject; and comparing the observed level of FRα with the level of FRα in a control sample, wherein a difference between the level of FRα in the sample derived from the subject and the level of FRα in the control sample is an indication that the subject either is or is not afflicted with an FRα-expressing cancer.

In some embodiments the control sample may be derived from a subject that is not afflicted with FRα-expressing cancer. In some embodiments the control sample may be derived from a subject that is afflicted with FRα-expressing cancer. In some embodiments where the control sample is derived from a subject that is not afflicted with FRα-expressing cancer, an observed increase in the amount of FRα present in the sample, relative to that observed for the control sample, is an indication that the subject being assessed is afflicted with FRα-expressing cancer. In some embodiments where the control sample is derived from a subject that is not afflicted with FRα-expressing cancer, an observed decrease or similarity in the amount of FRα present in the test sample, relative to that observed for the control sample, is an indication that the subject being assessed is not afflicted with FRα-expressing cancer. In some embodiments where the control sample is derived from a subject that is afflicted with FRα-expressing cancer, an observed similarity in the amount of FRα present in the test sample, relative to that observed for the control sample, is an indication that the subject being assessed is afflicted with FRα-expressing cancer. In some embodiments where the control sample is derived from a subject that is afflicted with FRα-expressing cancer, an observed decrease in the amount of FRα present in the test sample, relative to that observed for the control sample, is an indication that the subject being assessed is not afflicted with FRα-expressing cancer.

In some embodiments the level of FRα in the sample derived from the subject is assessed by contacting the sample with an antibody that binds FRα, such as the antibodies described herein. Similar methods may be used to determine if a subject is afflicted with cancer that is not associated with increased FRα production. The sample assessed for the presence of FRα may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like.

In some embodiments the described methods involve assessing whether a subject is afflicted with FRα-expressing cancer by determining the level of FRα associated with a cell or tissue that is present in a sample derived from the subject; and comparing the observed level of FRα with the level of FRα in a control sample, wherein a difference between the level of FRα in the sample derived from the subject and the level of FRα in the control sample is an indication that the subject is afflicted with an FRα-expressing cancer. In some embodiments the level of FRα in the sample derived from the subject is assessed by contacting the sample with an antibody that binds FRα, such as the antibodies described herein. The sample assessed for the presence of FRα may be circulating cells, circulating tumor cells, cells that are not tissue associated (i.e., free cells), tissues (e.g., surgically resected tumor tissue, biopsies, including fine needle aspiration), histological preparations, and the like.

In some embodiments the described methods involve assessing whether a subject is afflicted with FRα-expressing cancer by determining the level of FRα that is not associated with a cell or tissue that is present in a sample derived from the subject; and comparing the observed level of FRα with the level of FRα in a control sample, wherein a difference between the level of FRα in the sample derived from the subject and the level of FRα in the control sample is an indication that the subject is afflicted with an FRα-expressing cancer. In some embodiments the level of FRα in the sample derived from the subject is assessed by contacting the sample with an antibody that binds FRα, such as the antibodies described herein. The sample assessed for the presence of FRα may be urine, blood, serum, plasma, saliva, ascites, histological preparations, and the like.

In various embodiments of the described methods, the cancer may be FRα-expressing cancer. In a particular embodiment, the FRα-expressing cancer is ovarian cancer. In some embodiments the FRα-expressing cancer is endometrial cancer. In some embodiments the FRα-expressing cancer is colorectal cancer. In some embodiments the FRα-expressing cancer is breast cancer. In some embodiments the FRα-expressing cancer is thyroid cancer. In some embodiments the FRα-expressing cancer is fallopian tube cancer. In another embodiment, the FRα-expressing cancer is non-small cell lung cancer, such as an adenocarcinoma. Alternatively, the described methods may be used to identify cancer that does not express FRα, such as squamous cell carcinoma. For example, the described methods could be used to distinguish a FRα-expressing lung cancer, such as adenocarcinoma, from a lung cancer that does not express FRα, such as squamous cell carcinoma. The described methods could be used to distinguish a FRα-expressing breast cancer, such as fibroadenoma, from breast cancer that does not express FRα, such as cystosarcoma. Furthermore, the described methods could be used to distinguish a FRα-expressing thyroid cancer, such as papillary carcinoma, from thyroid cancer that does not express FRα, such as medullary carcinoma. In some embodiments described herein detection of FRα-expressing cancer cells in a subject may be used to determine that the subject may be treated with a therapeutic agent directed against FRα. In some embodiments the therapeutic agent directed against FRα may be an antibody, such as Farletuzumab.

In various aspects, the level of FRα is determined by contacting the sample with an antibody, or antigen-binding fragment thereof, that binds FRα. In some embodiments, the sample may be contacted by more than one type of antibody, or antigen-binding fragment thereof, that binds FRα. In some embodiments, the sample may be contacted by a first antibody, or antigen-binding fragment thereof, that binds FRα and then contacted by a second antibody, or antigen-binding fragment thereof, that binds FRα. Antibodies such as those described herein may be used in this capacity. For example, the antibody is selected from the group consisting of:

(a) an antibody, or antigen-binding fragment thereof, that binds the same epitope as any one of antibody 9F3, antibody 19D4, antibody 24F12, or antibody 26B3;

(b) any one of antibody 9F3, antibody 19D4, antibody 24F12, or antibody 26B3, or an antigen-binding fragment thereof;

(c) an antibody, or antigen-binding fragment thereof, that comprises the heavy and light chain CDRs of any one of antibody 9F3, antibody 19D4, antibody 24F12, or antibody 26B3

(d) an antibody, or antigen-binding fragment thereof, that comprises the heavy chain variable domain segment and light chain variable domain segment of any one of antibody 9F3, antibody 19D4, antibody 24F12, or antibody 26B3, as described in Table 1; or (e) an antibody having the amino acid sequence of antibody produced by any one of the cell lines deposited with the ATCC having accession number PTA-11887, PTA-11884, PTA-11886, or PTA-11885, or an antigen binding fragment thereof.

In certain embodiments, the level of FRα is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In various embodiments of the foregoing aspects of the invention, the control sample is a standardized control level of FRα in a healthy subject. In other embodiments the control sample may be FRα protein at a known concentration (e.g., a recombinant or purified FRα protein sample). In some embodiments, the observed FRα-levels of the tested subject may be compared with FRα levels observed in samples from subjects known to have FRα-expressing cancer or known concentrations of FRα.

Methods for Monitoring Cancer

Provided herein are methods for monitoring FRα-expressing cancer in a subject. The described methods may be used before treatment for cancer, after treatment for cancer, or both before and after treatment for cancer. In some embodiments the described methods involve assessing whether FRα-expressing cancer is progressing, regressing, or remaining stable by determining the level of FRα that is present in a test sample derived from the subject; and comparing the observed level of FRα with the level of FRα in a sample obtained from the subject at an earlier point in time, wherein a difference between the level of FRα in the test sample and the earlier sample provides an indication of whether the cancer is progressing, regressing, or remaining stable. In this regard, a test sample with an increased level of FRα, relative to the levels observed for the earlier sample, may indicate progression of an FRα-expressing cancer. Conversely, a test sample with a decreased level of FRα, relative to the levels observed for the earlier sample, may indicate regression of an FRα-expressing cancer. Accordingly, a test sample with an insignificant difference in the level of FRα, relative to the levels observed for the earlier sample, may indicate a state of stable disease for an FRα-expressing cancer. In some embodiments the level of FRα in a sample derived from the subject is assessed by contacting the sample with an antibody that binds FRα, such as the antibodies described herein. The sample assessed for the presence of FRα may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like.

In some embodiments the described methods involve assessing whether FRα-expressing cancer is progressing, regressing, or remaining stable by determining the level of FRα associated with a cell or tissue that is present in a test sample derived from the subject; and comparing the observed level of FRα with the level of FRα in a sample obtained from the subject, in a similar manner, at an earlier point in time, wherein a difference between the level of FRα in the test sample and the earlier sample provides an indication of whether the cancer is progressing, regressing, or remaining stable. In this regard, a test sample with an increased level of FRα, relative to the levels observed for the earlier sample, may indicate progression of an FRα-expressing cancer. Conversely, a test sample with a decreased level of FRα, relative to the levels observed for the earlier sample, may indicate regression of an FRα-expressing cancer. Accordingly, a test sample with an insignificant difference in the level of FRα, relative to the levels observed for the earlier sample, may indicate a state of stable disease for an FRα-expressing cancer. In some embodiments the level of FRα in a sample derived from the subject is assessed by contacting the sample with an antibody that binds FRα, such as the antibodies described herein. The sample assessed for the presence of FRα may be circulating cells, circulating tumor cells, cells that are not tissue associated (i.e., free cells), tissues (e.g., surgically resected tumor tissue, biopsies, including fine needle aspiration), histological preparations, and the like.

In some embodiments the described methods involve assessing whether FRα-expressing cancer is progressing, regressing, or remaining stable by determining the level of FRα not associated with a cell or tissue that is present in a test sample derived from the subject; and comparing the observed level of FRα with the level of FRα in a sample obtained from the subject, in a similar manner, at an earlier point in time, wherein a difference between the level of FRα in the test sample and the earlier sample provides an indication of whether the cancer is progressing, regressing, or remaining stable. In this regard, a test sample with an increased level of FRα, relative to the levels observed for the earlier sample, may indicate progression of an FRα-expressing cancer. Conversely, a test sample with a decreased level of FRα, relative to the levels observed for the earlier sample, may indicate regression of an FRα-expressing cancer. Accordingly, a test sample with an insignificant difference in the level of FRα, relative to the levels observed for the earlier sample, may indicate a state of stable disease for an FRα-expressing cancer. In some embodiments the level of FRα in a sample derived from the subject is assessed by contacting the sample with an antibody that binds FRα, such as the antibodies described herein. The sample assessed for the presence of FRα may be urine, blood, serum, plasma, saliva, ascites, histological preparations, and the like.

In various embodiments of the described methods, the cancer may be FRα-expressing cancer. In a particular embodiment, the FRα-expressing cancer is ovarian cancer. In some embodiments the FRα-expressing cancer is endometrial cancer. In some embodiments the FRα-expressing cancer is colorectal cancer. In some embodiments the FRα-expressing cancer is breast cancer. In some embodiments the FRα-expressing cancer is thyroid cancer. In some embodiments the FRα-expressing cancer is fallopian tube cancer. In another embodiment, the FRα-expressing cancer is non-small cell lung cancer, such as an adenocarcinoma.

In various aspects, the level of FRα is determined by contacting the sample with an antibody, or antigen-binding fragment thereof, that binds FRα. In some embodiments, the sample may be contacted by more than one type of antibody, or antigen-binding fragment thereof, that binds FRα. In some embodiments, the sample may be contacted by a first antibody, or antigen-binding fragment thereof, that binds FRα and then contacted by a second antibody, or antigen-binding fragment thereof, that binds FRα. Antibodies such as those described herein may be used in this capacity. For example, the antibody is selected from the group consisting of:

(a) an antibody, or antigen-binding fragment thereof, that binds the same epitope as any one of antibody 9F3, antibody 19D4, antibody 24F12, or antibody 26B3;

(b) any one of antibody 9F3, antibody 19D4, antibody 24F12, or antibody 26B3, or an antigen-binding fragment thereof;

(c) an antibody, or antigen-binding fragment thereof, that comprises the heavy and light chain CDRs of any one of antibody 9F3, antibody 19D4, antibody 24F12, or antibody 26B3.

In certain embodiments, the level of FRα is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Additional aspects of the summarized subject matter are provided in greater detail in the detailed description and provided examples and associated figures.

BRIEF DESCRIPTION OF THE DRAWINGS

FIG. 2 illustrates amino acid residues of FRα (SEQ ID NO:1) that comprise the epitopes (shaded regions) for monoclonal antibodies 9F3, 24F12, and 26B3, as predicted by hydrogen/deuterium exchange mass spectrometry and docking methods.

FIG. 5 shows FRα expression in normal tissues. Normal lung (A) and kidney (B) samples stained with antibody 26B3 demonstrate that expression of FRα is highly restricted to epithelial cells and has a predominantly apical distribution (images are 20× magnification).

FIG. 7 shows FRα staining of histologic subtypes of non-small cell lung carcinoma: (A) lung adenocarcinoma at 20×, (B) lung adenocarcinoma at 40×, (C) lung adenosquamous at 20×, and (D) lung squamous cell carcinoma at 40×.

FIG. 17 shows FRα expression is limited to the luminal borders normal endometrium with weak 1+ and moderate 2+ intensity at 40× magnification (A). Strong (+3) membrane staining can be observed on the luminal borders of atypical complex hyperplasia at 20× magnification (B).

DETAILED DESCRIPTION OF ILLUSTRATIVE EMBODIMENTS

Figure 1:
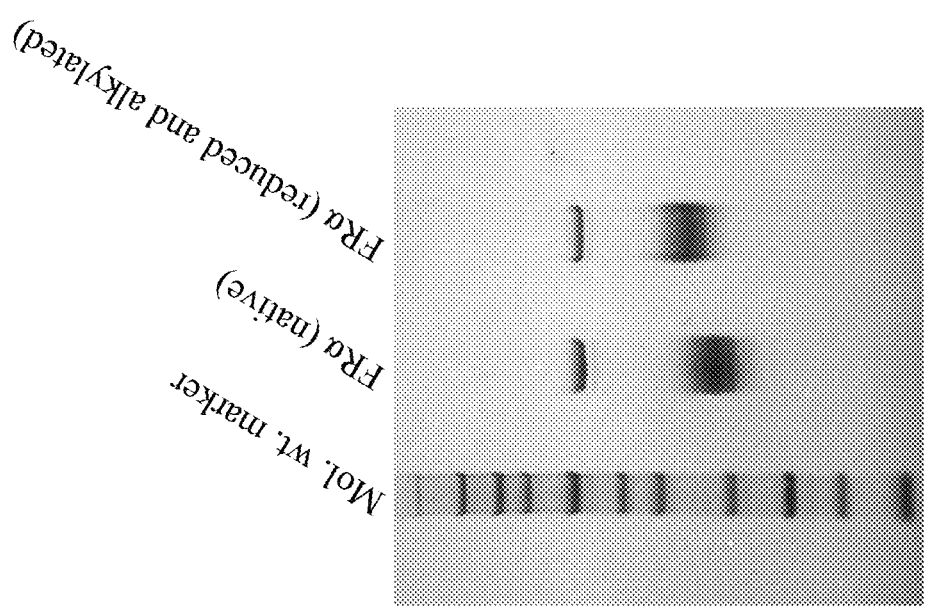
FIG. 1 depicts the migratory patterns of FRα by SDS-PAGE under nonreducing conditions. FRα was assessed in either native (lane 2) or reduced and alkylated (lane 3) form.

The following description characterizes antibodies, and antigen-binding fragments thereof, that specifically bind to FRα. Also described are related polynucleotides capable of encoding these antibodies, and antigen-binding fragments, cells expressing the antibodies, and antigen-binding fragments, as well as associated vectors and detectable antibody labels. In addition, methods of using the antibodies, and antigen-binding fragments, are described. For example, the provided antibodies, and antigen-binding fragments, may be used to diagnose ovarian, breast, thyroid, colorectal, endometrial, fallopian tube, or lung cancer; monitor ovarian, breast, thyroid, colorectal, endometrial, fallopian tube, or lung cancer progression, regression, or stable disease; to determine whether or not a patient should be treated for cancer, or to determine whether or not a subject is afflicted with FRα-expressing cancer and thus may be amenable to treatment with a FRα-specific anti-cancer therapeutic.

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

"Isolated" means a biological component (such as a nucleic acid, peptide or protein) has been substantially separated, produced apart from, or purified away from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins that can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. Such identity may be determined using nBLAST algorithm (Altschul et al., (1990) Proc. Natl. Acad. Sci. USA 87:2264-8; Karlin and Altschul (1993) Proc. Natl. Acad. Sci. USA 90:5873-7).

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described. Other embodiments include FRα specific antibodies, or antigen-binding fragments, that have framework, scaffold, or other non-binding regions that do not share significant identity with the antibodies and antigen-binding fragments described herein, but do incorporate one or more CDRs or other sequences needed to confer binding that are 90%, 91%, 92%, 93%, 94%, 95%, 96%, 97%, 98%, or 99° A identical to such sequences described herein.

A "vector" is a replicon, such as plasmid, phage, cosmid, or virus in which another nucleic acid segment may be operably inserted so as to bring about the replication or expression of the segment.

A cell has been "transformed" when exogenous or heterologous nucleic acids such as DNA have been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

"Antibody" refers to all isotypes of immunoglobulins (IgG, IgA, IgE, IgM, IgD, and IgY) including various monomeric and polymeric forms of each isotype, unless otherwise specified.

Antigen-binding fragments are any proteinaceous structure that may exhibit binding affinity for a particular antigen. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

"Specific binding" when used in the context of antibodies, or antibody fragments, represents binding via domains encoded by immunoglobulin genes or fragments of immunoglobulin genes to one or more epitopes of a protein of interest, but which do not substantially recognize and bind other molecules in a sample containing a mixed population of antigenic molecules. Typically, an antibody binds to a cognate antigen with a Kd of less than about $1 \times 10^{-8}$ M, as measured by a surface plasmon resonance assay or a cell binding assay.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

As used herein, the term "folate receptor alpha" (also referred to as FRα, FR-alpha, FOLR-1 or FOLR1) refers to the alpha isoform of the high affinity receptor for folate. Membrane bound FRα is attached to the cell surface by a glycosyl phosphatidylinositol (GPI) anchor. Soluble forms of FRα may be derived by the action of proteases or phospholipase on membrane anchored folate receptors. The amino acid sequence for human FRα is set forth herein as SEQ ID NO: 1. Variants, for example, naturally occurring allelic variants or sequences containing at least one amino acid substitution, are encompassed by the terms as used herein. As will be appreciated by those skilled in the art, cell associated and non-cell associated forms of human FRα may encompass variant forms of SEQ ID NO:1.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like.

Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

The term "progression," as used in the context of progression of an FRα-expressing cancer, includes the change of a cancer from a less severe to a more severe state. This could include an increase in the number or severity of tumors, the degree of metastasis, the speed with which the cancer is growing or spreading, and the like. For example, "the progression of ovarian cancer" includes the progression of such a cancer from a less severe to a more severe state, such as the progression from stage I to stage II, from stage II to stage III, etc.

The term "regression," as used in the context of regression of an FRα-expressing cancer, includes the change of a cancer from a more severe to a less severe state. This could include a decrease in the number or severity of tumors, the degree of metastasis, the speed with which the cancer is growing or spreading, and the like. For example, "the regression of ovarian cancer" includes the regression of such a cancer from a more severe to a less severe state, such as the progression from stage III to stage II, from stage II to stage I, etc.

The term "stable" as used in the context of stable FRα-expressing cancer, is intended to describe a disease condition that is not, or has not, changed significantly enough over a clinically relevant period of time to be considered a progressing cancer or a regressing cancer.

The embodiments described herein are not limited to particular methods, reagents, compounds, compositions or biological systems, which can, of course, vary.

FRα-Specific Antibodies and Antigen-Binding Fragments

Described herein are isolated monoclonal antibodies or antigen-binding fragments that specifically bind FRα. The general structure of an antibody molecule comprises an antigen binding domain, which includes heavy and light chains, and the Fc domain, which serves a variety of functions, including complement fixation and binding antibody receptors.

The described antibodies or antigen-binding fragments include all isotypes, IgA, IgD, IgE, IgG and IgM, and synthetic multimers of the four-chain immunoglobulin structure. The described antibodies or antigen-binding fragments also include the IgY isotype generally found in hen or turkey serum and hen or turkey egg yolk.

The antibodies or antigen-binding fragments disclosed in the examples section are derived from mice. Similar antibodies may be derived from any species by recombinant means. For example, the antibodies or antigen-binding fragments may be chimeric rat, goat, horse, swine, bovine, chicken, rabbit, camelid, donkey, human, and the like. For use in administration to humans, non-human derived antibodies or antigen-binding fragments may be genetically or structurally altered to be less antigenic upon administration to a human patient.

In some embodiments, the antibodies or antigen-binding fragments are chimeric. As used herein, the term "chimeric" refers to an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human. For example, a chimeric antibody may comprise a mouse antigen binding domain with a human Fc or other such structural domain.

In some embodiments, the antibodies are humanized antibodies. Humanized antibodies may be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may include at least a portion of an immunoglobulin constant region (Fc), typically that of a human immunoglobulin.

The antibodies or antigen-binding fragments described herein can occur in a variety of forms, but will include one or more of the antibody variable domain segments or CDRs shown in Table 1. The isotypes of the antibodies described in Table 1 are shown in parentheses to describe the constant region of each antibody, which are known to have conserved sequences.

TABLE 1

Antibody segments of the described antibodies and antigen-binding fragments thereof ("Lc" denotes light chain and "Hc" denotes heavy chain).

| Antibody Segment | SEQ ID NO. | Sequence |
|---|---|---|
| *Monoclonal antibody 9F3 (murine IgG2a constant region)* | | |
| Lc CDR1 | 2 | RASSTVSYSYLH |
| Lc CDR2 | 3 | GTSNLAS |
| Lc CDR3 | 4 | QQYSGYPLT |

TABLE 1-continued

Antibody segments of the described antibodies and antigen-binding fragments thereof ("Lc" denotes light chain and "Hc" denotes heavy chain).

| Antibody Segment | SEQ ID NO. | Sequence |
|---|---|---|
| Lc variable domain segment | 5 | PAIMSASPGEKVTMTCRASSTVSYSYLHWYQQ KSGASPQLWIYGTSNLASGVPARFSGSGSGTSY SLTISSVEAEDAATYYCQQYSGYPLTFGAGTKL ELKRADAAP |
| Hc CDR1 | 6 | SGYYWN |
| Hc CDR2 | 7 | YIKSDGSNNYNPSLKN |
| Hc CDR3 | 8 | EWKAMDY |
| Hc variable domain segment | 9 | ESGPGLVRPSQSLSLTCSVTGYSITS-GYYWNWIR QFPGSRLEWMGYIKSDGSNNYNPSLKNRISITR DTSKNQFFLKLNSVTTEDTATYFCTREWKAMD YWGQGTSVTVSSAKTTPPSVYPLAPGCGDT |
| *Monoclonal antibody 19D4 (murine IgG2a constant region)* | | |
| Lc CDR1 | 10 | RASESVDTYGNNFIH |
| Lc CDR2 | 11 | LASNLES |
| Lc CDR3 | 12 | QQNNGDPWT |
| Lc variable domain segment | 13 | PASLAVSLGQRATISCRASESVDTYGNNFIHWY QQKPGQPPKLLIYLASNLESGVPARF-SGSGSRTD FTLTIDPVEADDAATYYCQQNNGDPWTFGGGT KLEIKRADAAP |
| Hc CDR1 | 14 | HPYMH |
| Hc CDR2 | 15 | RIDPANGNTKYDPKFQG |
| Hc CDR3 | 16 | EEVADYTMDY |
| Hc variable domain segment | 17 | GAELVKPGASVKLSCTASGFNIKHPYMHWVKQ RPDQGLEWIGRIDPANGNTKYDPKFQGKATITA DTSSNTAYLQLSSLTSEDTAVYYCGREEVADYT MDYWGQGTSVTVSSAKTTAPSVYPLAPV |
| *Monoclonal antibody 24F12 murine IgG1 constant region)* | | |
| Lc CDR1 | 18 | SASQGINNFLN |
| Lc CDR2 | 19 | YTSSLHS |
| Lc CDR3 | 20 | QHFSKLPWT |
| Lc variable domain | 21 | TSSLSASLGDRVTISCSASQGINNFLNWYQQKP DGTVKLLIYYTSSLHSGVPSRFSGSGS-GTDYSLT ISNLEPEDIAIYYCQHFSKLPWT-FGGGTKLEIKR ADAAP |
| Hc CDR1 | 22 | SYAMS |
| Hc CDR2 | 23 | EIGSGGSYTYYPDTVTG |
| Hc CDR3 | 24 | ETTAGYFDY |
| Hc variable domain | 25 | SGGGLVRPGGSLKLSCAASGFTFSSYAMSWVR QSPEKRLEWVAEIGSGGSYTYYPDTVT-GRFTISR DNAKSTLYLEMSSLRSEDTAIYYCARETTAGYF DYWGQGTTLTVSS |
| *Monoclonal antibody 26B3 (murine IgG1 constant region)* | | |
| Lc CDR1 | 26 | RTSENIFSYLA |
| Lc CDR2 | 27 | NAKTLAE |
| Lc CDR3 | 28 | QHHYAFPWT |
| Lc variable domain segment | 29 | PASLSASVGETVTITCRTSENIFSYLAWYQQKQ GISPQLLVYNAKTLAEGVPSRFSGSGS-GTQFSLK INSLQPEDFGSYYCQHHYAFPWTFGGGSKLEIK RADAAP |
| Hc CDR1 | 30 | GYFMN |
| Hc CDR2 | 31 | RIFPYNGDTFYNQKFKG |
| Hc CDR3 | 32 | GTHYFDY |
| Hc variable domain segment | 33 | GPELVKPGASVKISCKASDYSFTGYFMNWVMQ SHGKSLEWIGRIFPYNGDTFYNQKFKGRATLTV DKSSSTAHMELRSLASEDSAVYFCARGTHYFD YWGQGTTLTVSSAKTTPPSVYPLAPGSAAQT |

TABLE 1-continued

Antibody segments of the described antibodies and antigen-binding fragments thereof ("Lc" denotes light chain and "Hc" denotes heavy chain).

| Antibody Segment | SEQ ID NO. | Sequence |
|---|---|---|
| Monoclonal antibody 9F3 (murine IgG2a constant region) | | |
| Lc CDR1 | 34 | AGGGCCAGCTCAACTGTAAGTTACAGTTACTTGCAC |
| Lc CDR2 | 35 | GGCACATCCAACTTGGCTTCT |
| Lc CDR3 | 36 | CAGCAGTACAGTGGTTACCCACTCACG |
| Lc variable domain segment | 37 | CCAGCAATCATGTCTGCATCTCCAGGGGAAAAGGTCACCATGACCTGCAGGGCCAGCTCAACTGTAAGTTACAGTTACTTGCACTGGTACCAGCAGAAGTCAGGTGCCTCCCCCAACTCTGGATTTATGGCACATCCAACTTGGCTTCTGGAGTCCCTGCTCGCTTCAGTGGCAGTGGGTCTGGGACCTCTTACTCTCTCACAATCAGCAGTGTGGAGGCTGAAGATGCTGCCACTTATTACTGCCAGCAGTACAGTGGTTACCCACTCACGTTCGGTGCTGGGACCAAGCTGGAGCTGAAACGGGCTGATGCTGCACCAAC |
| Hc CDR1 | 38 | AGTGGTTATTACTGGAAC |
| Hc CDR2 | 39 | TACATAAAGTCCGACGGTAGCAATAATTACAACCCATCTCTCAAAAAT |
| Hc CDR3 | 40 | GAGTGGAAGGCTATGGACTAC |
| Hc variable domain segment | 41 | GAGTCAGGACCTGGCCTCGTGAGACCTTCTCAGTCTCTGTCTCTCACCTGCTCTGTCACTGGCTACTCCATCACCAGTGGTTATTACTGGAACTGGATCCGGCAGTTTCCAGGAAGCAGACTGGAATGGATGGGCTACATAAAGTCCGACGGTAGCAATAATTACAACCCATCTCTCAAAAATCGAATCTCCATCACTCGTGACACATCTAAGAACCAGTTTTTCCTGAAGTTGAATTCTGTGACTACTGAGGACACAGCTACATATTTCTGTACAAGGGAGTGGAAGGCTATGGACTACTGGGGTCAGGGAACCTCAGTCACCGTCTCCTCAGCCAAAACAACACCCCCATCAGTCTATCCACTGGCCCTGGGTGTGGAGATACAAC |
| Monoclonal antibody 19D4 (murine IgG2a constant region) | | |
| Lc CDR1 | 42 | AGAGCCAGTGAAAGTGTTGATACTTATGGCAATAATTTTATACAC |
| Lc CDR2 | 43 | CTTGCATCCAACCTAGAATCT |
| Lc CDR3 | 44 | CAGCAAAATAATGGGGATCCGTGGACG |
| Lc variable domain segment | 45 | CCAGCTTCTTTGGCTGTGTCTCTAGGGCAGAGGGCCACCATATCCTGCAGAGCCAGTGAAAGTGTTGATACTTATGGCAATAATTTTATACACTGGTACCAGCAGAAACCAGGACAGCCACCCAAACTCCTCATTTATCTTGCATCCAACCTAGAATCTGGGGTCCCTGCCAGGTTCAGTGGCAGTGGGTCTAGGACAGACTTCACCCTCACCATTGATCCTGTGGAGGCTGATGATGCTGCAACCTATTACTGTCAGCAAAATAATGGGGATCCGTGGACGTTCGGTGGAGGCACCAAGCTGGAGATCAAACGGGCTGATGCTGCACCAA |
| Hc CDR1 | 46 | CACCCCTATATGCAC |
| Hc CDR2 | 47 | AGGATTGATCCTGCGAATGGTAATACTAAATATGACCCGAAGTTCCAGGGC |
| Hc CDR3 | 48 | GAGGAGGTGGCGGACTATACTATGGACTAC |
| Hc variable domain segment | 49 | GGGGCAGAGCTTGTGAAGCCAGGGGCCTCAGTCAAGTTGTCCTGCACAGCTTCTGGCTTCAACATTAAACACCCTATATGCACTGGGTGAAGCAGAGGCCTGACCAGGGCCTGGAGTGGATTGGAAGGATTGATCCTGCGAATGGTAATACTAAATATGACCCGAAGTTCCAGGGCAAGGCCACTATAACAGCAGACACATCCTCCAACACAGCCTACCTACAGCTCAGCAGCCTGACATCTGAGGACACTGCCGTCTATTACTGTGCTAGAGAGGAGGTGGCGGACTATACTATGGACTACTGGGGTCAAGGAACCTCAGTCACCGTCTCCTCAGCCAAAACAACAGCCCCATCGGTCTATCCACTGGCCCCTGTGTG |

TABLE 1-continued

Antibody segments of the described antibodies and antigen-binding fragments thereof ("Lc" denotes light chain and "Hc" denotes heavy chain).

| Antibody Segment | SEQ ID NO. | Sequence |
|---|---|---|
| Monoclonal antibody 24F12 (murine IgG1 constant region) | | |
| Lc CDR1 | 50 | AGTGCAAGTCAGGGCATTAACAATTTTTAAAC |
| Lc CDR2 | 51 | TACACATCAAGTTTACACTCA |
| Lc CDR3 | 52 | CAGCACTTTAGTAAGCTTCCGTGGACG |
| Lc variable domain segment | 53 | ACATCCTCCCTGTCTGCCTCTCTGGGAGACAGAGTCACCATCAGTTGCAGTGCAAGTCAGGGCATTAACAATTTTTTAAACTGGTATCAGCAGAAACCAGATGGCACTGTTAAACTCCTGATCTATTACACATCAAGTTTACACTCAGGAGTCCCATCAAGGTTCAGTGGCAGTGGGTCTGGGACAGATTATTCTCTCACCATCAGCAACCTGGAACCTGAAGATATTGCCATATACTATTGTCAGCACTTTAGTAAGCTTCCGTGGACGTTCGGTGGAGGCACCAAGCTGGAAATCAAACGGGCTGATGCTGCACCAAC |
| Hc CDR1 | 54 | AGCTATGCCATGTCT |
| Hc CDR2 | 55 | GAAATTGGTAGTGGTGGTAGTTACACCTACTATCCAGACACTGTGACGGGC |
| Hc CDR3 | 56 | GAAACTACGGCGGGCTACTTTGACTAC |
| Hc variable domain segment | 57 | TCTGGGGGAGGCTTAGTGAGGCCTGGAGGGTCCCTGAAACTCTCCTGTGCAGCCTCTGGATTCACTTTCAGTAGCTATGCCATGTCTTGGGTTCGCCAGTCTCCAGAGAAGAGGCTGGAGTGGGTCGCAGAAATTGGTAGTGGTGGTAGTTACACCTACTATCCAGACACTGTGACGGGCCGATTCACCATCTCCAGAGACAATGCCAAGAGCACCCTGTACCTGGAAATGAGCAGTCTGAGGTCTGAGGACACGGCCATCTATTACTGTCAAGGGAAACTACGGCGGGCTACTTTGACTACTGGGGCCAAGGCACCACTCTCACAGTCTCCTCA |
| Monoclonal antibody 26B3 (murine IgG1 constant region) | | |
| Lc CDR1 | 58 | CGAACAAGTGAGAATATTTTCAGTTATTTAGCA |
| Lc CDR2 | 59 | AATGCAAAAACCTTAGCAGAG |
| Lc CDR3 | 60 | CAACATCATTATGCTTTTCCGTGGACG |
| Lc variable domain segment | 61 | CCAGCCTCCCTATCTGCATCTGTGGGAGAAACTGTCACCATCACATGTCGAACAAGTGAGAATATTTTCAGTTATTTAGCATGGTATCAGCAGAAACAGGGAATATCCTCAGCTCCTGGTCTATAATGCAAAAACCTTAGCAGAGGGTGTGCCATCAAGGTTCAGTGGCAGTGGATCAGGCACACAGTTTTCTCTGAAGATCAACAGCCTGCAGCCTGAAGATTTTGGGAGTTATTACTGTCAACATCATTATGCTTTTCCGTGGACGTTCGGTGGAGGCTCCAAGCTGGAAATCAAACGGGCTGATGCTGCACCAAC |
| Hc CDR1 | 62 | GGCTACTTTATGAAC |
| Hc CDR2 | 63 | CGTATTTTTCCTTACAATGGTGATACTTTCTACAACCAGAAGTTCAAGGGC |
| Hc CDR3 | 64 | GGGACTCATTACTTTGACTAC |
| Hc variable domain segment | 65 | GGACCTGAGCTGGTGAAGCCTGGGGCTTCAGTGAAGATATCCTGCAAGGCTTCTGATTACTCTTTTACTGGCTACTTTATGAACTGGGTGATGCAGAGCCATGGAAAGAGCCTTGAGTGGATTGGACGTATTTTTCCTTACAATGGTGATACTTTCTACAACCAGAAGTTCAAGGGCAGGGCCACATTGACTGTAGACAAATCCTCTAGCACAGCCCATATGGAGCTCCGGAGCCTGGCATCTGAGGACTCTGCAGTCTATTTTTGTGCAAGAGGGACTCATTACTTTGACTACTGGGGCCAAGGCACCACTCTCACTGTCTCCTCAGCCAAAACGACACCCCCATCTGTCTATCCACTGGCCCCTGGATCTGCTGCCCAAACTAA |

Described herein are isolated antibodies and antigen-binding fragments that specifically bind to FRα. In some embodiments, the antibodies or antigen-binding fragments are murine IgG, or derivatives thereof. While the antibodies or antigen-binding fragments may be human, humanized, or chimeric, the antibodies or antigen-binding fragments exemplified herein are murine. In some embodiments, antibodies or antigen-binding fragments may include a light chain CDR1 amino acid sequence substantially the same as, or identical to, SEQ ID NO: 2. In some embodiments, antibodies or antigen-binding fragments may include a light chain CDR2 amino acid sequence substantially the same as, or identical to, SEQ ID NO: 3. In some embodiments, antibodies or antigen-binding fragments may include a light chain CDR3 amino acid sequence substantially the same as, or identical to, SEQ ID NO: 4. In some embodiments, antibodies or antigen-binding fragments may include a heavy chain CDR1 amino acid sequence substantially the same as, or identical to, SEQ ID NO: 6. In some embodiments, antibodies or antigen-binding fragments may include a heavy chain CDR2 amino acid sequence substantially the same as, or identical to, SEQ ID NO: 7. In some embodiments, antibodies or antigen-binding fragments may include a heavy chain CDR3 amino acid sequence substantially the same as, or identical to, SEQ ID NO: 8. The antibodies or antigen-binding fragments may include a light chain having a CDR1 amino acid sequence substantially the same as, or identical to, SEQ ID NO: 2; a CDR2 amino acid sequence substantially the same as, or identical to, SEQ ID NO: 3; and a CDR3 amino acid sequence substantially the same as, or identical to, SEQ ID NO: 4. The antibodies or antigen-binding fragments may include a heavy chain having a CDR1 amino acid sequence substantially the same as, or identical to, SEQ ID NO: 6; a CDR2 amino acid sequence substantially the same as, or identical to, SEQ ID NO: 7; and a CDR3 amino acid sequence substantially the same as, or identical to, SEQ ID NO: 8. The antibodies or antigen-binding fragments may include a light chain having a CDR1 amino acid sequence substantially the same as, or identical to, SEQ ID NO: 2; a CDR2 amino acid sequence substantially the same as, or identical to, SEQ ID NO: 3; and a CDR3 amino acid sequence substantially the same as, or identical to, SEQ ID NO: 4, and also have a heavy chain having a CDR1 amino acid sequence substantially the same as, or identical to, SEQ ID NO: 6; a CDR2 amino acid sequence substantially the same as, or identical to, SEQ ID NO: 7; and a CDR3 amino acid sequence substantially the same as, or identical to, SEQ ID NO: 8.

The described antibodies or antigen-binding fragments may include a light chain variable domain that includes an amino acid sequence substantially the same as, or identical to, SEQ ID NO: 5. In some embodiments, an isolated polynucleotide that includes a sequence substantially the same as, or identical to, SEQ ID NO: 37 may encode this light chain variable domain amino acid sequence. The described antibodies or antigen-binding fragments may include a heavy chain variable domain that includes an amino acid sequence substantially the same as, or identical to, SEQ ID NO: 9. In some embodiments, an isolated polynucleotide that includes a sequence substantially the same as, or identical to, SEQ ID NO: 41 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 5, and the heavy chain variable domain includes an amino acid sequence substantially the same as, or identical to, SEQ ID NO: 9.

In some embodiments, the antibodies are produced by antibody-producing cells deposited with the American Type Culture Collection (10801 University Blvd., Manassas, Va. 20110-2209) on May 19, 2011 and have been assigned Accession No. PTA-11887. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to FRα. In some embodiments, the isolated polynucleotides encode an antibody or antigen-binding fragment thereof having a light chain CDR1 sequence substantially the same as, or identical to, SEQ ID NO: 2, for example SEQ ID NO: 34. In some embodiments, the isolated polynucleotides encode an antibody or antigen-binding fragment thereof having a light chain CDR2 substantially the same as, or identical to, SEQ ID NO: 3, for example SEQ ID NO: 35. In some embodiments, the isolated polynucleotides encode an antibody or antigen-binding fragment thereof having a light chain CDR3 substantially the same as, or identical to, SEQ ID NO: 4, for example SEQ ID NO: 36. In some embodiments, the isolated polynucleotides encode an antibody or antigen-binding fragment thereof having a heavy chain CDR1 substantially the same as, or identical to, SEQ ID NO: 6, for example SEQ ID NO: 38. In some embodiments, the isolated polynucleotides encode an antibody or antigen-binding fragment thereof having a heavy chain CDR2 substantially the same as, or identical to, SEQ ID NO: 7, for example SEQ ID NO: 39. In some embodiments, the isolated polynucleotides encode an antibody or antigen-binding fragment thereof having a heavy chain CDR3 substantially the same as, or identical to, SEQ ID NO: 8, for example SEQ ID NO: 40. The isolated polynucleotides may encode an antibody or antigen-binding fragment thereof having a light chain with a CDR1 substantially the same as, or identical to, SEQ ID NO: 2, for example SEQ ID NO: 34; a CDR2 substantially the same as, or identical to, SEQ ID NO: 3, for example SEQ ID NO: 35; and a CDR3 substantially the same as, or identical to, SEQ ID NO: 4, for example SEQ ID NO: 36. The isolated polynucleotides may encode an antibody or antigen-binding fragment thereof having a heavy chain CDR1 substantially the same as, or identical to, SEQ ID NO: 6, for example SEQ ID NO: 38; a CDR2 substantially the same as, or identical to, SEQ ID NO: 7, for example SEQ ID NO: 39; and a CDR3 substantially the same as, or identical to, SEQ ID NO: 8, for example SEQ ID NO: 40. The isolated polynucleotides may encode an antibody or antigen-binding fragment thereof having a light chain CDR1 substantially the same as, or identical to, SEQ ID NO: 2, for example SEQ ID NO: 34; a CDR2 encoded by a nucleotide sequence substantially the same as, or identical to, SEQ ID NO: 3, for example SEQ ID NO: 35; and a CDR3 encoded by a nucleotide sequence substantially the same as, or identical to, SEQ ID NO: 4, for example SEQ ID NO: 36; and a heavy chain CDR1 substantially the same as, or identical to, SEQ ID NO: 6, for example SEQ ID NO: 38; a CDR2 substantially the same as, or identical to, SEQ ID NO: 7, for example SEQ ID NO: 39; and a CDR3 substantially the same as, or identical to, SEQ ID NO: 8, for example SEQ ID NO: 40. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 5, for example SEQ ID NO: 37. In some embodiments the described isolated polynucleotides may encode antibodies or antigen-binding fragments that have a heavy chain variable domain segment that includes an amino acid sequence substantially the same as, or identical to, SEQ ID NO: 9, for example SEQ ID NO: 41. In some embodiments the described isolated polynucleotides may encode antibodies or antigen-binding fragments that have a light chain variable domain segment that includes an amino acid sequence substantially the same as, or identical to, SEQ ID NO: 5, for example SEQ ID NO: 37; and a heavy chain variable domain segment that includes an amino acid sequence substantially the same as, or identical to, SEQ ID NO: 9, for example SEQ ID NO: 41. The isolated polynucleotides capable of encoding the variable domain segments provided herein may be included on the same, or different, vectors to produce antibodies or antigen-binding fragments.

Described herein are isolated antibodies and antigen-binding fragments that specifically bind to FRα. In some embodiments, the antibodies or antigen-binding fragments are murine IgG, or derivatives thereof. While the antibodies or antigen-binding fragments may be human, humanized, or chimeric, the antibodies or antigen-binding fragments exemplified herein are murine. In some embodiments, antibodies or antigen-binding fragments may include a light chain CDR1 amino acid sequence substantially the same as, or identical to, SEQ ID NO: 10. In some embodiments, antibodies or antigen-binding fragments may include a light chain CDR2 amino acid sequence substantially the same as, or identical to, SEQ ID NO: 11. In some embodiments, antibodies or antigen-binding fragments may include a light chain CDR3 amino acid sequence substantially the same as, or identical to, SEQ ID NO: 12. In some embodiments, antibodies or antigen-binding fragments may include a heavy chain CDR1 amino acid sequence substantially the same as, or identical to, SEQ ID NO: 14. In some embodiments, antibodies or antigen-binding fragments may include a heavy chain CDR2 amino acid sequence substantially the same as, or identical to, SEQ ID NO: 15. In some embodiments, antibodies or antigen-binding fragments may include a heavy chain CDR3 amino acid sequence substantially the same as, or identical to, SEQ ID NO: 16. The antibodies or antigen-binding fragments may include a light chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12. The antibodies or antigen-binding fragments may include a heavy chain having a CDR1 amino acid sequence substantially the same as, or identical to, SEQ ID NO: 14; a CDR2 amino acid sequence substantially the same as, or identical to, SEQ ID NO: 15; and a CDR3 amino acid sequence substantially the same as, or identical to, SEQ ID NO: 16. The antibodies or antigen-binding fragments may include a light chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12, and also have a heavy chain having a CDR1 amino acid sequence substantially the same as, or identical to, SEQ ID NO: 14; a CDR2 amino acid sequence substantially the same as, or identical to, SEQ ID NO: 15; and a CDR3 amino acid sequence substantially the same as, or identical to, SEQ ID NO: 16.

The described antibodies or antigen-binding fragments may include a light chain variable domain that includes an amino acid sequence substantially the same as, or identical to, SEQ ID NO: 13. In some embodiments, an isolated polynucleotide that includes a sequence substantially the same as, or identical to, SEQ ID NO: 45 may encode this light chain variable domain amino acid sequence. The described antibodies or antigen-binding fragments may include a heavy chain variable domain that includes an amino acid sequence substantially the same as, or identical to, SEQ ID NO: 17. In some embodiments, an isolated polynucleotide that includes a sequence substantially the same as, or identical to, SEQ ID NO: 49 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 13, and the heavy chain variable domain includes an amino acid sequence substantially the same as, or identical to, SEQ ID NO: 17.

In some embodiments, the antibodies are produced by antibody-producing cells deposited with the American Type Culture Collection (10801 University Blvd., Manassas, Va. 20110-2209) on May 19, 2011 and have been assigned Accession No. PTA-11884. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are isolated polynucleotides that encode antibodies or antigen-binding fragments that specifically bind to FRα. In some embodiments, the isolated polynucleotides encode an antibody or antigen-binding fragment thereof having a light chain CDR1 sequence substantially the same as, or identical to, SEQ ID NO: 10, for example SEQ ID NO: 42. In some embodiments, the isolated polynucleotides encode an antibody or antigen-binding fragment thereof having a light chain CDR2 substantially the same as, or identical to, SEQ ID NO: 11, for example SEQ ID NO: 43. In some embodiments, the isolated polynucleotides encode an antibody or antigen-binding fragment thereof having a light chain CDR3 substantially the same as, or identical to, SEQ ID NO: 12, for example SEQ ID NO: 44. In some embodiments, the isolated polynucleotides encode an antibody or antigen-binding fragment thereof having a heavy chain CDR1 substantially the same as, or identical to, SEQ ID NO: 14, for example SEQ ID NO: 46. In some embodiments, the isolated polynucleotides encode an antibody or antigen-binding fragment thereof having a heavy chain CDR2 substantially the same as, or identical to, SEQ ID NO: 15, for example SEQ ID NO: 47. In some embodiments, the isolated polynucleotides encode an antibody or antigen-binding fragment thereof having a heavy chain CDR3 substantially the same as, or identical to, SEQ ID NO: 16, for example SEQ ID NO: 48. The polynucleotides may encode an antibody or antigen-binding fragment thereof having a light chain with a CDR1 substantially the same as, or identical to, SEQ ID NO: 10, for example SEQ ID NO: 42; a CDR2 substantially the same as, or identical to, SEQ ID NO: 11, for example SEQ ID NO: 43; and a CDR3 substantially the same as, or identical to, SEQ ID NO: 12, for example SEQ ID NO: 44. The polynucleotides may encode an antibody or antigen-binding fragment thereof having a heavy chain CDR1 substantially the same as, or identical to, SEQ ID NO: 14, for example SEQ ID NO: 46; a CDR2 substantially the same as, or identical to, SEQ ID NO: 15, for example SEQ ID NO: 47; and a CDR3 substantially the same as, or identical to, SEQ ID NO: 16, for example SEQ ID NO: 48. The polynucleotides may encode an antibody or antigen-binding fragment thereof having a light chain CDR1 substantially the same as, or identical to, SEQ ID NO: 10, for example SEQ ID NO: 42; a CDR2 encoded by a nucleotide sequence substantially the same as, or identical to, SEQ ID NO: 11, for example SEQ ID NO: 43; and a CDR3 encoded by a nucleotide sequence substantially the same as, or identical to, SEQ ID NO: 12, for example SEQ ID NO: 44; and a heavy chain CDR1 substantially the same as, or identical to, SEQ ID NO: 14, for example SEQ ID NO: 46; a CDR2 substantially the same as, or identical to, SEQ ID NO: 15, for example SEQ ID NO: 47; and a CDR3 substantially the same as, or identical to, SEQ ID NO: 16, for example SEQ ID NO: 48. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 13, for example SEQ ID NO: 45. In some embodiments the described polynucleotides may encode antibodies or antigen-binding fragments that have a heavy chain variable domain segment that includes an amino acid sequence substantially the same as, or identical to, SEQ ID NO: 17, for example SEQ ID NO: 49. In some embodiments the described polynucleotides may encode antibodies or antigen-binding fragments that have a light chain variable domain segment that includes an amino acid sequence substantially the same as, or identical to, SEQ ID NO: 13, for example SEQ ID NO: 45; and a heavy chain variable domain segment that includes an amino acid sequence substantially the same as, or identical to, SEQ ID NO: 17, for example SEQ ID NO: 49. The polynucleotides capable of encoding the variable domain segments provided herein may be included on the same, or different, vectors to produce antibodies or antigen-binding fragments.

Described herein are isolated antibodies and antigen-binding fragments that specifically bind to FRα. In some embodiments, the antibodies or antigen-binding fragments are murine IgG, or derivatives thereof. While the antibodies or antigen-binding fragments may be human, humanized, or chimeric, the antibodies or antigen-binding fragments exemplified herein are murine. In some embodiments, antibodies or antigen-binding fragments may include a light chain CDR1 amino acid sequence substantially the same as, or identical to, SEQ ID NO: 18. In some embodiments, antibodies or antigen-binding fragments may include a light chain CDR2 amino acid sequence substantially the same as, or identical to, SEQ ID NO: 19. In some embodiments, antibodies or antigen-binding fragments may include a light chain CDR3 amino acid sequence substantially the same as, or identical to, SEQ ID NO: 20. In some embodiments, antibodies or antigen-binding fragments may include a heavy chain CDR1 amino acid sequence substantially the same as, or identical to, SEQ ID NO: 22. In some embodiments, antibodies or antigen-binding fragments may include a heavy chain CDR2 amino acid sequence substantially the same as, or identical to, SEQ ID NO: 23. In some embodiments, antibodies or antigen-binding fragments may include a heavy chain CDR3 amino acid sequence substantially the same as, or identical to, SEQ ID NO: 24. The antibodies or antigen-binding fragments may include a light chain having a CDR1 amino acid sequence substantially the same as, or identical to, SEQ ID NO: 18; a CDR2 amino acid sequence substantially the same as, or identical to, SEQ ID NO: 19; and a CDR3 amino acid sequence substantially the same as, or identical to, SEQ ID NO: 20. The antibodies or antigen-binding fragments may include a heavy chain having a CDR1 amino acid sequence substantially the same as, or identical to, SEQ ID NO: 22; a CDR2 amino acid sequence substantially the same as, or identical to, SEQ ID NO: 23; and a CDR3 amino acid sequence substantially the same as, or identical to, SEQ ID NO: 24. The antibodies or antigen-binding fragments may include a light chain having a CDR1 amino acid sequence substantially the same as, or identical to, SEQ ID NO: 18; a CDR2 amino acid sequence substantially the same as, or identical to, SEQ ID NO: 19; and a CDR3 amino acid sequence substantially the same as, or identical to, SEQ ID NO: 20, and also have a heavy chain having a CDR1 amino acid sequence substantially the same as, or identical to, SEQ ID NO: 22; a CDR2 amino acid sequence substantially the same as, or identical to, SEQ ID NO: 23; and a CDR3 amino acid sequence substantially the same as, or identical to, SEQ ID NO: 24.

The described antibodies or antigen-binding fragments may include a light chain variable domain that includes an amino acid sequence substantially the same as, or identical to, SEQ ID NO: 21. In some embodiments, an isolated polynucleotide that includes a sequence substantially the same as, or identical to, SEQ ID NO: 53 may encode this light chain variable domain amino acid sequence. The described antibodies or antigen-binding fragments may include a heavy chain variable domain that includes an amino acid sequence substantially the same as, or identical to, SEQ ID NO: 25. In some embodiments, an isolated polynucleotide that includes a sequence substantially the same as, or identical to, SEQ ID NO: 57 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 21, and the heavy chain variable domain includes an amino acid sequence substantially the same as, or identical to, SEQ ID NO: 25.

In some embodiments, the antibodies are produced by antibody-producing cells deposited with the American Type Culture Collection (10801 University Blvd., Manassas, Va. 20110-2209) on May 19, 2011 and have been assigned Accession No. PTA-11886. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are polynucleotides that encode antibodies or antigen-binding fragments that specifically bind to FRα. In some embodiments, the isolated polynucleotides encode an antibody or antigen-binding fragment thereof having a light chain CDR1 sequence substantially the same as, or identical to, SEQ ID NO: 18, for example SEQ ID NO: 50. In some embodiments, the isolated polynucleotides encode an antibody or antigen-binding fragment thereof having a light chain CDR2 substantially the same as, or identical to, SEQ ID NO: 19, for example SEQ ID NO: 51. In some embodiments, the isolated polynucleotides encode an antibody or antigen-binding fragment thereof having a light chain CDR3 substantially the same as, or identical to, SEQ ID NO: 20, for example SEQ ID NO: 52. In some embodiments, the isolated polynucleotides encode an antibody or antigen-binding fragment thereof having a heavy chain CDR1 substantially the same as, or identical to, SEQ ID NO: 22, for example SEQ ID NO: 54. In some embodiments, the isolated polynucleotides encode an antibody or antigen-binding fragment thereof having a heavy chain CDR2 substantially the same as, or identical to, SEQ ID NO: 23, for example SEQ ID NO: 55. In some embodiments, the isolated polynucleotides encode an antibody or antigen-binding fragment thereof having a heavy chain CDR3 substantially the same as, or identical to, SEQ ID NO: 24, for example SEQ ID NO: 56. The polynucleotides may encode an antibody or antigen-binding fragment thereof having a light chain with a CDR1 substantially the same as, or identical to, SEQ ID NO: 18, for example SEQ ID NO: 50; a CDR2 substantially the same as, or identical to, SEQ ID NO: 19, for example SEQ ID NO: 51; and a CDR3 substantially the same as, or identical to, SEQ ID NO: 20, for example SEQ ID NO: 52. The polynucleotides may encode an antibody or antigen-binding fragment thereof having a heavy chain CDR1 substantially the same as, or identical to, SEQ ID NO: 22, for example SEQ ID NO: 54; a CDR2 substantially the same as, or identical to, SEQ ID NO: 23, for example SEQ ID NO: 55; and a CDR3 substantially the same as, or identical to, SEQ ID NO: 24, for example SEQ ID NO: 56. The polynucleotides may encode an antibody or antigen-binding fragment thereof having a light chain CDR1 substantially the same as, or identical to, SEQ ID NO: 18, for example SEQ ID NO: 50; a CDR2 encoded by a nucleotide sequence substantially the same as, or identical to, SEQ ID NO: 19, for example SEQ ID NO: 51; and a CDR3 encoded by a nucleotide sequence substantially the same as, or identical to, SEQ ID NO: 20, for example SEQ ID NO: 52; and a heavy chain CDR1 substantially the same as, or identical to, SEQ ID NO: 22, for example SEQ ID NO: 54; a CDR2 substantially the same as, or identical to, SEQ ID NO: 23, for example SEQ ID NO: 55; and a CDR3 substantially the same as, or identical to, SEQ ID NO: 24, for example SEQ ID NO: 56. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 21, for example SEQ ID NO: 53. In some embodiments the described polynucleotides may encode antibodies or antigen-binding fragments that have a heavy chain variable domain segment that includes an amino acid sequence substantially the same as, or identical to, SEQ ID NO: 25, for example SEQ ID NO: 57. In some embodiments the described polynucleotides may encode antibodies or antigen-binding fragments that have a light chain variable domain segment that includes an amino acid sequence substantially the same as, or identical to, SEQ ID NO: 21, for example SEQ ID NO: 53; and a heavy chain variable domain segment that includes an amino acid sequence substantially the same as, or identical to, SEQ ID NO: 25, for example SEQ ID NO: 57. The polynucleotides capable of encoding the variable domain segments provided herein may be included on the same, or different, vectors to produce antibodies or antigen-binding fragments.

Described herein are isolated antibodies and antigen-binding fragments that specifically bind to FRα. In some embodiments, the antibodies or antigen-binding fragments are murine IgG, or derivatives thereof. While the antibodies or antigen-binding fragments may be human, humanized, or chimeric, the antibodies or antigen-binding fragments exemplified herein are murine. In some embodiments, antibodies or antigen-binding fragments may include a light chain CDR1 amino acid sequence substantially the same as, or identical to, SEQ ID NO: 26. In some embodiments, antibodies or antigen-binding fragments may include a light chain CDR2 amino acid sequence substantially the same as, or identical to, SEQ ID NO: 27. In some embodiments, antibodies or antigen-binding fragments may include a light chain CDR3 amino acid sequence substantially the same as, or identical to, SEQ ID NO: 28. In some embodiments, antibodies or antigen-binding fragments may include a heavy chain CDR1 amino acid sequence substantially the same as, or identical to, SEQ ID NO: 30. In some embodiments, antibodies or antigen-binding fragments may include a heavy chain CDR2 amino acid sequence substantially the same as, or identical to, SEQ ID NO: 31. In some embodiments, antibodies or antigen-binding fragments may include a heavy chain CDR3 amino acid sequence substantially the same as, or identical to, SEQ ID NO: 32. The antibodies or antigen-binding fragments may include a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28. The antibodies or antigen-binding fragments may include a heavy chain having a CDR1 amino acid sequence substantially the same as, or identical to, SEQ ID NO: 30; a CDR2 amino acid sequence substantially the same as, or identical to, SEQ ID NO: 31; and a CDR3 amino acid sequence substantially the same as, or identical to, SEQ ID NO: 32. The antibodies or antigen-binding fragments may include a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28, and also have a heavy chain having a CDR1 amino acid sequence substantially the same as, or identical to, SEQ ID NO: 30; a CDR2 amino acid sequence substantially the same as, or identical to, SEQ ID NO: 31; and a CDR3 amino acid sequence substantially the same as, or identical to, SEQ ID NO: 32.

The described antibodies or antigen-binding fragments may include a light chain variable domain that includes an amino acid sequence substantially the same as, or identical to, SEQ ID NO: 29. In some embodiments, an isolated polynucleotide that includes a sequence substantially the same as, or identical to, SEQ ID NO: 61 may encode this light chain variable domain amino acid sequence. The described antibodies or antigen-binding fragments may include a heavy chain variable domain that includes an amino acid sequence substantially the same as, or identical to, SEQ ID NO: 33. In some embodiments, an isolated polynucleotide that includes a sequence substantially the same as, or identical to, SEQ ID NO: 65 may encode this heavy chain variable domain amino acid sequence. The described antibodies or antigen-binding fragments may include a light and a heavy chain variable domains, wherein the light chain variable domain includes an amino acid sequence substantially the same as, or identical to, SEQ ID NO: 29, and the heavy chain variable domain includes an amino acid sequence substantially the same as, or identical to, SEQ ID NO: 33.

In some embodiments, the antibodies are produced by antibody-producing cells deposited with the American Type Culture Collection (10801 University Blvd., Manassas, Va. 20110-2209) on May 19, 2011 and have been assigned Accession No. PTA-11885. In some embodiments, the antibodies, or antigen-binding fragments thereof, have the binding affinity for FRα of the antibodies produced by the deposited antibody-producing cells. In some embodiments, the disclosed antibodies, or antigen-binding fragments thereof, comprise the light and heavy chain CDRs of the antibodies produced by the deposited antibody-producing cells. In some embodiments, the antibodies, or antigen-binding fragments thereof, comprise the light and heavy chain variable regions of the antibodies produced by the deposited antibody-producing cells.

Also disclosed are polynucleotides that encode antibodies or antigen-binding fragments that specifically bind to FRα. In some embodiments, the isolated polynucleotides encode an antibody or antigen-binding fragment thereof having a light chain CDR1 sequence substantially the same as, or identical to, SEQ ID NO: 26, for example SEQ ID NO: 58. In some embodiments, the isolated polynucleotides encode an antibody or antigen-binding fragment thereof having a light chain CDR2 substantially the same as, or identical to, SEQ ID NO: 27, for example SEQ ID NO: 59. In some embodiments, the isolated polynucleotides encode an antibody or antigen-binding fragment thereof having a light chain CDR3 substantially the same as, or identical to, SEQ ID NO: 28, for example SEQ ID NO: 60. In some embodiments, the isolated polynucleotides encode an antibody or antigen-binding fragment thereof having a heavy chain CDR1 substantially the same as, or identical to, SEQ ID NO: 30, for example SEQ ID NO: 62. In some embodiments, the isolated polynucleotides encode an antibody or antigen-binding fragment thereof having a heavy chain CDR2 substantially the same as, or identical to, SEQ ID NO: 31, for example SEQ ID NO: 63. In some embodiments, the isolated polynucleotides encode an antibody or antigen-binding fragment thereof having a heavy chain CDR3 substantially the same as, or identical to, SEQ ID NO: 32, for example SEQ ID NO: 64. The polynucleotides may encode an antibody or antigen-binding fragment thereof having a light chain with a CDR1 substantially the same as, or identical to, SEQ ID NO: 26, for example SEQ ID NO: 58; a CDR2 substantially the same as, or identical to, SEQ ID NO: 27, for example SEQ ID NO: 59; and a CDR3 substantially the same as, or identical to, SEQ ID NO: 28, for example SEQ ID NO: 60. The polynucleotides may encode an antibody or antigen-binding fragment thereof having a heavy chain CDR1 substantially the same as, or identical to, SEQ ID NO: 30, for example SEQ ID NO: 62; a CDR2 substantially the same as, or identical to, SEQ ID NO: 31, for example SEQ ID NO: 63; and a CDR3 substantially the same as, or identical to, SEQ ID NO: 32, for example SEQ ID NO: 64. The polynucleotides may encode an antibody or antigen-binding fragment thereof having a light chain CDR1 substantially the same as, or identical to, SEQ ID NO: 26, for example SEQ ID NO: 58; a CDR2 encoded by a nucleotide sequence substantially the same as, or identical to, SEQ ID NO: 27, for example SEQ ID NO: 59; and a CDR3 encoded by a nucleotide sequence substantially the same as, or identical to, SEQ ID NO: 28, for example SEQ ID NO: 60; and a heavy chain CDR1 substantially the same as, or identical to, SEQ ID NO: 30, for example SEQ ID NO: 62; a CDR2 substantially the same as, or identical to, SEQ ID NO: 31, for example SEQ ID NO: 63; and a CDR3 substantially the same as, or identical to, SEQ ID NO: 32, for example SEQ ID NO: 64. Antigen-binding arrangements of CDRs may also be engineered using antibody-like proteins as CDR scaffolding. Such engineered antigen-binding proteins are within the scope of the disclosure.

Polynucleotides described herein may encode antibodies or antigen-binding fragments that have a light chain variable domain segment that includes an amino acid sequence substantially the same as, or identical to, SEQ ID NO: 29, for example SEQ ID NO: 61. In some embodiments the described polynucleotides may encode antibodies or antigen-binding fragments that have a heavy chain variable domain segment that includes an amino acid sequence substantially the same as, or identical to, SEQ ID NO: 33, for example SEQ ID NO: 65. In some embodiments the described polynucleotides may encode antibodies or antigen-binding fragments that have a light chain variable domain segment that includes an amino acid sequence substantially the same as, or identical to, SEQ ID NO: 29, for example SEQ ID NO: 61; and a heavy chain variable domain segment that includes an amino acid sequence substantially the same as, or identical to, SEQ ID NO: 33, for example SEQ ID NO: 65. The polynucleotides capable of encoding the variable domain segments provided herein may be included on the same, or different, vectors to produce antibodies or antigen-binding fragments.

Polynucleotides encoding engineered antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

The antibodies or antigen-binding fragments described herein include variants having single or multiple amino acid substitutions, deletions, or additions that retain the biological properties (e.g., binding affinity or immune effector activity) of the described antibodies or antigen-binding fragments. The skilled person may produce variants having single or multiple amino acid substitutions, deletions, or additions. These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art.

The antibodies or antigen-binding fragments described herein may embody several antibody isotypes, such as IgM, IgD, IgG, IgA and IgE. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments The antibodies or antigen-binding fragments described herein have binding affinities (in M) for FRα that include a dissociation constant ($K_D$) of less than about $1\times10^{-8}$ M. In one embodiment the antibody 9F3 has an affinity for FRα of $7.15\times10^{-10}$ M. In one embodiment the antibody 19D4 has an affinity for FRα of $5.67\times10^{-10}$ M. In one embodiment the antibody 24F12 has an affinity for FRα of $1.02\times10^{-10}$ M. In one embodiment the antibody 26B3 has an affinity for FRα of $2.73\times10^{-11}$ M. In one embodiment the antibody 9F3 has an affinity for FRα of about $6.5\times10^{-10}$ M to about $8\times10^{-10}$ M. In one embodiment the antibody 19D4 has an affinity for FRα of about $5\times10^{-10}$ M to about $6.5\times10^{-10}$ M. In one embodiment the antibody 24F12 has an affinity for FRα of about $0.5\times10^{-10}$ M to about $2\times10^{-10}$ M. In one embodiment the antibody 26B3 has an affinity for FRα of about $1\times10^{-11}$ M to about $3.5\times10^{-11}$ M.

Also provided are vectors comprising the polynucleotides described herein. The vectors can be expression vectors. Recombinant expression vectors containing a sequence encoding a polypeptide of interest are thus contemplated as within the scope of this disclosure. The expression vector may contain one or more additional sequences such as but not limited to regulatory sequences (e.g., promoter, enhancer), a selection marker, and a polyadenylation signal. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 *Mol. Cell. Biol.* 280 (1983).

In some embodiments, the antibody- or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate sythase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate antibody or antigen-binding fragment-producing cells. Thus, another aspect features host cells transformed with vectors comprising a nucleic acid sequence encoding an antibody or antigen-binding fragment thereof that specifically binds FRα, such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 *Pharmac. Ther.* 69-92 (1985)). Calcium phosphate precipitation and polyethylene glycol (PEG)-induced fusion of bacterial protoplasts with mammalian cells may also be used to transform cells.

Cells suitable for use in the expression of the antibodies or antigen-binding fragments described herein are preferably eukaryotic cells, more preferably cells of plant, rodent, or human origin, for example but not limited to NSO, CHO, CHOK1, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Provided herein are methods for detecting FRα in a sample by contacting the sample with an antibody, or antigen-binding fragment thereof, described herein. As described herein, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the described methods include detecting FRα in a sample by contacting the sample with:

(a) an antibody, or antigen-binding fragment thereof, that binds the same epitope as any one of antibody 9F3, antibody 19D4, antibody 24F12, or antibody 26B3;

(b) any one of antibody 9F3, antibody 19D4, antibody 24F12, or antibody 26B3, or an antigen-binding fragment thereof;

(c) an antibody, or antigen-binding fragment thereof, that comprises heavy chain CDR1, CDR2, and CDR3 amino acid sequences and light chain CDR1, CDR2, and CDR3 amino acid sequences of any one of antibody 9F3, antibody 19D4, antibody 24F12, or antibody 26B3, as described in Table 1;

(d) an antibody, or antigen-binding fragment thereof, that comprises the heavy chain variable domain segment and light chain variable domain segment of any one of antibody 9F3, antibody 19D4, antibody 24F12, or antibody 26B3, as described in Table 1; or (e) an antibody having the amino acid sequence of antibody produced by any one of the cell lines deposited with the ATCC having accession number PTA-11887, PTA-11884, PTA-11886, or PTA-11885, or an antigen binding fragment thereof.

In some embodiments the sample may be contacted with more than one of the antibodies, or antigen-binding fragments described herein. For example, a sample may be contacted with a first antibody, or antigen-binding fragment thereof, and then contacted with a second antibody, or antigen-binding fragment thereof, wherein the first antibody or antigen-binding fragment and the second antibody or antigen-binding fragment are not the same antibody or antigen-binding fragment. In some embodiments, the first antibody, or antigen-binding fragment thereof, may be affixed to a surface, such as a multiwell plate, chip, or similar substrate prior to contacting the sample. In other embodiments the first antibody, or antigen-binding fragment thereof, may not be affixed, or attached, to anything at all prior to contacting the sample.

Various combinations of the antibodies, or antigen-binding fragments thereof, may be used to detect FRα in a sample. In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 9F3 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 19D4 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 9F3 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 24F12 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 9F3 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 26B3 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 19D4 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 9F3 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 19D4 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 24F12 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 19D4 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 26B3 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 24F 12 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 9F3 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 24F12 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 19D4 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 24F12 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 26B3 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 26B3 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 9F3 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 26B3 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 24F12 (as provided in Table 1). In one embodiment the sample may be first contacted with an antibody, or antigen-binding fragment thereof, that comprises heavy chain CDR1, CDR2, and CDR3 amino acid sequences and light chain CDR1, CDR2, and CDR3 amino acid sequences of antibody 26B3 (as provided in Table 1), and then separately contacted with a second antibody, or antigen-binding fragment thereof, that comprises heavy chain CDR1, CDR2, and CDR3 amino acid sequences and light chain CDR1, CDR2, and CDR3 amino acid sequences of antibody 19D4 (as provided in Table 1). In one embodiment the sample may be first contacted with an antibody, or antigen-binding fragment thereof, that comprises the heavy chain variable domain segment and light chain variable domain segment amino acid sequences of antibody 9F3 (as provided in Table 1), and then separately contacted with a second antibody, or antigen-binding fragment thereof, that comprises the heavy chain variable domain segment and light chain variable domain segment amino acid sequences of antibody 19D4 (as provided in Table 1). In one embodiment the sample may be first contacted with an antibody, or antigen-binding fragment thereof, that comprises the heavy chain variable domain segment and light chain variable domain segment amino acid sequences of antibody 9F3 (as provided in Table 1), and then separately contacted with a second antibody, or antigen-binding fragment thereof, that comprises the heavy chain variable domain segment and light chain variable domain segment amino acid sequences of antibody 24F12 (as provided in Table 1). In one embodiment the sample may be first contacted with an antibody, or antigen-binding fragment thereof, that comprises the heavy chain variable domain segment and light chain variable domain segment amino acid sequences of antibody 9F3 (as provided in Table 1), and then separately contacted with a second antibody, or antigen-binding fragment thereof, that comprises the heavy chain variable domain segment and light chain variable domain segment amino acid sequences of antibody 26B3 (as provided in Table 1). In one embodiment the sample may be first contacted with an antibody, or antigen-binding fragment thereof, that comprises the heavy chain variable domain segment and light chain variable domain segment amino acid sequences of antibody 19D4 (as provided in Table 1), and then separately contacted with a second antibody, or antigen-binding fragment thereof, that comprises the heavy chain variable domain segment and light chain variable domain segment amino acid sequences of antibody 9F3 (as provided in Table 1). In one embodiment the sample may be first contacted with an antibody, or antigen-binding fragment thereof, that comprises the heavy chain variable domain segment and light chain variable domain segment amino acid sequences of antibody 19D4 (as provided in Table 1), and then separately contacted with a second antibody, or antigen-binding fragment thereof, that comprises the heavy chain variable domain segment and light chain variable domain segment amino acid sequences of antibody 24F12 (as provided in Table 1). In one embodiment the sample may be first contacted with an antibody, or antigen-binding fragment thereof, that comprises the heavy chain variable domain segment and light chain variable domain segment amino acid sequences of antibody 19D4 (as provided in Table 1), and then separately contacted with a second antibody, or antigen-binding fragment thereof, that comprises the heavy chain variable domain segment and light chain variable domain segment amino acid sequences of antibody 26B3 (as provided in Table 1). In one embodiment the sample may be first contacted with an antibody, or antigen-binding fragment thereof, that comprises the heavy chain variable domain segment and light chain variable domain segment amino acid sequences of antibody 24F12 (as provided in Table 1), and then separately contacted with a second antibody, or antigen-binding fragment thereof, that comprises the heavy chain variable domain segment and light chain variable domain segment amino acid sequences of antibody 9F3 (as provided in Table 1). In one embodiment the sample may be first contacted with an antibody, or antigen-binding fragment thereof, that comprises the heavy chain variable domain segment and light chain variable domain segment amino acid sequences of antibody 24F12 (as provided in Table 1), and then separately contacted with a second antibody, or antigen-binding fragment thereof, that comprises the heavy chain variable domain segment and light chain variable domain segment amino acid sequences of antibody 19D4 (as provided in Table 1). In one embodiment the sample may be first contacted with an antibody, or antigen-binding fragment thereof, that comprises the heavy chain variable domain segment and light chain variable domain segment amino acid sequences of antibody 24F12 (as provided in Table 1), and then separately contacted with a second antibody, or antigen-binding fragment thereof, that comprises the heavy chain variable domain segment and light chain variable domain segment amino acid sequences of antibody 26B3 (as provided in Table 1). In one embodiment the sample may be first contacted with an antibody, or antigen-binding fragment thereof, that comprises the heavy chain variable domain segment and light chain variable domain segment amino acid sequences of antibody 26B3 (as provided in Table 1), and then separately contacted with a second antibody, or antigen-binding fragment thereof, that comprises the heavy chain variable domain segment and light chain variable domain segment amino acid sequences of antibody 9F3 (as provided in Table 1). In one embodiment the sample may be first contacted with an antibody, or antigen-binding fragment thereof, that comprises the heavy chain variable domain segment and light chain variable domain segment amino acid sequences of antibody 26B3 (as provided in Table 1), and then separately contacted with a second antibody, or antigen-binding fragment thereof, that comprises the heavy chain variable domain segment and light chain variable domain segment amino acid sequences of antibody 24F12 (as provided in Table 1). In one embodiment the sample may be first contacted with an antibody, or antigen-binding fragment thereof, that comprises the heavy chain variable domain segment and light chain variable domain segment amino acid sequences of antibody 26B3 (as provided in Table 1), and then separately contacted with a second antibody, or antigen-binding fragment thereof, that comprises the heavy chain variable domain segment and light chain variable domain segment amino acid sequences of antibody 19D4 (as provided in Table 1). In one embodiment the sample may be first contacted with the antibody produced by the cell line having ATCC accession number PTA-11887, or an antigen-binding fragment thereof, and then separately contacted with a second antibody produced by the cell line having ATCC accession number PTA-11884, or an antigen-binding fragment thereof. In one embodiment the sample may be first contacted with the antibody produced by the cell line having ATCC accession number PTA-11887, or an antigen-binding fragment thereof, and then separately contacted with a second antibody produced by the cell line having ATCC accession number PTA-11885, or an antigen-binding fragment thereof. In one embodiment the sample may be first contacted with the antibody produced by the cell line having ATCC accession number PTA-11887, or an antigen-binding fragment thereof, and then separately contacted with a second antibody produced by the cell line having ATCC accession number PTA-11886, or an antigen-binding fragment thereof. In one embodiment the sample may be first contacted with the antibody produced by the cell line having ATCC accession number PTA-11884, or an antigen-binding fragment thereof, and then separately contacted with a second antibody produced by the cell line having ATCC accession number PTA-11887, or an antigen-binding fragment thereof. In one embodiment the sample may be first contacted with the antibody produced by the cell line having ATCC accession number PTA-11884, or an antigen-binding fragment thereof, and then separately contacted with a second antibody produced by the cell line having ATCC accession number PTA-11885, or an antigen-binding fragment thereof. In one embodiment the sample may be first contacted with the antibody produced by the cell line having ATCC accession number PTA-11884, or an antigen-binding fragment thereof, and then separately contacted with a second antibody produced by the cell line having ATCC accession number PTA-11886, or an antigen-binding fragment thereof. In one embodiment the sample may be first contacted with the antibody produced by the cell line having ATCC accession number PTA-11885, or an antigen-binding fragment thereof, and then separately contacted with a second antibody produced by the cell line having ATCC accession number PTA-11884, or an antigen-binding fragment thereof. In one embodiment the sample may be first contacted with the antibody produced by the cell line having ATCC accession number PTA-11885, or an antigen-binding fragment thereof, and then separately contacted with a second antibody produced by the cell line having ATCC accession number PTA-11887, or an antigen-binding fragment thereof. In one embodiment the sample may be first contacted with the antibody produced by the cell line having ATCC accession number PTA-11885, or an antigen-binding fragment thereof, and then separately contacted with a second antibody produced by the cell line having ATCC accession number PTA-11886, or an antigen-binding fragment thereof. In one embodiment the sample may be first contacted with the antibody produced by the cell line having ATCC accession number PTA-11886, or an antigen-binding fragment thereof, and then separately contacted with a second antibody produced by the cell line having ATCC accession number PTA-11884, or an antigen-binding fragment thereof. In one embodiment the sample may be first contacted with the antibody produced by the cell line having ATCC accession number PTA-11886, or an antigen-binding fragment thereof, and then separately contacted with a second antibody produced by the cell line having ATCC accession number PTA-11885, or an antigen-binding fragment thereof. In one embodiment the sample may be first contacted with the antibody produced by the cell line having ATCC accession number PTA-11886, or an antigen-binding fragment thereof, and then separately contacted with a second antibody produced by the cell line having ATCC accession number PTA-11887, or an antigen-binding fragment thereof. In one embodiment the sample may be first contacted with an antibody capable of binding to the same epitope as the antibody produced by the cell line having ATCC accession number PTA-11887, or an antigen-binding fragment thereof, and then separately contacted with a second antibody capable of binding to the same epitope as antibody produced by the cell line having ATCC accession number PTA-11884, or an antigen-binding fragment thereof. In one embodiment the sample may be first contacted with an antibody capable of binding to the same epitope as the antibody produced by the cell line having ATCC accession number PTA-11887, or an antigen-binding fragment thereof, and then separately contacted with a second antibody capable of binding to the same epitope as antibody produced by the cell line having ATCC accession number PTA-11885, or an antigen-binding fragment thereof. In one embodiment the sample may be first contacted with an antibody capable of binding to the same epitope as the antibody produced by the cell line having ATCC accession number PTA-11887, or an antigen-binding fragment thereof, and then separately contacted with a second antibody capable of binding to the same epitope as antibody produced by the cell line having ATCC accession number PTA-11886, or an antigen-binding fragment thereof. In one embodiment the sample may be first contacted with an antibody capable of binding to the same epitope as the antibody produced by the cell line having ATCC accession number PTA-11884, or an antigen-binding fragment thereof, and then separately contacted with a second antibody capable of binding to the same epitope as antibody produced by the cell line having ATCC accession number PTA-11887, or an antigen-binding fragment thereof. In one embodiment the sample may be first contacted with an antibody capable of binding to the same epitope as the antibody produced by the cell line having ATCC accession number PTA-11884, or an antigen-binding fragment thereof, and then separately contacted with a second antibody capable of binding to the same epitope as antibody produced by the cell line having ATCC accession number PTA-11885, or an antigen-binding fragment thereof. In one embodiment the sample may be first contacted with an antibody capable of binding to the same epitope as the antibody produced by the cell line having ATCC accession number PTA-11884, or an antigen-binding fragment thereof, and then separately contacted with a second antibody capable of binding to the same epitope as antibody produced by the cell line having ATCC accession number PTA-11886, or an antigen-binding fragment thereof. In one embodiment the sample may be first contacted with an antibody capable of binding to the same epitope as the antibody produced by the cell line having ATCC accession number PTA-11885, or an antigen-binding fragment thereof, and then separately contacted with a second antibody capable of binding to the same epitope as antibody produced by the cell line having ATCC accession number PTA-11884, or an antigen-binding fragment thereof. In one embodiment the sample may be first contacted with an antibody capable of binding to the same epitope as the antibody produced by the cell line having ATCC accession number PTA-11885, or an antigen-binding fragment thereof, and then separately contacted with a second antibody capable of binding to the same epitope as antibody produced by the cell line having ATCC accession number PTA-11887, or an antigen-binding fragment thereof. In one embodiment the sample may be first contacted with an antibody capable of binding to the same epitope as the antibody produced by the cell line having ATCC accession number PTA-11885, or an antigen-binding fragment thereof, and then separately contacted with a second antibody capable of binding to the same epitope as antibody produced by the cell line having ATCC accession number PTA-11886, or an antigen-binding fragment thereof. In one embodiment the sample may be first contacted with an antibody capable of binding to the same epitope as the antibody produced by the cell line having ATCC accession number PTA-11886, or an antigen-binding fragment thereof, and then separately contacted with a second antibody capable of binding to the same epitope as antibody produced by the cell line having ATCC accession number PTA-11884, or an antigen-binding fragment thereof. In one embodiment the sample may be first contacted with an antibody capable of binding to the same epitope as the antibody produced by the cell line having ATCC accession number PTA-11886, or an antigen-binding fragment thereof, and then separately contacted with a second antibody capable of binding to the same epitope as antibody produced by the cell line having ATCC accession number PTA-11885, or an antigen-binding fragment thereof. In one embodiment the sample may be first contacted with an antibody capable of binding to the same epitope as the antibody produced by the cell line having ATCC accession number PTA-11886, or an antigen-binding fragment thereof, and then separately contacted with a second antibody capable of binding to the same epitope as antibody produced by the cell line having ATCC accession number PTA-11887, or an antigen-binding fragment thereof.

The described antibodies and antigen-binding fragments may be detectably labeled. In some embodiments labeled antibodies and antigen-binding fragments may facilitate the detection FRα via the methods described herein. Many such labels are readily known to those skilled in the art. For example, suitable labels include, but should not be considered limited to, radiolabels, fluorescent labels (such as DyLight® 649), epitope tags, biotin, chromophore labels, ECL labels, or enzymes. More specifically, the described labels include ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes, Alexafluor® dyes, and the like.

The described antibodies and antigen-binding fragments may be used in a variety of assays to detect FRα in a sample. Some suitable assays include, but should not be considered limited to, western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In some embodiments described herein detection of FRα-expressing cancer cells in a subject may be used to determine that the subject may be treated with a therapeutic agent directed against FRα. In some embodiments the therapeutic agent directed against FRα may be an antibody, such as Farletuzumab.

Methods for Diagnosing Cancer

Provided herein are methods for diagnosing ovarian, breast, thyroid, colorectal, endometrial, fallopian tube, or lung cancer of epithelial origin in a subject. In some embodiments, as described above, detecting FRα in a sample, such as a histological sample, a fine needle aspirate sample, resected tumor tissue, circulating cells, circulating tumor cells, and the like, provides the ability to diagnose cancer in the subject from whom the sample was obtained. In some embodiments, it may already be known that the subject from whom the sample was obtained has cancer, but the type of cancer afflicting the subject may not yet have been diagnosed or a preliminary diagnosis may be unclear, thus detecting FRα in a sample obtained from the subject can allow for, or clarify, diagnosis of the cancer.

In some embodiments the described methods involve assessing whether a subject is afflicted with FRα-expressing cancer by determining the amount of FRα that is present in a sample derived from the subject; and comparing the observed amount of FRα with the amount of FRα in a control sample, wherein a difference between the amount of FRα in the sample derived from the subject and the amount of FRα in the control sample is an indication that the subject is afflicted with an FRα-expressing cancer. In some embodiments the amount of FRα in the sample derived from the subject is assessed by contacting the sample with an antibody that binds FRα, such as the antibodies described herein. Similar methods may be used to determine if a subject is afflicted with cancer that is not associated with increased FRα production. The sample assessed for the presence of FRα may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the subject is a human.

In some embodiments the method of diagnosing an FRα-expressing cancer will involve: contacting a biological sample of a subject with an FRα-specific antibody, or antigen-binding fragment thereof (such as those derivable from the antibodies and fragments provided in Table 1), quantifying the amount of FRα present in the sample that is bound by the antibody or antigen-binding fragment thereof, comparing the amount of FRα present in the sample to a known standard; and determining whether the subject's FRα levels fall within the levels of FRα associated with cancer. In an additional embodiment, the diagnostic method can be followed with an additional step of administering or prescribing a cancer-specific treatment. In some embodiments the cancer-specific treatment may be directed against FRα-expressing cancers, such as Farletuzumab.

In some embodiments the described methods involve assessing whether a subject is afflicted with FRα-expressing cancer by determining the amount of FRα associated with a cell or tissue that is present in a sample derived from the subject; and comparing the observed amount of FRα with the amount of FRα in a control sample, wherein a difference between the amount of FRα in the sample derived from the subject and the amount of FRα in the control sample is an indication that the subject is afflicted with an FRα-expressing cancer.

In some embodiments the control sample may be derived from a subject that is not afflicted with FRα-expressing cancer. In some embodiments the control sample may be derived from a subject that is afflicted with FRα-expressing cancer. In some embodiments where the control sample is derived from a subject that is not afflicted with FRα-expressing cancer, an observed increase in the amount of FRα present in the sample, relative to that observed for the control sample, is an indication that the subject being assessed is afflicted with FRα-expressing cancer. In some embodiments where the control sample is derived from a subject that is not afflicted with FRα-expressing cancer, an observed decrease or similarity in the amount of FRα present in the test sample, relative to that observed for the control sample, is an indication that the subject being assessed is not afflicted with FRα-expressing cancer. In some embodiments where the control sample is derived from a subject that is afflicted with FRα-expressing cancer, an observed similarity in the amount of FRα present in the test sample, relative to that observed for the control sample, is an indication that the subject being assessed is afflicted with FRα-expressing cancer. In some embodiments where the control sample is derived from a subject that is afflicted with FRα-expressing cancer, an observed decrease in the amount of FRα present in the test sample, relative to that observed for the control sample, is an indication that the subject being assessed is not afflicted with FRα-expressing cancer.

In some embodiments the amount of FRα in the sample derived from the subject is assessed by contacting the sample with an antibody that binds FRα, such as the antibodies described herein. The sample assessed for the presence of FRα may be circulating cells, circulating tumor cells, cells that are not tissue associated (i.e., free cells), tissues (e.g., surgically resected tumor tissue, biopsies, including fine needle aspiration), histological preparations, and the like.

In some embodiments the described methods involve assessing whether a subject is afflicted with FRα-expressing cancer by determining the amount of FRα that is not associated with a cell or tissue that is present in a sample derived from the subject; and comparing the observed amount of FRα with the amount of FRα in a control sample, wherein a difference between the amount of FRα in the sample derived from the subject and the amount of FRα in the control sample is an indication that the subject is afflicted with an FRα-expressing cancer. In some embodiments the amount of FRα in the sample derived from the subject is assessed by contacting the sample with an antibody that binds FRα, such as the antibodies described herein. The sample assessed for the presence of FRα may be urine, blood, serum, plasma, saliva, ascites, histological preparations, and the like.

In various embodiments of the described methods, the cancer may be FRα-expressing cancer. In a particular embodiment, the FRα-expressing cancer is ovarian cancer. In some embodiments the FRα-expressing cancer is endometrial cancer. In some embodiments the FRα-expressing cancer is colorectal cancer. In some embodiments the FRα-expressing cancer is breast cancer. In some embodiments the FRα-expressing cancer is thyroid cancer. In some embodiments the FRα-expressing cancer is fallopian tube cancer. In another embodiment, the FRα-expressing cancer is non-small cell lung cancer, such as an adenocarcinoma. Alternatively, the described methods may be used to diagnose cancer that does not express FRα, such as squamous cell carcinoma.

In various aspects, the amount of FRα is determined by contacting the sample with an antibody, or antigen-binding fragment thereof, that binds FRα. In some embodiments, the sample may be contacted by more than one type of antibody, or antigen-binding fragment thereof, that binds FRα. In some embodiments, the sample may be contacted by a first antibody, or antigen-binding fragment thereof, that binds FRα and then contacted by a second antibody, or antigen-binding fragment thereof, that binds FRα. Antibodies such as those described herein may be used in this capacity. For example, the antibody is selected from the group consisting of:

(a) an antibody, or antigen-binding fragment thereof, that binds the same epitope as any one of antibody 9F3, antibody 19D4, antibody 24F12, or antibody 26B3;

(b) any one of antibody 9F3, antibody 19D4, antibody 24F12, or antibody 26B3, or an antigen-binding fragment thereof;

(c) an antibody, or antigen-binding fragment thereof, that comprises heavy chain CDR1, CDR2, and CDR3 amino acid sequences and light chain CDR1, CDR2, and CDR3 amino acid sequences of any one of antibody 9F3, antibody 19D4, antibody 24F12, or antibody 26B3, as described in Table 1;

(d) an antibody, or antigen-binding fragment thereof, that comprises the heavy chain variable domain segment and light chain variable domain segment of any one of antibody 9F3, antibody 19D4, antibody 24F12, or antibody 26B3, as described in Table 1; or (e) an antibody having the amino acid sequence of antibody produced by any one of the cell lines deposited with the ATCC having accession number PTA-11887, PTA-11884, PTA-11886, or PTA-11885, or an antigen binding fragment thereof.

Various combinations of the antibodies and antigen-binding fragments described in (a)-(e), as detailed above in the general section describing methods of detection, can be used to provide a "first" and "second" antibody or antigen-binding fragment to carry out the described diagnostic methods.

In certain embodiments, the amount of FRα is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

In various embodiments of the described diagnostic methods a control sample is used. The control sample may be a positive or negative assay control that ensures the assay used is working properly; for example, an assay control of this nature might be commonly used for immunohistochemistry assays. Alternatively, the control sample may be a standardized control amount of FRα in a healthy subject. In some embodiments, the observed FRα levels of the tested subject may be compared with FRα levels observed in samples from control subjects known to have FRα-expressing cancer. In some embodiments, the control subject's FRα-expressing cancer is ovarian cancer, endometrial cancer, colorectal cancer, breast cancer, thyroid cancer, fallopian tube cancer, or lung cancer, such as adenocarcinoma. In some embodiments, the control subject is known to have early stage FRα-expressing cancer, such as stage I ovarian cancer, endometrial cancer, colorectal cancer, breast cancer, thyroid cancer, fallopian tube cancer, or lung cancer (e.g., adenocarcinoma). In some embodiments, the control subject is known to have intermediate stage FRα-expressing cancer, such as stage II ovarian cancer, endometrial cancer, colorectal cancer, breast cancer, thyroid cancer, fallopian tube cancer, or lung cancer (e.g., adenocarcinoma). In some embodiments, the control subject is known to have late stage FRα-expressing cancer, such as stage III or stage IV ovarian cancer, endometrial cancer, colorectal cancer, breast cancer, thyroid cancer, fallopian tube cancer, or lung cancer (e.g., adenocarcinoma).

The diagnostic methods provided herein also provide a basis upon which it may be possible to predict whether a subject has a relatively higher or lower likelihood of surviving 5 years following diagnosis. In some embodiments, the described method may be used to predict a favorable outcome for a subject having adenocarcinoma, wherein a favorable outcome is defined as having an increased 5-year survival rate. As data provided herein indicate, subjects determined to have stage I or stage II adenocarcinoma that does not express FRα are about 2 times more likely to die within five years than subjects determined to have stage I or stage II adenocarcinoma that does express FRα. Accordingly, the diagnostic methods described herein may be combined with this knowledge to allow for a method of predicting 5-year survivorship likelihood for subjects determined to have cancer. In some embodiments the method is used to predict the 5-year survivorship likelihood for subjects determined to have adenocarcinoma.

In some embodiments the described prognostic method will involve: contacting a biological sample of a subject with an FRα-specific antibody, or antigen-binding fragment thereof (such as those derivable from the antibodies and fragments provided in Table 1), quantifying the amount of FRα present in the sample that is bound by the antibody or antigen-binding fragment thereof, comparing the amount of FRα present in the sample to a known standard; and determining whether the subject's FRα levels indicate the presence of a FRα expressing cancer, thereby allowing for a prediction to be made as to the likelihood the subject will survive five years after being diagnosed with cancer. In some embodiments the subject is known to have or determined to have adenocarcinoma. In some embodiments the subject is a human.

Methods for Monitoring Cancer

Provided herein are methods for monitoring cancer of epithelial origin in a subject. In some embodiments the described methods involve assessing whether FRα-expressing cancer is progressing, regressing, or remaining stable by determining the amount of FRα that is present in a test sample derived from the subject; and comparing the observed amount of FRα with the amount of FRα in a sample obtained from the subject at an earlier point in time, wherein a difference between the amount of FRα in the test sample and the earlier sample provides an indication of whether the cancer is progressing, regressing, or remaining stable. In this regard, a test sample with an increased amount of FRα, relative to the amount observed for the earlier sample, may indicate progression of an FRα-expressing cancer. Conversely, a test sample with a decreased amount of FRα, relative to the amount observed for the earlier sample, may indicate regression of an FRα-expressing cancer. Accordingly, a test sample with an insignificant difference in the amount of FRα, relative to the amount observed for the earlier sample, may indicate a state of stable disease for an FRα-expressing cancer. In some embodiments the amount of FRα in a sample derived from the subject is assessed by contacting the sample with an antibody that binds FRα, such as the antibodies described herein. The sample assessed for the presence of FRα may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like. In some embodiments the subject is a human.

In some embodiments the method of monitoring an FRα-expressing cancer will involve: contacting a biological sample of a subject with an FRα-specific antibody, or antigen-binding fragment thereof (such as those derivable from the antibodies and fragments provided in Table 1), quantifying the amount of FRα present in the sample that is bound by the antibody or antigen-binding fragment thereof, comparing the amount of FRα present in the sample to the amount of FRα determined to be in a sample from the same subject at an earlier point in time; and determining whether the subject's FRα levels have changed over time. A test sample with an increased amount of FRα, relative to the amount observed for the earlier sample, may indicate progression of an FRα-expressing cancer. Conversely, a test sample with a decreased amount of FRα, relative to the amount observed for the earlier sample, may indicate regression of an FRα-expressing cancer. Accordingly, a test sample with an insignificant difference in the amount of FRα, relative to the amount observed for the earlier sample, may indicate a state of stable disease for an FRα-expressing cancer. In some embodiments, the FRα levels of the sample may be compared to a known standard, alone or in addition to the FRα levels observed for a sample assessed at an earlier point in time. In some embodiments the known standard may be FRα protein at a known concentration (e.g., a recombinant or purified FRα protein sample). In an additional embodiment, the diagnostic method can be followed with an additional step of administering a cancer-specific treatment. In some embodiments the cancer-specific treatment may be directed against FRα-expressing cancers, such as Farletuzumab.

In some embodiments the described methods involve assessing whether FRα-expressing cancer is progressing, regressing, or remaining stable by determining the amount of FRα associated with a cell or tissue that is present in a test sample derived from the subject; and comparing the observed amount of FRα with the amount of FRα in a sample obtained from the subject, in a similar manner, at an earlier point in time, wherein a difference between the amount of FRα in the test sample and the earlier sample provides an indication of whether the cancer is progressing, regressing, or remaining stable. In this regard, a test sample with an increased amount of FRα, relative to the amount observed for the earlier sample, may indicate progression of an FRα-expressing cancer. Conversely, a test sample with a decreased amount of FRα, relative to the amount observed for the earlier sample, may indicate regression of an FRα-expressing cancer. Accordingly, a test sample with an insignificant difference in the amount of FRα, relative to the amount observed for the earlier sample, may indicate a state of stable disease for an FRα-expressing cancer. In some embodiments the amount of FRα in a sample derived from the subject is assessed by contacting the sample with an antibody that binds FRα, such as the antibodies described herein. The sample assessed for the presence of FRα may be circulating cells, circulating tumor cells, cells that are not tissue associated (i.e., free cells), tissues (e.g., surgically resected tumor tissue, biopsies, including fine needle aspiration), histological preparations, and the like.

In some embodiments the described methods involve assessing whether FRα-expressing cancer is progressing, regressing, or remaining stable by determining the amount of FRα not associated with a cell or tissue that is present in a test sample derived from the subject; and comparing the observed amount of FRα with the amount of FRα in a sample obtained from the subject, in a similar manner, at an earlier point in time, wherein a difference between the amount of FRα in the test sample and the earlier sample provides an indication of whether the cancer is progressing, regressing, or remaining stable. In this regard, a test sample with an increased amount of FRα, relative to the amount observed for the earlier sample, may indicate progression of an FRα-expressing cancer. Conversely, a test sample with a decreased amount of FRα, relative to the amount observed for the earlier sample, may indicate regression of an FRα-expressing cancer. Accordingly, a test sample with an insignificant difference in the amount of FRα, relative to the amount observed for the earlier sample, may indicate a state of stable disease for an FRα-expressing cancer. In some embodiments the amount of FRα in a sample derived from the subject is assessed by contacting the sample with an antibody that binds FRα, such as the antibodies described herein. The sample assessed for the presence of FRα may be urine, blood, serum, plasma, saliva, ascites, histological preparations, and the like.

In various embodiments of the described methods, the cancer may be FRα-expressing cancer. In a particular embodiment, the FRα-expressing cancer is ovarian cancer. In some embodiments the FRα-expressing cancer is endometrial cancer. In some embodiments the FRα-expressing cancer is colorectal cancer. In some embodiments the FRα-expressing cancer is breast cancer. In some embodiments the FRα-expressing cancer is thyroid cancer. In some embodiments the FRα-expressing cancer is fallopian tube cancer. In another embodiment, the FRα-expressing cancer is non-small cell lung cancer, such as an adenocarcinoma.

In various aspects, the amount of FRα is determined by contacting the sample with an antibody, or antigen-binding fragment thereof, that binds FRα. In some embodiments, the sample may be contacted by more than one type of antibody, or antigen-binding fragment thereof, that binds FRα. In some embodiments, the sample may be contacted by a first antibody, or antigen-binding fragment thereof, that binds FRα and then contacted by a second antibody, or antigen-binding fragment thereof, that binds FRα. Antibodies such as those described herein may be used in this capacity. For example, the antibody may be selected from among:

(a) an antibody, or antigen-binding fragment thereof, that binds the same epitope as any one of antibody 9F3, antibody 19D4, antibody 24F12, or antibody 26B3;

(b) any one of antibody 9F3, antibody 19D4, antibody 24F12, or antibody 26B3, or an antigen-binding fragment thereof;

(c) an antibody, or antigen-binding fragment thereof, that comprises heavy chain CDR1, CDR2, and CDR3 amino acid sequences and light chain CDR1, CDR2, and CDR3 amino acid sequences of any one of antibody 9F3, antibody 19D4, antibody 24F12, or antibody 26B3, as described in Table 1;

(d) an antibody, or antigen-binding fragment thereof, that comprises the heavy chain variable domain segment and light chain variable domain segment of any one of antibody 9F3, antibody 19D4, antibody 24F12, or antibody 26B3, as described in Table 1; or (e) an antibody having the amino acid sequence of antibody produced by any one of the cell lines deposited with the ATCC having accession number PTA-11887, PTA-11884, PTA-11886, or PTA-11885, or an antigen binding fragment thereof.

Various combinations of the antibodies and antigen-binding fragments described in (a)-(e), as detailed above in the general section describing methods of detection, can be used to provide a "first" and "second" antibody or antigen-binding fragment to carry out the described monitoring methods.

In certain embodiments, the amount of FRα is determined by western blot analysis, radioimmunoassay, immunofluorimetry, immunoprecipitation, equilibrium dialysis, immunodiffusion, electrochemiluminescence (ECL) immunoassay, immunohistochemistry, fluorescence-activated cell sorting (FACS) or ELISA assay.

Additional aspects of the summarized subject matter are provided in greater detail in the detailed description and provided examples and associated figures.

Kits for Detecting the FRα

Provided herein are kits for detecting FRα in a sample. These kits include one of more of the FRα-specific antibodies described herein, or an antigen-binding fragment thereof, and instructions for use of the kit. In some embodiments the antibody, or antigen-binding fragment, provided in the described kits may be one or more of:

(a) an antibody, or antigen-binding fragment thereof, that binds the same epitope as any one of antibody 9F3, antibody 19D4, antibody 24F12, or antibody 26B3;

(b) any one of antibody 9F3, antibody 19D4, antibody 24F12, or antibody 26B3, or an antigen-binding fragment thereof;

(c) an antibody, or antigen-binding fragment thereof, that comprises heavy chain CDR1, CDR2, and CDR3 amino acid sequences and light chain CDR1, CDR2, and CDR3 amino acid sequences of any one of antibody 9F3, antibody 19D4, antibody 24F12, or antibody 26B3, as described in Table 1;

(d) an antibody, or antigen-binding fragment thereof, that comprises the heavy chain variable domain segment and light chain variable domain segment of any one of antibody 9F3, antibody 19D4, antibody 24F12, or antibody 26B3, as described in Table 1; or (e) an antibody having the amino acid sequence of antibody produced by any one of the cell lines deposited with the ATCC having accession number PTA-11887, PTA-11884, PTA-11886, or PTA-11885, or an antigen binding fragment thereof.

The provided antibody, or antigen-binding fragment, may be in solution; lyophilized; affixed to a substrate, carrier, or plate; or conjugated to a detectable label.

The described kits may also include additional components useful for performing the methods described herein. By way of example, the kits may comprise means for obtaining a sample from a subject, a control sample, e.g., a sample from a subject having slowly progressing cancer and/or a subject not having cancer, one or more sample compartments, and/or instructional material which describes performance of a method of the invention and tissue specific controls/standards.

The means for determining the level of FRα can further include, for example, buffers or other reagents for use in an assay for determining the level of FRα. The instructions can be, for example, printed instructions for performing the assay and/or instructions for evaluating the level of expression of FRα.

The described kits may also include means for isolating a sample from a subject. These means can comprise one or more items of equipment or reagents that can be used to obtain a fluid or tissue from a subject. The means for obtaining a sample from a subject may also comprise means for isolating blood components, such as serum, from a blood sample. Preferably, the kit is designed for use with a human subject.

The described kits may also include a blocking reagent that can be applied to a sample to decrease nonspecific binding of a primary or secondary antibody. An example of a blocking reagent is bovine serum albumin (BSA), which may be diluted in a buffer prior to use. Other commercial blocking reagents, such as Block Ace and ELISA Synblock (AbD serotec), Background Punisher (BIOCARE MEDICAL), and StartingBlock™ (Thermo Fisher Scientific) are known in the art. The described kits may also include a negative control primary antibody that does not bind to FRα sufficiently to yield a positive result in an antibody-based detection assay. In addition, the described kits may include a secondary antibody capable of binding to a FRα primary antibody, such as antibody 9F3, antibody 19D4, antibody 24F12, or antibody 26B3. In some embodiments the secondary antibody may be conjugated to a detectable label, such as horse radish peroxidase (HRP) or a fluorophore, to allow for detection of the primary antibody bound to a sample. The described kits may also include a colorimetric or chemiluminescent substrate that allows the presence of a bound secondary antibody to be detected on a sample. In some embodiments the colorimetric or chemiluminescent substrate may be 2,2'-azino-bis(3-ethylbenzothiazoline-6-sulphonic acid) (ABTS); 3,3',5,5'-Tetramethylbenzidine (TMB); 3,3'-Diaminobenzidine (DAB); SuperSignal® (Thermo Fisher Scientific); ECL reagent (Thermo Fisher Scientific) or other such reagents known to those of ordinary skill in the art.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within the and can be made without departing from the true scope of the invention.

Example 1

Expression and Purification of Recombinant, Human FRα

To conduct the experiments associated with the studies described herein, several folate receptor alpha (FRα)-expressing cell systems or lines were created to generate FRα-expressing cell substrates or to generate purified recombinant human FRα protein. One expression system used was an Sf9 insect cell line that expressed recombinant human FRα via baculovirus. This system was prepared using a human FRα sequence, containing a leader sequence optimized for insect cell expression, a N-terminal 6× histidine (6×his) epitope tag, and the native GPI attachment site intact. The cells were then incubated in a 1 L shake flask and log-phase cultures of Sf9 insect cells were infected with the recombinant baculovirus at a multiplicity of infection (MOI) of <1. Cells from 30 L of culture were harvested, lysed and extracted 2× with 1× phosphate-buffered saline (PBS) containing 10 mM 3-[(3-cholamidopropyl)dimethylammonio]-1-propanesulfonate (CHAPS). The NaCl concentration was adjusted to 300 mM and filtered through a 0.2 um membrane. The clarified supernatant was purified by affinity chromatography, using 1×PBS with 2M NaCl, 1 mM CHAPS, pH 7.4 as wash buffer, followed by elution with 10 mM 3-(N-morpholino)propanesulfonic acid (MOPS), 3M $MgCl_2$, 1 mM CHAPS, pH 6.8. Peak fractions were dialyzed extensively against 1×PBS, pH 7.4, analyzed for purity by SDS-PAGE, quantitated by bicinchoninic acid assay (BCA) assay, aliquoted and stored at −80 degrees Celsius.

A Chinese hamster ovary (CHO) cell line stably expressing and secreting human FRα was produced using a human folate receptor alpha (FRα) sequence, containing a human immunoglobulin kappa leader sequence and a C-terminal 6×his epitope tag replacing the GPI attachment site. Once produced, the FRα-expressing CHO cells were grown at 25 L-scale in wave bags. To purify the secreted FRα protein, cell supernatant was cleared of cellular debris by depth filtration and then concentrated 10-fold by tangential flow filtration and diafiltered into 50 mM sodium phosphate, 300 mM NaCl, 1 mM imidazole, pH 8.0. This was loaded onto a pre-packed Talon® IMAC column using an FPLC. Unbound material was washed out using 50 mM sodium phosphate, 300 mM NaCl, 5 mM imidazole, pH 8.0 and bound protein was eluted using a linear gradient of 5 mM-100 mM imidazole in 50 mM sodium phosphate, 300 mM NaCl, pH 8.0. Peak fractions were dialyzed extensively against 1×PBS, pH 7.4, analyzed for purity by SDS-PAGE, quantitated by BCA assay, aliquoted and stored at −80 degrees Celsius.

A similar cell system was also produced for human folate receptor beta (FRβ), human folate receptor gamma (FRγ), and human folate receptor delta (FRδ). Briefly, constructs of either FRβ, FRγ, or FRδ containing a human immunoglobulin kappa leader sequence and a C-terminal 6×his epitope tag replacing the GPI attachment site, were used to transiently transfect 1 L cultures of 293F cells. Recombinant FR proteins were purified as described above for human FRα.

A Chinese hamster ovary (CHO) cell line stably expressing and secreting a human mesothelin sequence, containing a human immunoglobulin kappa leader sequence and a C-terminal 6×his epitope tag replacing the GPI attachment site, was also prepared, as mesothelin served as a negative control for many studies. Human mesothelin-expressing CHO cells were grown at 25 L-scale in wave bags. To purify the secreted mesothelin protein, cell supernatant was cleared of debris by hollow-fiber filtration and clarified supernatant was concentrated 10-fold by tangential flow filtration. Supernatant NaCl concentration was adjusted to 300 mM NaCl and 0.5 mM imidazole. This was loaded onto a pre-packed cobalt-charged immobilized metal affinity chromatography (Talon® IMAC) column using an FPLC. Unbound material was washed out using 50 mM sodium phosphate, 300 mM NaCl, 3 mM imidazole, pH 8.0 and bound protein was eluted using 50 mM sodium phosphate, 300 mM NaCl, 150 mM imidazole, pH 8.0. Peak fractions were dialyzed extensively against 50 mM potassium phosphate, pH 7.5. Ammonium sulfate was added to a final concentration of 1M, and final purification was then done on a pre-packed phenyl sepharose column using a step gradient of 1M-0M ammonium sulfate in 50 mM potassium phosphate, pH 7.5. Peak fractions were dialyzed extensively against 1x PBS, pH 7.4, analyzed for purity by SDS-PAGE, quantitated by BCA assay, aliquoted and stored at −80 degrees Celsius.

Example 2

Production of Purified Reduced and Alkylated FRα

Efforts were undertaken to produce a reduced and alkylated antigenic form of FRα. To reduce the protein, purified FRα was concentrated to 2 mg/mL in phosphate buffered saline (pH 7.4) using centrifugal filters (Amicon® Ultra, 3 kD MW limit). The protein concentration was determined using a BCA assay (Thermo Scientific). The resultant FRα was diluted 1:1 in 8M urea/PBS to generate a final concentration of 1 mg/mL FRα in PBS containing 4M urea. Dithiothreitol solution (500 mM in PBS) was added to a final concentration of 10 mM. The solution was incubated at 65 degrees Celsius for one hour, and cooled to room temperature.

Next 1M of iodoacetamide solution in phosphate buffer saline was added into the reduced folate receptor solution to a final concentration of 10 mM, and the reaction was kept in dark at room temperature for 30 minutes. The protein remained soluble under these conditions. The final reduced FRα to be used for immunization was stored in phosphate buffer saline containing 4M of urea, 10 mM of DTT, and 10 mM of iodoacetamide.

FIG. 1 shows the differential migration of native FRα protein and a reduced and alkylated form of the protein analyzed by SDS-PAGE under nonreducing conditions.

Example 3

Production of Hybridomas Using FRα

Eight week old female Balb/c mice were immunized with hexa-histidine tagged FRα protein (n=5) or reduced and alkylated FRα protein (n=5). Initial intraperitoneal immunizations administered on day 0 comprised 50 µg of the respective immunogen mixed 1:1 (v:v) with complete Freund's adjuvant (Rockland, Cat#D614-0050). Mice were then boosted with 50 µg immunogen mixed 1:1 (v:v) with incomplete Freund's adjuvant (Rockland, Cat#D615-0050) administered intraperitoneally 14 days later and every 21 days thereafter. Blood samples were collected from immunized mice 24 days after the initial immunization and every 21 days thereafter.

Collected blood samples were analyzed by direct enzyme-linked immunoassay (EIA) against FRα. Plates were coated with FRα protein (100 ml of a 1 mg/mL solution in PBS, 0.02 M potassium phosphate, 0.15 M Sodium Chloride, pH 7.2) and incubated overnight at 4° C., washed with PBS containing 0.2% polysorbate 20 (Tween®-20) (PBST; Rockland, Cat#MB-075-1000) and blocked with 3% fish gel (Sigma) for 1 hr at room temperature. A 3-fold dilution series of individual mouse serum samples were allowed to bind for 1 hr at room temperature, plates were then washed 3 times with PBST and subsequently probed with an HRP-conjugated rabbit-anti-mouse antibody (Rockland, Cat#610-4320) at 1:2500 for 30 minutes at 37° C. TMB substrate (Rockland, Cat#TMBE-100) was added and the reaction was stopped after 30 minutes by addition of 100 mL of 1M HCl prior to absorbance reading at 450 nm (Microplate Reader "Benchmark"; Biorad). All samples were counter-screened against hexa-histidine tagged recombinant mesothelin (mesothelin-His$_6$) protein as a negative control.

Spleens from mice showing the highest antigen-specific titers were harvested and hybridomas were prepared by electrofusion (Hybrimune™ Model CEEF-50B Waveform Generator; Cellectis, Romainville, France) of splenocytes with Sp2/0 Ag14 myeloma cells (ATTC CRL1581). Subsequently, hybridoma supernatants were screened by ELISA against FRα and recombinant Mesothelin-His$_6$ as described above to select positive parental fusion cell lines.

Selected parental cell lines determined to produce antibodies reactive to recombinant human FRα (rhFRα) were then subcloned by limiting dilution. The antibodies produced by these cells were then retested for FRα binding and isotyped using the Clonetyping™ System (SouthernBiotech, Birmingham, Ala.). Supernatants from these clones were further screened by direct ELISA against three additional isoforms of the human folate receptor (FRβ, FRγ and FRδ) to determine receptor specificity. Plates were coated overnight with 100 µl of a 1 µg/mL solution of the respective FRα isoform at 4° C., washed with PBS containing 0.2% polysorbate 20 (Tween®-20) (Rockland, Cat#MB-075-1000) and blocked with 3% fish gel (Sigma). A 3-fold dilution series of culture supernatants was allowed to bind for 1 hr at room temperature, before plates were washed and probed with an HRP-conjugated anti-mouse antibody as described above. Clones producing antibodies reactive to FRβ, FRγ and FRδ were not selected for further analysis.

Four selected hybridoma clones, 19D4.B7, 26B3.F2, 24F12.B1, and 9F3.H9.H3.H3.B5.G2, were deposited with the American Type Culture Collection on May 19, 2011 and were assigned ATCC accession numbers PTA-11884, PTA-11885, PTA-11886, and PTA-11887, respectively.

Example 4

Production of Purified Monoclonal Antibodies to FRα

Selected cell lines were tested for mycoplasma using a mycoplasma test kit (Rockland, Cat#MAB-012) before seeding into 1 L roller bottles containing serum free medium (Invitrogen, Cat#12045-076) and 5% low IgG FBS (0.1 µg/ml) (Gibco, Cat#16250-078) at 0.5×10$^5$ cells/mL. Cultures were allowed to grow at 37° C. for either 14 or 21 days, after which supernatant was harvested and concentrated approximately 10-fold through a 50 kDa filtration membrane (Spectrum Labs, Rancho Dominguez Calif.) and then purified using protein A chromatography (Rockland, Cat#PA50-00-0025). Bound antibody was eluted with 0.1M sodium citrate, pH 3.5/4.5 depending on antibody isotype, and buffer was exchanged against PBS by dialysis using a 12-14 kDa membranous tubing (Spectrum Labs, Rancho Dominguez Calif.). Purified antibody was sterile filtered using a 0.22 µm Express™ PLUS Stericups (Millipore, Billerica Mass.) and stored at 4° C. for further testing.

Efforts were undertaken to sequence the heavy and light chains of four selected hybridomas clones (9F3-H9, 19D4-B7, 24F12-B1, and 26B3-F2). First, total RNA was isolated from each hybridoma cell line (cell pellets of 1×10$^3$ to 1×10$^5$ cells each) using the RNAqueous® kit (Ambion) according to the manufacturer's protocol. RNA was quantified using a NanoDrop™ 8000 spectrophotometer (Thermo Scientific).

Isolated RNA was then amplified via multiplex RT-PCR, performed in triplicate for each hybridoma with a Mastercycler® EP Gradient Thermocycler (Eppendorf). First, two separate gene-specific cDNA amplifications were performed for each hybridoma (≤1 ug RNA/reaction) to determine which Ig heavy and light chain genes were used during Ig rearrangement. Each cocktail consisted of unique family-specific primers designed to anneal to any of the potential murine Ig V gene families (IgHv, IgKv) and Ig constant region genes (IgHc$_{Gamma}$, IgKc). cDNA generation and amplification was performed using SuperScript® III One-Step RT-PCR System with Platinum® Taq High Fidelity (Invitrogen) under the following conditions: 55° C. for 30 minutes and 95° C. for 2 minutes, followed by 40 cycles of 95° C. for 1 minute, 55° C. for 1 minute, 68° C. for 1 minute, and a final 68° C. for 10 minutes completion step. DNA products were electrophoresed on a 2% agarose gel. Appropriate bands were excised and gel purified using the QIAquick® Gel Extraction Kit (Qiagen) following the manufacturer's protocol. Purified DNA was submitted for sequencing (GE-NEWIZ, Inc., South Plainfield, N.J.) to determine the germline gene segments expressed by each hybridoma.

Further RT-PCR analysis suited to the particular genes identified for each hybridoma was then performed using the same RNA source as above and gene-specific primers (in contrast to family-specific primers used in the multiplex RT-PCR mixture). To facilitate cloning, amplified Ig cDNAs were placed into an In-Fusion (IF) expression vector, each gene-specific primer also contained vector-compatible linker sequences which would enable homologous crossover. All other reagents and thermocycler conditions are the same as those used for the multiplex RT-PCR experiments, described above.

Example 5

Characterization of Antibody Binding to FRα

Binding characteristics of the purified monoclonal antibodies to FRα were determined by surface plasmon resonance (SPR) experiments. All of the SPR experiments were performed at 25° C. using a BIAcore T100 with research grade CM5 chips (GE Healthcare), as specified by the manufacturer. Initially, anti-mouse IgG provided in the mouse antibody capture kit (GE Healthcare) was immobilized by amide coupling to CM5 sensor chips. Mouse anti-FRαmonoclonal antibodies (26B3, 24F12, 19D4, or 9F3) were captured on individual flow cells per binding cycle, while the fourth flow cell was used as a reference. Binding experiments were performed with HBS-P (GE Healthcare) as running buffer and at a flow rate of 30 μL/min. Each monoclonal antibody sample (0.5 μg/mL) was injected for 3 minutes to capture the antibody. Various concentrations of purified recombinant human FRα(rh-FRα) (1 nM-30 nM) were then injected over the FRα-specific and reference surfaces for 3 minutes to record binding sensograms using a single-cycle kinetics method. The dissociation profile was monitored for 25 minutes. In between bindings, the surface was regenerated with a 30 μl injection of 10 mM glycine (pH 1.7). The sensograms were processed and fitted to a 1:1 Langmuir binding model using BIAcore T100 evaluation software (version 2.0.1). Some of the binding characteristics of antibodies 26B3, 24F12, 19D4, and 9F3 are provided in Table 2.

TABLE 2

Binding characteristics of FRα-specific antibodies.

| Abbreviated Clone Name | ka (1/Ms) | kd (1/s) | KD (M) | Chi. Sq |
|---|---|---|---|---|
| 26B3 | $5.24 \times 10^5$ | $1.43 \times 10^{-5}$ | $2.73 \times 10^{-11}$ | 2.48 |
| 24F12 | $3.93 \times 10^5$ | $3.99 \times 10^{-5}$ | $1.02 \times 10^{-10}$ | 1.08 |
| 19D4 | $4.27 \times 10^5$ | $2.42 \times 10^{-4}$ | $5.67 \times 10^{-10}$ | 0.656 |
| 9F3 | $4.34 \times 10^5$ | $3.10 \times 10^{-4}$ | $7.15 \times 10^{-10}$ | 1.89 |

Example 6

Epitope Mapping of Selected FRα-Specific Antibodies

FRα-specific antibodies 26B3, 24F12, and 9F3 were further assessed in epitope binding studies using Octet QK. The results showed that 26B3 and 24F12, which have high affinities to purified human FRα, compete with one another for binding to FRα. Thus, these antibodies may share a common epitope, or have epitopes that are immediately adjacent to each other. The results also indicate that the 9F3 antibody has a unique epitope, since it did not compete with other FRα-specific antibodies for binding to FRα.

Additional epitope mapping studies were carried out by ExSAR™ using hydrogen/deuterium exchange mass spectrometry and docking methods. The results of these studies for antibodies 9F3, 24F12, and 26B3 are illustrated in FIG. 2. With regard to the epitope for antibody 26B3, these data suggest that it is accessible in the native, membrane-anchored structure, given the ability of 26B3 to recognize native FRα by flow cytometry. Furthermore, these data further suggest that the conformational constraints of the epitope recognized by MAb 26B3, as demonstrated by its inability to detect the protein on reduced western blots, are related to the cysteine at position 185 in the FRα protein which forms a di-sulfide bridge with cysteine 111.

Example 7

Recognition of Denatured and Chemically-Preserved Forms of FRα

Experiments were conducted to determine whether any of the FRα-specific antibodies, described above, could recognize denatured forms of FRα. For these analyses CHOK1 cells stably expressing GPI-linked human FRα, β, or Δ, were lysed in 1.1% OBG buffer (50 mM Tris-HCl, pH 7.5, 150 mM NaCl, 1.1% OBG) supplemented with Complete Mini Protease Inhibitor Cocktail (Roche Diagnostics, Indianapolis, Ind.) and PMSF (100 nM), and placed on ice for 15 minutes. Lysates were pre-cleared by centrifugation at 13,000 rpm for 15 minutes to remove debris. For reduced and denatured samples, equal amounts of protein (20 μg) were boiled for 10 minutes in NuPAGE® LDS sample buffer (Invitrogen) containing 5% β-mercaptoethanol+40 mM DTT. Proteins were separated using SDS-polyacrylamide gel electrophoresis (SDS-PAGE) on a 4-12% bis-tris gel (Invitrogen) and transferred to a PVDF membrane. The membrane was blocked in PBST+ 5% non-fat milk for 1 h at room temperature after which time, the membrane was washed twice with PBST. Immunoblotting was conducted using purified mouse monoclonal antibodies 9F3, 19D4, 24F12, or 26B3 (1 μg/mL) specific for FRα, which were detected with a goat-anti-mouse HRP-conjugated antibody and visualized using SuperSignal® West Pico chemiluminescent substrate, (Pierce, Rockford, Ill.). Luminescence was visualized using the Omega 12iC molecular imaging system (Ultra-Lum, Claremont, Calif.) with image analysis performed using UltraQuant™ 6.0 software (Ultra-Lum).

Western blot analyses were also performed using purified folate receptor preparations. For these experiments, 0.5 μg of purified human FRα, β, Γ or Δ, produced as described in Example 1, were incubated in 1×SDS-PAGE sample loading buffer (Invitrogen) with or without 20 mM DTT, boiled for 10 min, and electrophoresed on 4-12% gradient SDS-PAGE gels. Protein was transferred to PVDF membrane and blots probed as described above. Gels were run using Benchmark™ prestained protein ladder (Novex®). Gels using purified recombinant FR proteins were also visualized via silver-staining to ensure equal amounts of protein were loaded.

Figure 3:
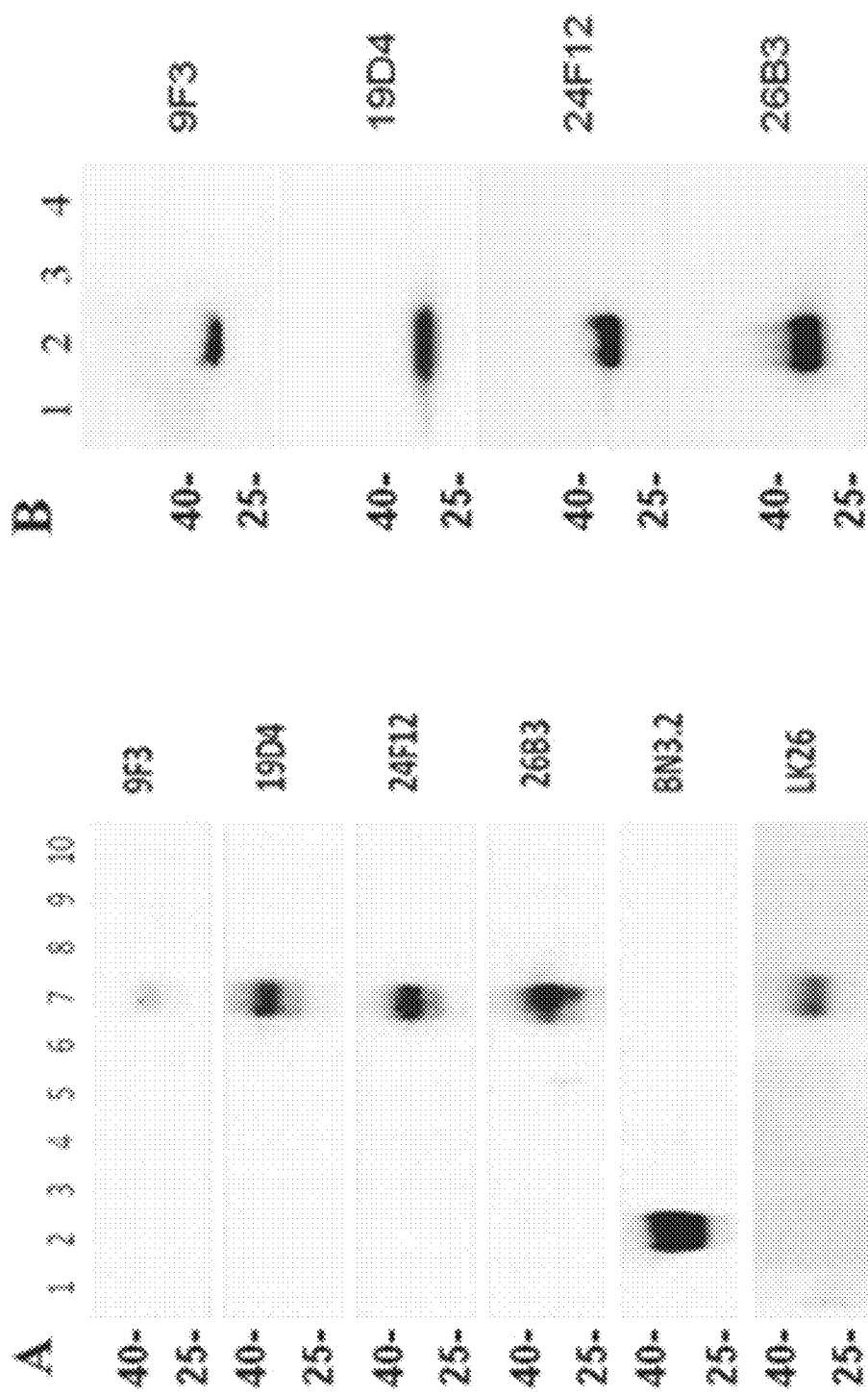
FIG. 3 shows four western blots of purified recombinant (A) and whole cell lysates (B) from CHO cells expressing FRα or FR homologs FRβ, FRΓ or FRΔ were run on SDS-PAGE gels. Proteins were prepared in sample buffer with or without reducing agents. Panel A, lane 1, molecular weight markers, lanes 2-5. 0.5 μg reduced FRα, FRβ, FRΓ, and FRΔ, respectively; lane 6, blank; lanes 7-10, 0.5 μg nonreduced FRα, FRβ, FRΓ, and FRΔ, respectively. The positive band represents the only reactive species in each lane and corresponds to a molecular weight of ~38 kDa. Panel B, lane 1 molecular weight markers, lane 2 CHO— FRα, lane 3, CHO—FRβ, lane 4 CHO—FRΔ whole cell lysates prepared in sample buffer without reducing agents and fractionated on an SDS-PAGE gel. Each panel is probed with the designated anti-FRα mAb labeled on the right. The molecular weights for FR are: FRα ~38 kDA; FRβ ~30 kDa; FRΓ ~28 kDa; FRΔ ~26 kDa. The LK26 and BN3.2 antibodies that recognize FRα under denatured and nonreduced or reduced conditions, respectively, were used as positive controls.

Western blot analyses indicate that antibodies 19D4, 9F3, 24F12, and 26B3 recognize nonreduced FRα, however, binding to reduced and denatured samples was not detected for any of these antibodies (FIGS. 3(A) and (B)).

Immunohistochemistry (IHC) studies were also conducted to determine whether any of these antibodies could bind to formalin fixed paraffin embedded papillary serous ovarian cancer tissue samples. Indirect IHC testing was performed for FRα using a MACH4™ Universal HRP-Polymer Detection Kit (Biocare Medical). Formalin-fixed paraffin-embedded specimens were sectioned at 5 microns on positively-charged glass slides and heated for approximately 60 minutes at 60° C. Slides were deparaffinized in 3 sequential baths of xylene for 3 minutes each, transferred to three sequential baths of 100% alcohol for 3 minutes each, followed by three sequential baths of 95% alcohol for 3 minutes each and then rinsed for 5 minutes in deionized (DI) water. Prepared samples were then pretreated with Diva heat-induced epitope retrieval solution (Biocare Medical) diluted to 1:10 in DI water and placed inside a pressurized decloaking chamber already filled with 500 ml of DI water. The samples were incubated for 15 minutes inside the decloaking chamber, where pressurized incubation reached a maximum of 125° C. at 16 PSI for 30 seconds and then was cooled for 15 minutes down to 95° C. Slides were then cooled at room temperature for 15 minutes. After cooling, slides were washed in 3 sequential baths of Tris Buffered Saline/0.1% polysorbate 20 (Tween-20®) wash buffer (TBST) for 3 minutes each. All subsequent buffer washes were also performed in this manner. Slides were then blocked in Peroxidase-1 (Biocare Medical) blocking solution for 5 minutes at room temperature, washed with TBST, and then Background Sniper (Biocare Medical) serum-free universal blocking reagent was applied for 10 minutes at room temperature. After the samples were blocked the slides were incubated with 2.5 µg/ml of 26B3 antibody diluted in Antibody Diluent (Dako) or Universal Negative Control—Mouse ready-to-use negative control antibody (Dako, for negative isotype tissue) for 60 minutes at room temperature. Slides were then washed with TBST and incubated with MACH4™ Mouse Probe Primary Antibody Enhancer (provided in the Biocare Medical MACH4™ kit) for 15 minutes at room temperature. Slides were then washed again with TBST and incubated with a Polymer-HRP reagent (provided in the Biocare Medical MACH4™ kit) for 20 minutes at room temperature. Following incubation, slides were washed with TBST and incubated with a 3,3'-diaminobenzidine tetrahydrochloride (DAB) solution (Dako) for 5 minutes at room temperature. Then slides were thoroughly rinsed with DI water 3 times for 30-60 seconds each and counterstained with hematoxylin (Dako) for 2 minutes, washed with TBST, dehydrated in 3 sequential baths each of 95% and 100% alcohol for 30 seconds each, and cleared in 3 sequential baths of xylene for 30 seconds each. Finally, coverslips were applied to the slides prior to analysis.

Figure 4:
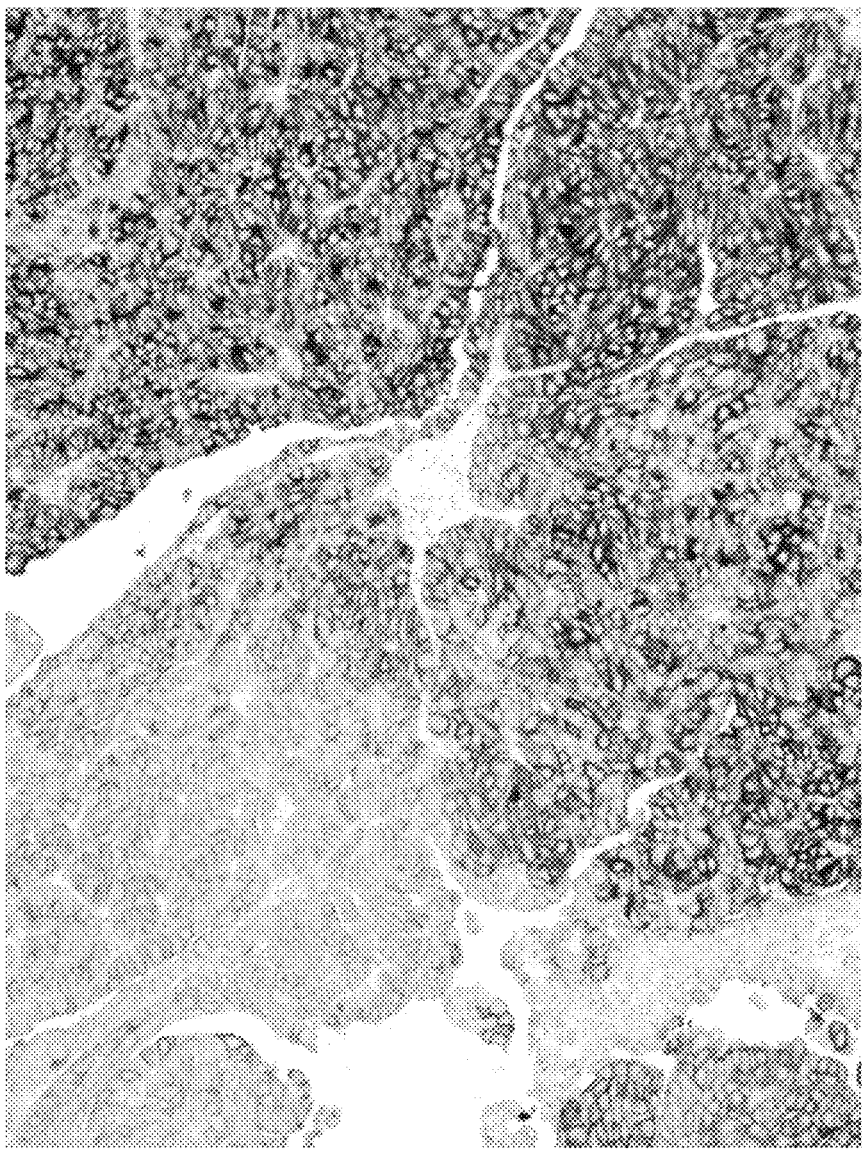
FIG. 4 shows a formalin-fixed, paraffin-embedded papillary serous ovarian cancer tissue sample probed for the presence of FRα with monoclonal antibody 26B3.

It is commonly thought that an antibody must be able to recognize a linear epitope of the antigen of interest to be effective for immunohistochemistry of formalin fixed paraffin embedded tissue because the antigen is devoid of tertiary structure due to the destructive nature of fixation of tissue. Thus it was surprising that antibody 26B3 was able to recognize FRα in this assay (FIG. 4), since it does not recognize reduced and denatured FRα by western blot. Furthermore, the pattern of FRα staining with antibody 26B3 observed for normal tissues was consistent with previously published literature using a variety of other antibodies and techniques, with pancreas, thyroid, lung, salivary gland, kidney, hypophysis, cervix and breast showing expression to various degrees (Table 3). As shown in FIG. 5, the staining pattern in normal tissues, exemplified in normal lung (A) and normal kidney (B) sections, is highly restricted to epithelial cells and typically apical in nature.

TABLE 3

FRα expression in normal human tissues

| Tissue Type | Staining (Number/Intensity) | Comments |
|---|---|---|
| Cerebrum | 0/3 | |
| Cerebellum | 0/3 | |
| Adrenal | 0/3 | |
| Ovary | 0/3 | |
| Pancreas | 3/3; 2+ | Limited to luminal borders of ductal and acinar cells |

TABLE 3-continued

FRα expression in normal human tissues

| Tissue Type | Staining (Number/Intensity) | Comments |
|---|---|---|
| Thyroid | 2/5; 1+ (sparse) | Cytoplasmic staining in follicular cells |
| Hypophysis | 3/3; 1+ | Predominantly cytoplasmic |
| Testis | 0/3 | |
| Breast | 3/3; 1+/2+ | Ductal cells with luminal and membrane staining |
| Spleen | 0/3 | |
| Tonsil | 0/3 | |
| Thymus | 0/3 | |
| Bone Marrow | 0/3 | |
| Lung | 3/3; 2+ | Staining in bronchial and alveolar cells |
| Heart | 0/3 | |
| Esophagus | 0/3 | |
| Stomach | 0/2 | |
| Small Intestine | 0/3 | |
| Colon | 0/3 | |
| Liver | 0/3 | |
| Salivary Gland | 3/3; 3+ | Ductal and acinar cells |
| Kidney | 3/3; 3+ | Luminal staining of proximal tubular cells |
| Prostate | 0/3 | |
| Endometrium | 0/3 | |
| Cervix | 1/3; 1+ | Endocervical cells |
| Skeletal Muscle | 0/3 | |
| Skin | 0/3 | |
| Nerve | 0/3 | |
| Mesothelium (pleura and lung) | 3/3; 2+ | Alveolar cells |

Example 8

Recognition of Native Forms of FRα

Flow cytometry studies were conducted to assess the ability of selected FRα-specific antibodies to bind to the native protein. For these studies Chinese hamster ovary (CHO) cells expressing FRα, were harvested, washed, and re-suspended in ice-cold growth media (RPMI supplemented with 10% FBS). Cells were incubated for 1 hour on ice with 9F3, 19D4, 24F12, or 26B3 (1 µg/mL), washed and then incubated with FITC-conjugated secondary antibodies [dilution 1:100] (Southern Biotech, Birmingham, Ala.). Prior to analysis, cells were labeled with 7-amino-actinomycin D (7-AAD) (BD Biosciences, Franklin Lakes, N.J.) for the exclusion of non-viable cells. CHO cells not expressing FRα were also subjected to the same experimental procedures, as a negative control. Cells were analyzed on an EasyCyte™ Flow Cytometer (Guava® Technologies, Hayward, Calif.). The data provided in Table 4 indicate that all four antibodies are capable of binding native FRα.

TABLE 4

FRα-specific antibodies recognize FRα expressed on the cell surface

| | Geometric Mean Observed for Antibody: | | | |
|---|---|---|---|---|
| Target | 9F3 | 26B3 | 24F12 | 19D4 |
| Cells only | 2.7 | 2.7 | 2.7 | 2.0 |
| CHOK1 | 5.9 | 5.7 | 5.9 | — |
| FRα | 759.5 | 853.7 | 777.0 | 1130.5 |
| FRβ | 6.1 | 5.9 | 6.6 | — |
| FRΔ | 5.6 | 5.4 | 5.9 | — |

Example 9

Detection of FRα in the Serum of Subjects Known to have Ovarian Cancer

Electrochemiluminescence studies were conducted to determine whether the FRα-specific antibodies described herein could detect FRα in the serum of patients known to have ovarian cancer. For these experiments MAb 26B3 was used as the capture MAb and added to ECL plates at a concentration of 75 μg/mL. Plates were washed and 50 μL of sample serum was added to each well and incubated for 2 hours. Serum samples were obtained from normal healthy females (negative control) and from ovarian cancer patients. Samples were diluted 1:4 in PBST (phosphate buffered saline, pH7.4, containing 0.01% polysorbate 20 (Tween®-20)). Following incubation, samples were washed with PBST and 25 μL/well of MAb 19D4 (1 μg/mL), labeled with Ru at a ratio of approximately 13 labels/IgG molecule, was added to each well to detect bound sample. After a 2-hour incubation period, the plates were washed with PBST and read with 2×MSD Buffer T. The results in Table 5 show that FRα in serum can be captured and detected using monoclonal antibodies 26B3 and 19D4.

TABLE 5

Relative serum levels of FRα

| Category (n) | Mean FRA pg/mL | Standard Deviation |
|---|---|---|
| Normal (15) | 223 | 74 |
| Ovarian Cancer (15) | 1815 | 3896 |

Example 10

Detection of FRα in the Serum and Urine of Subjects Known to have Ovarian Cancer Electrochemiluminescence studies were then conducted to determine whether the FRα-specific antibodies described herein could detect FRα in the serum and urine of patients known to have ovarian cancer. For these experiments MAb 26B3 was used as the capture MAb and added to ECL plates at a concentration of 75 μg/mL. Plates were washed and 50 μL of sample serum was added to each well and incubated for 2 hours. Matched serum and urine samples were obtained from normal healthy females (negative control) and from ovarian cancer patients. Samples (serum or urine) were diluted 1:4 in PBST (phosphate buffered saline, pH7.4, containing 0.01% polysorbate 20 (Tween®-20)). Following incubation, samples were washed with PBST and 25 μL/well of MAb 19D4 (1 μg/mL), labeled with Ru at a ratio of approximately 13 labels/IgG molecule, was added to each well to detect bound sample. After a 2-hour incubation period, the plates were washed with PBST and read with 2×MSD Buffer T. The results in Table 6 show that FRα in serum and urine can be captured and detected using monoclonal antibodies 26B3 and 19D4.

TABLE 6

Relative serum and urine levels of FRα

| Patient Designation | Serum FRalpha pg/mL | Urine FRalpha pg/mL |
|---|---|---|
| Normal 1 | 398 | 3080 |
| Normal 2 | 236 | 11508 |
| Normal 3 | 315 | 7704 |
| Normal 4 | 320 | 13198 |
| Ovarian Cancer 1 | 19479 | 368066 |
| Ovarian Cancer 2 | 4144 | 23738 |
| Ovarian Cancer 3 | 986 | 165826 |
| Ovarian Cancer 4 | 719 | 414187 |

Example 11

M-Score as a Metric for Immunohistochemistry Results

A metric for staining (M-score) of each sample was developed and can be defined as follows:

$$M_i = \frac{\sum_{j=1}^{3} w_j \cdot x_{ij}}{\sum_{j=1}^{3} w_j} = \frac{\sum_{j=1}^{3} w_j \cdot x_{ij}}{6}$$

In the equation, $x_{ij}$ is the percentage of tumor stained at intensity j for patient i and $w_j$ is the absolute value of the intensity (ranging from 0 to 3+). The metric has a theoretical range from zero (no positive staining) to fifty (100% of cells staining at 3+ intensity). As such, the M-score is a weighted score for FRα IHC tumor cell membrane staining that captures both the proportion of FRα positive cells and staining intensity. M-scores for each patient were averaged over multiple tissue microarray (TMA) samples, where appropriate. If a sample was void of results, i.e. no tumor present or necrotic tissue, the M-score was assigned to the non-void determinations.

A practical application of the above equation is presented below:

| 3+ | 2+ | 1+ | 0 | M Score |
|---|---|---|---|---|
| x = 40 | y = 30 | z = 10 | | M = (3x + 2y + z)/6 |
| 3 × 40 = 120 | 2 × 30 = 60 | 1 × 10 = 10 | | (120 + 60 + 10)/6 = 31.67 |

Here, x = % of tumor stained with intensity 3+; y = % of tumor stained with intensity 2+; z = % of tumor stained with intensity 1+.

The positivity rate for FRα expression within a given histology was calculated as the proportion of samples that were stained positive according to the definition of a positive result (≥5% of the total tumor cells staining). Exact binomial confidence intervals were determined using established methods (Clopper C. J. and Pearson R. C., Biometrika. 26:404-13 (1934)). Summary statistics are presented herein for all demographic variables and for the M-score. Differences for mean values were determined using one-way ANOVA with post-hoc tests controlling for overall type I error. Differences in mean values were statistically different if the p-value associated with the test was less than the Bonferroni adjusted type I error for that test (maximum Type I error=0.05).

Example 12

Comparative Staining of Lung Carcinoma Cells with Antibody 26B3 and Antibody BN3.2

Figure 6:
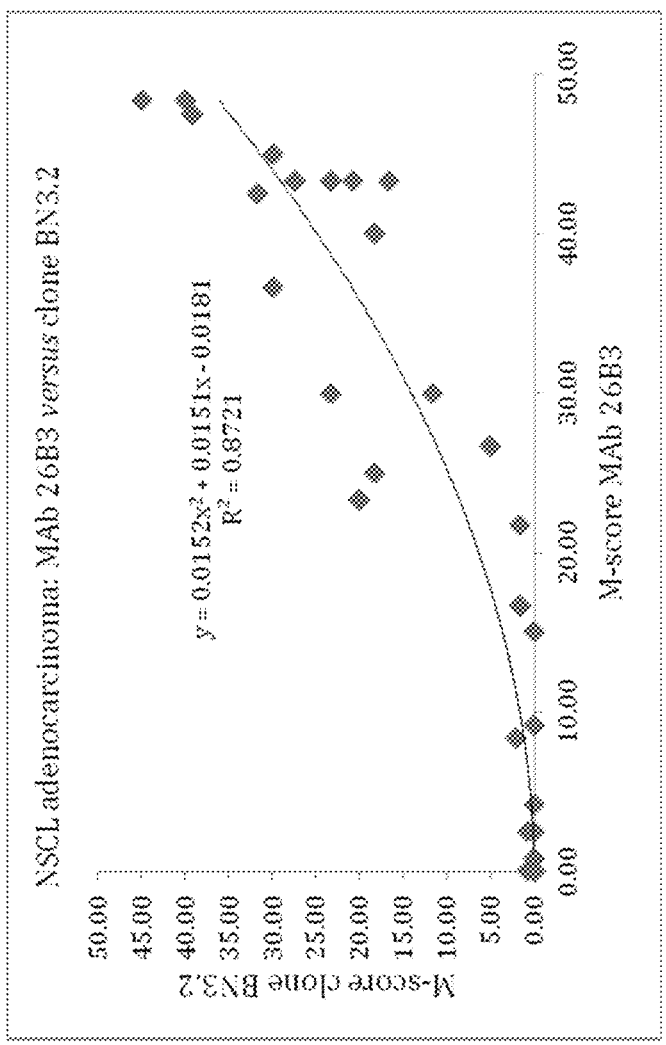
FIG. 6 provides a graphical representation comparing M-scores for lung adenocarcinoma generated using antibody 26B3 or antibody BN3.2.

There is significant variation in the literature with respect to the percent of various carcinomas that express FRα as determined by IHC, in part due to the use of a variety of antibodies, most of which are not commercially available. One FRα specific MAb that is commercially available and has been demonstrated to detect FRα on FFPE sections by IHC is antibody BN3.2 (Leica Microsystems, Buffalo Grove, Ill.). Therefore studies were conducted to compare antibody BN3.2 to antibody 26B3 for both specificity and sensitivity for the detection of FRα using a commercial TMA containing various histological types of lung cancer. Both antibodies were highly specific for adenocarcinoma as compared with other histologic subtypes, particularly squamous cell carcinoma. However, antibody 26B3 was significantly more sensitive than BN3.2, identifying 26/36 (72%; M-score mean±SD=19.84±18.64) and 22/36 (61%; M-score mean±SD=11.38±14.25) adenocarcinoma samples, respectively (p<0.0001). These data demonstrate that antibody BN3.2 is significantly less sensitive than antibody 26B3 for detecting FRα expression on FFPE tissue samples and, as shown in FIG. 6, the relationship in observed M-scores on lung adenocarcinoma samples for these two antibodies is non-linear.

Example 13

Detection of FRα in Subjects Known to have Adenocarcinoma of the Lung

Experiments were conducted to determine whether the presence of FRα positive histology, as detected by antibody 26B3, was associated with particular forms of lung cancer. A tissue microarray having duplicate samples of normal and cancerous, stage I, stage II, stage III, and stage IV, lung tissue specimens was assessed for FRα expression via IHC staining using antibody 26B3, as described in Example 7. As can be seen from the data in Table 6, FRα is associated with adenocarcinomas relative to squamous cell carcinomas, which exhibited limited positive staining.

TABLE 7

Histological evaluation of cancerous tissue samples

| | | | Membrane Positive | | |
|---|---|---|---|---|---|
| | Membrane Staining | | Negative | Positive | Total |
| Histology Groups | Adenocarcinoma | Count % within | 11 | 27 | 38 |
| | | Histology Groups | 28.9% | 71.1% | 100.0% |
| | Squamous | Count % within | 28 | 3 | 31 |
| | | Histology Groups | 90.3% | 9.7% | 100.0% |
| | Other Carcinomas | Count % within | 17 | 4 | 21 |
| | | Histology Groups | 81.0% | 19.0% | 100.0% |
| | Normal | Count % within | 2 | 8 | 10 |
| | | Histology Groups | 20.0% | 80.0% | 100.0% |
| Total | | Count % within | 58 | 42 | 100 |
| | | Histology Groups | 58.0% | 42.0% | 100.0% |

Further analyses were performed on 89 of the histological samples in the tissue microarray where 36 (40%) were adenocarcinoma, 32 (36%) were squamous cell carcinoma, 2 (2%) were adenosquamous carcinomas, and the remaining 19 (21%) represented a variety of histologies (Table 8). The overall rates of FRα positivity varied substantially for each of the histologic subtypes. A significantly higher proportion of adenocarcinoma tumors were positive for FRα when compared to squamous cell carcinomas (72% versus 13%, p<0.0001). Of the 4 positive squamous cell carcinoma samples, only 1 showed 3+ staining on both samples; 1 had intermediate (2+) staining on both samples and the other 2 were very weakly positive in a single sample (5-10% of tumor cells at 1+). Furthermore, the two adenosquamous carcinoma samples were also shown to be positive for FRα, with staining restricted to the adenocarcinoma portion of these samples (FIG. 7).

TABLE 8

Distribution of FRα Expression Across NSCLC Type#

| Variable | FRα negative N (%) | FRα positive N (%) | Total | P value* |
|---|---|---|---|---|
| Tumor Histology | | | | |
| Normal | 1 (10%) | 9 (90%) | 10 | |
| Squamous cell carcinoma | 28 (87%) | 4 (14%) | 32 | <0.0001 |
| Large cell carcinoma | 3 (60%) | 2 (40%) | 5 | |
| Small cell carcinoma | 7 (87%) | 1 (13%) | 8 | |
| Neuroendocrine carcinoma | 4 (67%) | 2 (33%) | 6 | |
| Adenocarcinoma** | 10 (16%) | 28 (74%) | 38 | |
| Tumor Grade | | | | |
| Grade 1 | 1 (20%) | 4 (80%) | 5 | |
| Grade 2 | 5 (22%) | 18 (78%) | 23 | |
| Grade 3 | 4 (40%) | 6 (60%) | 10 | 0.517 |
| Tumor Stage | | | | |
| Stage I | 4 (29%) | 11 (71%) | 15 | |
| Stage II | 2 (17%) | 10 (83%) | 12 | |
| Stage III + IV*** | 4 (36) | 7 (64) | 11 | 0.563 |
| Gender | | | | |
| Female | 3 (18%) | 14 (82%) | 17 | |
| Male | 7 (33%) | 14 (67%) | 21 | 0.46 |

Figure 8:
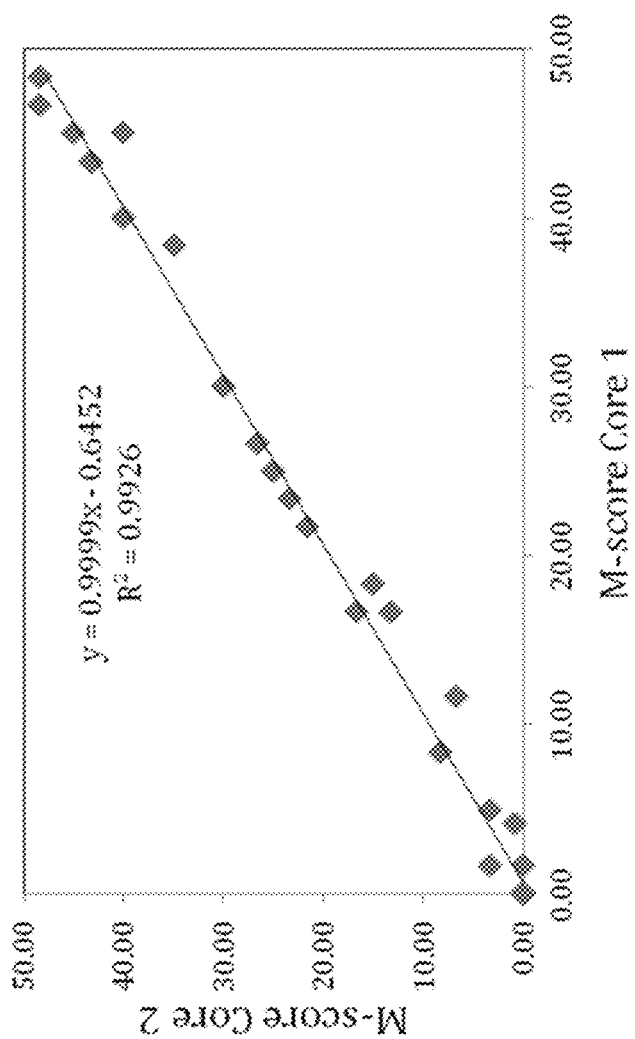
FIG. 8 provides a graphical representation comparing M-scores for lung adenocarcinoma duplicate samples (cores) stained with antibody 26B3.

US Biomax Lung Cancer TMA (catalog # BC041114; 90 cases, duplicate cores)
*P values determined using Fisher's exact test or chi-square test: squamous cell carcinoma versus adenocarcinoma p < 0.0001; males versus female, p = 0.46; stage, p = 0.563; grade, p = 0.517
**Includes 2 adenosquamous cases, both positive for FRα in the adenocarcinoma portion only
***Only 1 stage IV case M-score analyses of duplicate adenocarcinoma histology samples showed little variation in staining by antibody 26B3 (FIG. 8), a reflection of the robustness of antibody 26B3 staining. Also, an examination of M-scores by stage and grade within the adenocarcinoma histologic subtype indicated that neither stage nor grade of disease was associated with the degree of staining as defined by the M-scores (data not shown).

Figure 9:
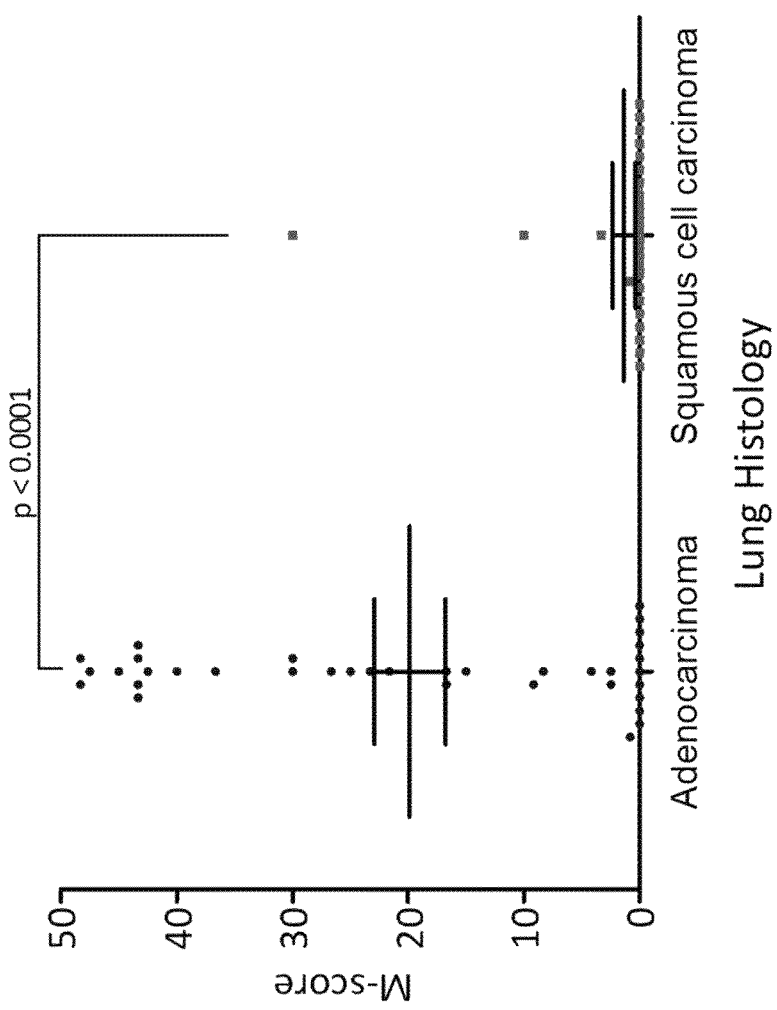
FIG. 9 illustrates the M-score for FRα distribution of lung adenocarcinoma and squamous cell carcinoma. The mean M-Scores were 19.84 (±18.64) and 1.39 (±5.54), respectively ($p<0.0001$).

The M-score distribution for FRα staining of lung adenocarcinoma and squamous cell carcinoma samples is shown in FIG. 9. The mean (±SD) M-scores for adenocarcinoma and squamous cell carcinoma samples stained with antibody 26B3 were 19.84 (±18.64) and 1.39 (±5.54), respectively (p<0.0001). The M-score for adenocarcinoma was also significantly higher when compared against all other lung cancer histologic types. In addition, a Tree Analysis was performed to determine the odds for the histology of the cancer being adenocarcinoma. An M-score >21.7 resulted in an odds ratio (OR) of 16, further demonstrating that FRα is predominately expressed in the adenocarcinoma histology (analysis not shown).

Figure 10:
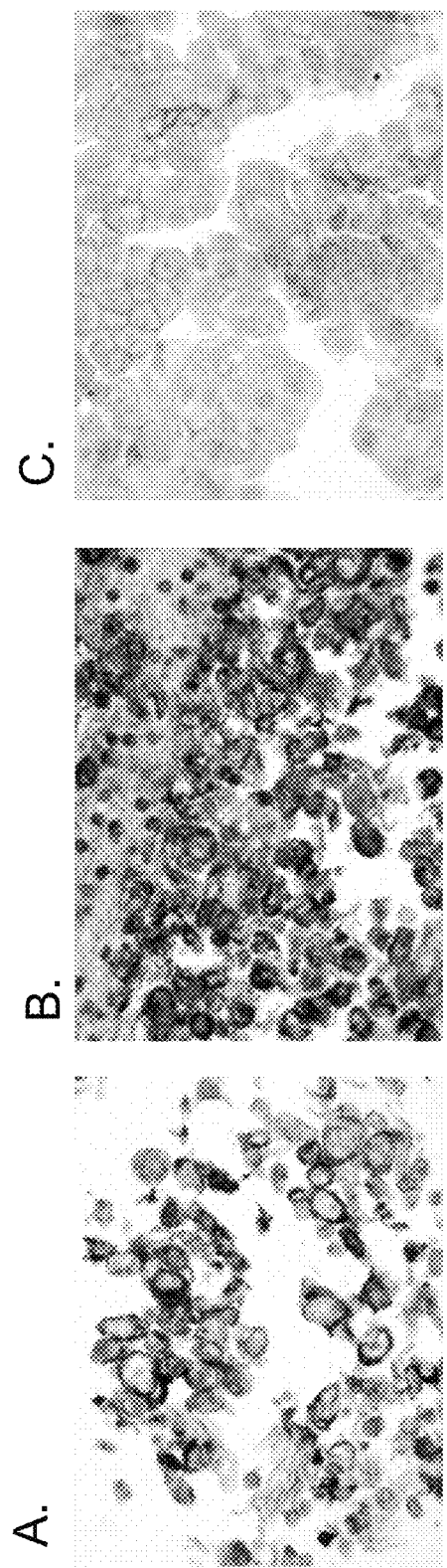
FIG. 10 shows FRα expression in three lung adenocarcinoma fine needle aspiration (FNA) samples (A), (B), and (C). Staining of cell block material from lymph node FNAs with antibody 26B3 demonstrated successful staining of FRα, with expression limited to epithelial cells with an apical distribution.

Formalin-fixed, paraffin-embedded (FFPE) tissue blocks are rarely available from patients diagnosed with late stage lung cancer, as surgical resections are not typically performed. Therefore, studies were performed to determine the suitability of fine needle aspirate (FNA) specimens for FRα IHC using MAb 26B3, as late stage lung cancer is most frequently diagnosed via small biopsy or cytology material. For these studies, samples were obtained from nine late-stage adenocarcinoma patients diagnosed by cytological evaluation of a thoracic lymph node aspirate (FIG. 10) and demonstrated that the rate of FRα positivity (63%) was comparable to that seen for the histological specimens assessed on the lung cancer TMA. Although only a small sample size, these data suggest that cytologic specimens may be a suitable tissue source for determining FRα expression in late stage adenocarcinoma patients.

Example 14

FRα is Expressed by CK+/CD45− Cells, but not CK−/CD45+ Cells, Isolated from the Blood of Patients Known to have Non-Small Cell Lung Carcinoma Studies were conducted to determine the expression profile of FRα on circulating tumor cells (CTCs) of Patients known to have Non-Small Cell Lung Carcinoma. For these studies, blood samples were obtained from 15 healthy donors and 5 stage IV lung cancer patients and then enriched for CTCs via dielectrophoresis field flow fractionation using ApoCell's ApoStream™ system. After enrichment, each sample was stained for cytokeratin (CK), CD45 (protein tyrosine phosphatase receptor type C), nuclei, and FRα. FRα staining was performed using antibody 26B3 as the primary antibody, which was then detected using a mouse-specific, secondary antibody conjugated to DyLight® 649. As shown in Table 9, FRα expression was observed by CK+/CD45− CTCs, but not CK−/CD45+ CTCs.

TABLE 9

Expression of FRα by circulating tumor cells of patients known to have non-small cell lung carcinoma

| Patient ID | CK−/CD45+ count | CK−/CD45+/FRα+ % | FRα MFI (CK−/CD45+) |
|---|---|---|---|
| Patient 1 | 2,270 | 0.0 | NA |
| Patient 2 | 24,452 | 0.0 | NA |
| Patient 3 | 26,503 | 0.0 | NA |
| Patient 4 | 16,540 | 0.0 | NA |
| Patient 5 | 2,652 | 0.0 | NA |

| Patient ID | CK+/CD45− cell count in 7.5 mL of blood | CK+/CD45−/FRα+ % | FRα MFI (CK+/CD45−) |
|---|---|---|---|
| Patient 1 | 55 | 15.6 | 82,195 |
| Patient 2 | 105 | 32.8 | 172,669 |
| Patient 3 | 216 | 9.3 | 146,521 |
| Patient 4 | 57 | 16.7 | 179,027 |
| Patient 5 | 47 | 8.1 | 277,335 |

Example 15

5-Year Survivorship of Subjects with and without FRα-Expressing Adenocarcinoma of the Lung Experiments were conducted to determine whether the presence of FRα positive histology, as detected by antibody 26B3, could be associated with either improved or diminished 5-year survivorship. Normal and cancerous, stage I or stage II adenocarcinoma, lung tissue specimens were subjected to IHC staining, as described in Example 7, and then read. The percentage of 3+, 2+, 1+ and 0 intensity of the stain on the tumor was recorded. There were 177 slides that were interpretable as duplicate or triplicate of a patient. When combined with the evaluable clinical and histological data 53 evaluable cases were identified. The analyses were performed in view of data relating to demographic, clinical and survival status at 5 years past diagnosis of non-small cell adenocarcinoma of the lung.

To determine an optimal cut-point for the M-score a receiver operating characteristic (ROC) analysis was performed. Diagnostic accuracy was of no importance in this analysis; however, the ratio of the diagnostic likelihood ratio of the positive test to the diagnostic likelihood ratio of the negative test was important. These ratios are defined as described in Pepe MS, *The statistical evaluation of medical tests for classification and prediction*, New York: Oxford University Press (2003). At a cut-point of 10 the odds ratio achieved a maximum of 6.62. This value of M was chosen to determine the positivity of a stained slide.

Figure 11:
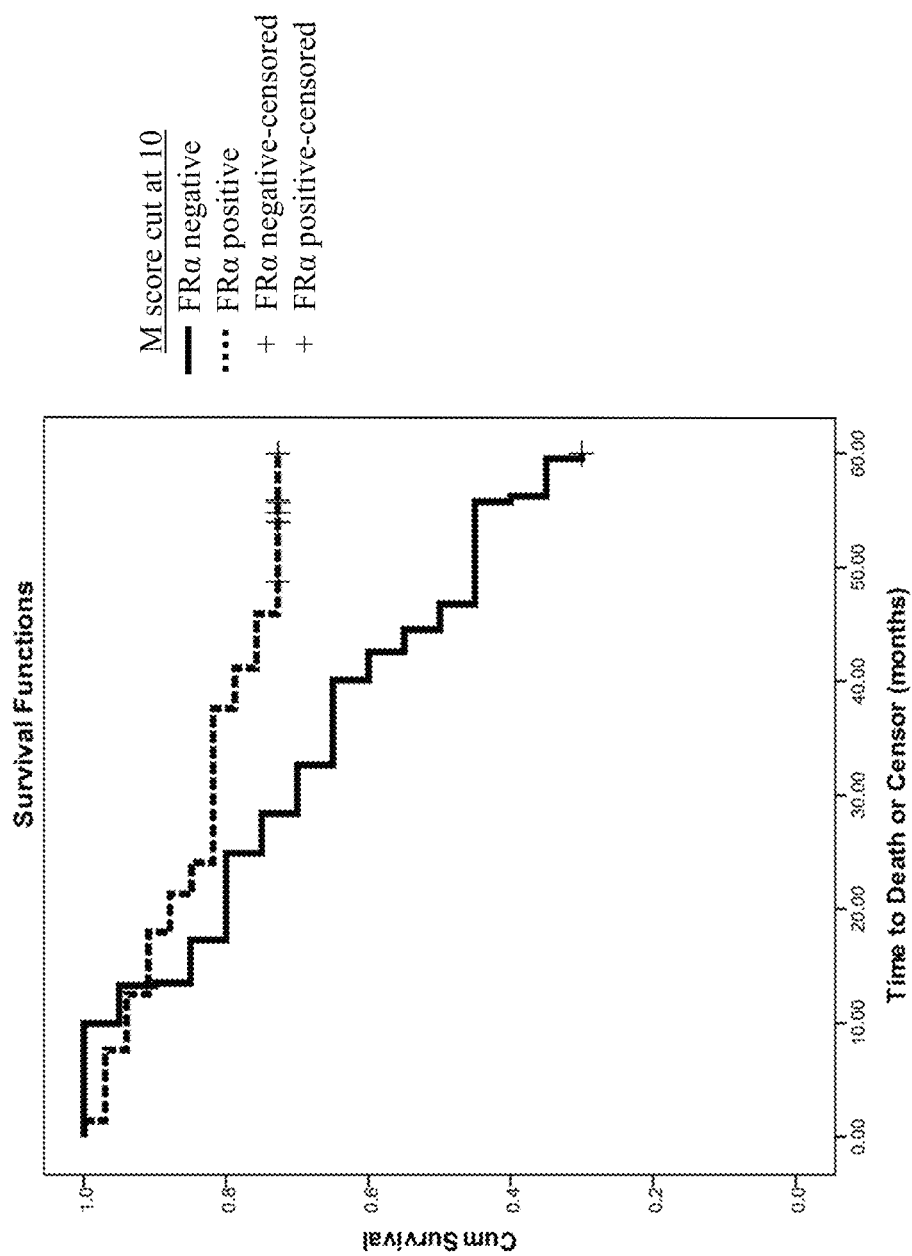
FIG. 11 illustrates the survival functions (death or censor) for subjects having lung adenocarcinoma who were deemed to be FRα positive and FRα negative by immunohistochemistry analysis of tissue samples using antibody 26B3.

Kaplan-Maier survival functions were produced with FRα association as the prognostic factor. A log rank test indicated that being positive for FRα was beneficial for non-fatal events (Chi-sq=7.34, df=1, p=0.007). FIG. 11 illustrates the survival functions for stage I and stage II adenocarcinoma groups deemed to be FRα positive and FRα negative by 26B3 detection. At 5 years the hazard ratio is 2.42. This indicates that subjects having tumors that are negative (M<10) for FRα are 2.5 times more likely to die within five years of diagnosis than subjects with FRα-positive tumors (M≥10).

Example 16

Folate Receptor Alpha Expression is Associated with Triple-Negative Forms of Breast Cancer Studies were conducted to assess the expression of FRα by breast cancer tissue samples. Analyses were conducted using tissue microarray (TMA) samples stained with antibody 26B3 as described in Example 7 and FFPE histology samples prepared and stained with antibody 26B3 as described in Example 7.

Figure 12:
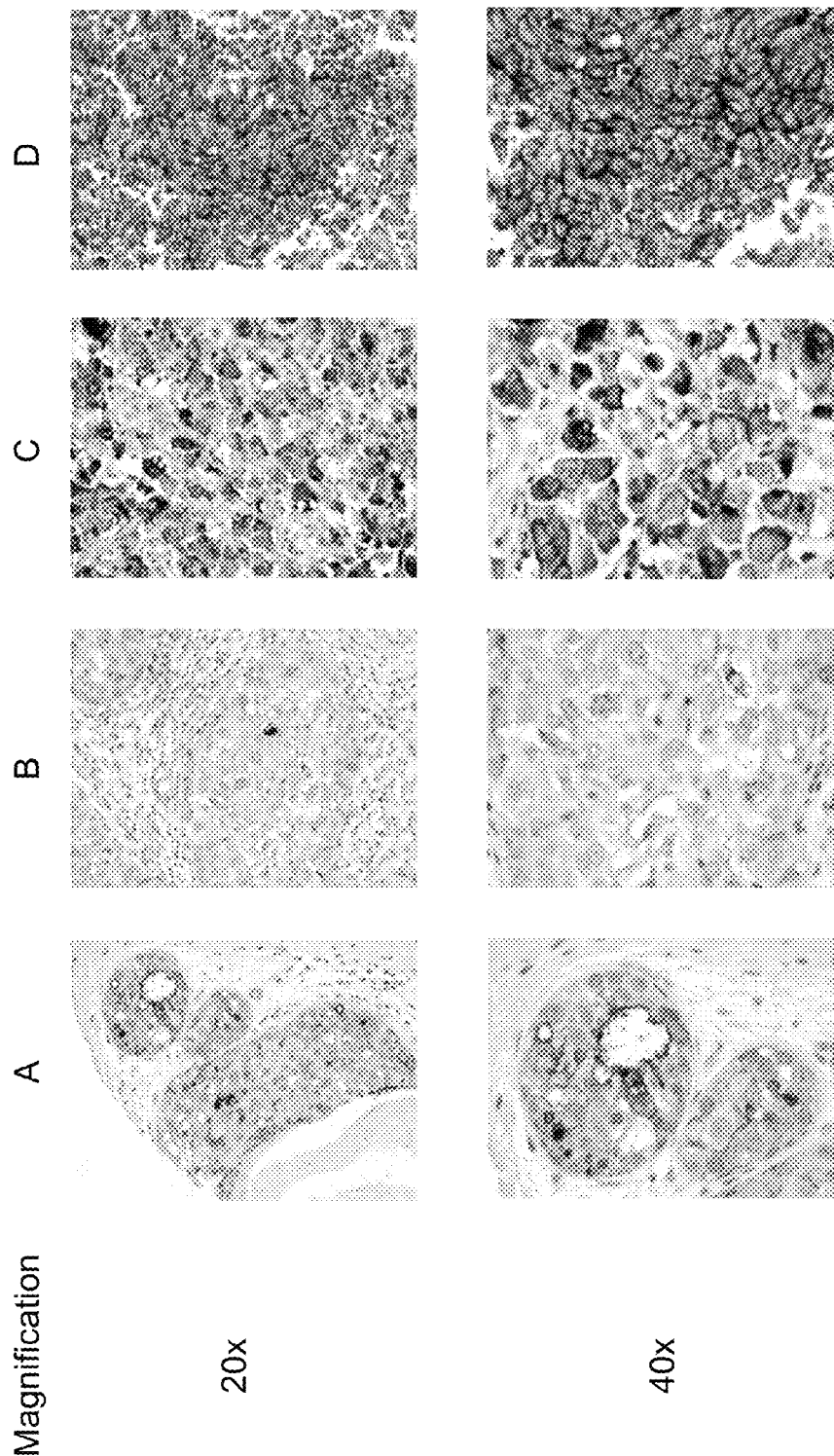
FIG. 12 shows representative tissue microarray (TMA) images stained with antibody 26B3 at either 20× or 40× magnification for (A) ductal carcinoma in situ, (B)-(D) invasive ductal carcinoma.

The distribution of histologies present on the breast cancer TMA (U.S. BioMAX catalog #BR1503a; 72 cases, duplicate cores) are shown in Table 10, the majority of the cases represented being identified as invasive ductal carcinoma (IDC). The TMA included 2 normal breast samples, which were positive for FRα expression as determined by MAb 26B3. Staining in normal breast was restricted to ductal cells with luminal and membrane staining Two of three fibroadenoma cases (67%), 0/2 cystosarcoma cases (0%) and 1/6 ductal carcinoma in situ cases (17%) were positive for FRα. The single invasive lobular carcinoma (ILC) was negative for FRα staining. Of the 59 IDC samples 18 (31%) were positive for FRα (FIG. 12). Given the small number of positive cases on this TMA a valid analysis of FRα expression relative to stage or grade was not possible; however, it should be noted that the majority of samples were either T1 or T2. FRα expression was shown to associate with ER/PR negative tumors relative to ER/PR positive tumors (p=0.012) and with triple negative breast cancers (TNBC) (ER/PR+ or Her2+ versus ER/PR/Her2−, p<0.0001).

Figure 13:
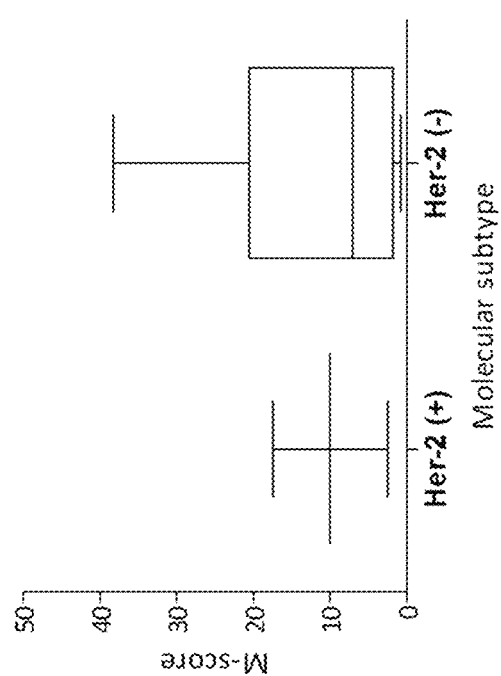
FIG. 13 provides a graphical representation of the M-score distribution, as determined by staining with 26B3, relative to the molecular subtype (her-2 (+) and her-2 (−)) of the breast cancer sample.

Of the 18 FRα positive IDC cases, only 2 (11%) were Her2 positive meaning that the vast majority (89%) were Her2 negative. These data suggest that FRα positivity tracks more closely with Her2 negativity. Further, of the 18 FRα positive IDC cases, 3 were estrogen receptor (ER) positive and 4 were progesterone receptor (PR) positive, but all ER/PR positive/FRα positive cases were Her2 negative. Of the FRα positive IDC cases 12/18 (67%) were triple negative breast cancers (TNBC), suggesting that FRα may be a marker and target for very poor prognosis TNBC molecular subtype. Looking at the TMA as a whole, only 2/13 (15%) of all Her2 positive cases were also positive for FRα while 16/46 (35%) of the Her2 negative cases were also FRα positive, supporting the suggestion that FRα expression correlates negatively with Her2 expression. A representation of the distribution of M-scores for this TMA relative to molecular subtype (her-2 (+) and her-2 (−)) is shown in FIG. 13.

The TMA described above was composed primarily of early stage breast cancers: stage I, 6/60 (10%); stage II, 44/60 (73%); stage III, 10/60 (17%). Therefore, to confirm and extend the results obtained on the TMA, 61 FFPE tissue blocks from stage IV(T4) Her2 negative breast cancers with known ER/PR expression ranging from 0-100% positive were assessed (FFPE tissue blocks were obtained from the archives of Genzyme Genetics). All 61 of these samples were from metastases, not the primary tumor. The results of this study are summarized in Table 11.

Figure 14:
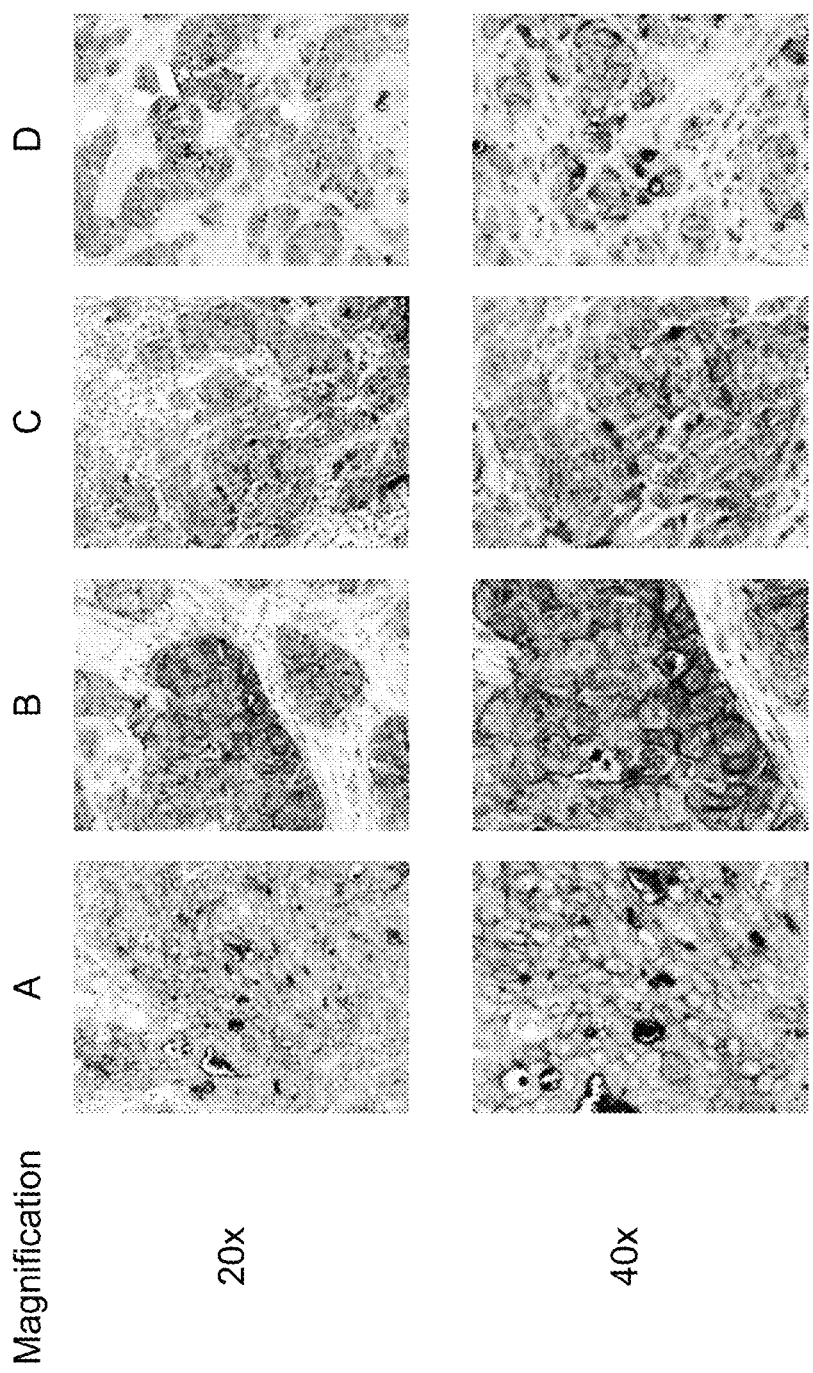
FIGS. 14 (A-D) show representative histology samples from stage IV, her2 negative breast cancers stained with antibody 26B3 at either 20× or 40× magnification.

FRα expression (FIG. 14) was found in 22/61 (36%) of these patients, demonstrating that the percent of FRα positive specimens/tumors determined in early stage disease is retained in late stage metastatic disease in a Her2 negative population (TMA positivity=35%; stage IV metastatic disease=36%). Of the 22 FRα positive stage IV metastatic patients, only 3 (14%) showed any positivity for ER/PR with such positivity trending in the low range (up to 30%). As such, 19/22 (86%) FRα positive patients were of the triple negative molecular subtype. Again, these data compare favorably with the data obtained in early stage disease on the TMA where 67% of all FRα positive patients were of the triple negative subtype.

TABLE 11

Distribution of FRα positivity in molecular subtypes of metastatic breast cancer samples

| Tumor Molecular subtype | FRα positive N (%) | FRα negative N (%) | Total | P value* |
|---|---|---|---|---|
| Total Samples: | 22 (36%) | 39 (64%) | 61 | |
| ER/PR+ | 3 (14%) | 20 (86%) | 23 | |
| ER/PR/Her2− | 19 (50%) | 19 (50%) | 38 | 0.0054 (ER/PR+ versus ER/PR/Her2−) |
| Grade 1 | 3 (30%) | 7 (70%) | 10 | |
| Grade 2 | 11 (28%) | 28 (72%) | 39 | 1.0 (Grade 1 versus Grade 2) |

TABLE 10

Distribution of FRα positivity across histology types - TMA data

| Tumor Histology | FRα positive N (%) | FRα negative N (%) | Total | P value* |
|---|---|---|---|---|
| Normal | 2 (100%) | 0 (0%) | 2 | |
| Fibroadenoma | 2 (67%) | 1 (33%) | 3 | |
| Cystosarcoma | 0 (0%) | 2 (100%) | 2 | |
| DCIS—Ductal carcinoma in situ | 1 (17%) | 5 (83%) | 6 | |
| ILC—Invasive lobular carcinoma | 0 (0%) | 1 (100%) | 1 | |
| IDC—Invasive ductal carcinoma | 18 (31%) | 41 (69%) | 59 | |
| Total carcinomas: | 21 (30%) | 50 (70%) | 71 | |
| IDC Molecular subtype analysis: | | | | |
| ER/PR+ | 4 (14%) | 24 (86%) | 28 | 0.012 |
| ER/PR− | 14 (45%) | 17 (55%) | 31 | |
| Her2+ | 2 (15%) | 11 (85%) | 13 | 0.307 |
| Her2− | 16 (35%) | 30 (65%) | 46 | |
| ER/PR/Her2− | 12 (67%) | 6 (33%) | 18 | <0.0001 (ER/PR+ or Her2+ versus ER/PR/Her2−) |
| T1 | 3 (43%) | 4 (57%) | 7 | |
| T2 | 10 (26%) | 29 (74%) | 39 | |
| T3 | 5 (63%) | 3 (37%) | 8 | |
| T4 | 0 (0%) | 5 (100%) | 5 | |
| N0 | 18 (35%) | 33 (65%) | 51 | 0.092 |
| N1/N2** | 0 (0%) | 8 (100%) | 8 | |
| Grade 1 | 1 (14%) | 6 (86%) | 7 | 0.393 |
| Grade 2 | 12 (36%) | 21 (64%) | 33 | 0.6465 |
| Grade 3 | 5 (26%) | 14 (74%) | 19 | |

*P values calculated via 2X2 contingency table analysis using Fisher's exact test.
**4/8 (50%) of N1/N2 samples were Her2+

TABLE 11-continued

Distribution of FRα positivity in molecular subtypes of metastatic breast cancer samples

| Tumor Molecular subtype | FRα positive N (%) | FRα negative N (%) | Total | P value* |
|---|---|---|---|---|
| Grade 3 | 8 (67%) | 4 (33%) | 12 | 0.037 (Grade 1 or 2 versus Grade 3) |

*P values calculated via 2X2 contingency table analysis using Fisher's exact text.

Figure 15:
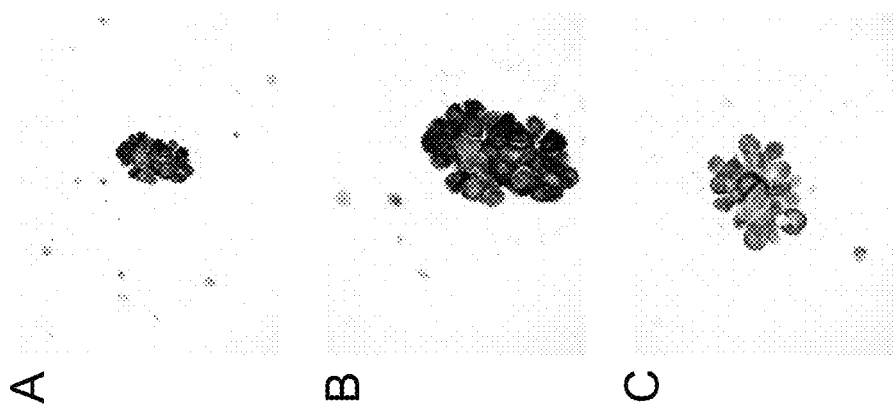
FIGS. 15 (A-C) show representative images of metastatic breast cancer samples obtained by fine needle aspiration stained with antibody 26B3.

Additionally, samples from stage IV metastatic disease were obtained from a number of metastatic sites including lymph node, bone, skin and liver as well as fluid and fine needle aspirate (FNA) samples obtained primarily from pleura and paracentesis. Several of these 'fluid biopsies' stained positive for FRα (FIG. 15) suggesting the general applicability of the described IHC methodology to multiple samples types.

Example 17

Evaluation of Histological Gynecologic Cancer Samples for Expression of Folate Receptor Alpha Immunohistochemical studies were conducted to evaluate FRα expression in gynecologic malignancies involving ovary, endometrium and fallopian tube. Analyses were conducted using tissue microarray (TMA) samples stained with antibody 26B3 as described in Example 7 and FFPE histology samples prepared and stained with antibody 26B3 as described in Example 7. Commercial tissue microarrays were obtained from US Biomax, Inc. (Rockville, Md.) for ovarian carcinomas (catalog #OV1921; 96 cases, duplicate cores); endometrial carcinomas (catalog #EMC1021; 102 cases, single cores); and fallopian tube carcinomas (catalog #UTE601; 30 cases, duplicate cores).

A sample was considered positive for FRα expression if the percentage of the tumor cells positive for membranous staining was greater than or equal to 5% at any intensity. A sample was rejected and therefore not included in the analyses if the gynecologic pathologist determined it was either missing entirely or was composed of necrotic tissue with an insufficient number of viable cells for evaluation. Of the endometrial samples, six contained only atypical complex hyperplasia without adenocarcinoma. Histologic classification of cell type and grade were based the WHO Classification of Breast and Female Genital Organs (Tavassoli and Devilee). Clinical stage based on FIGO and TNM system was provided by the manufacturer of the TMA (US Biomax).

The positivity rate for FRα expression within a given tumor type was calculated as the proportion of tumors that were stained positive according to the definition of a positive result (±5% tumor cell membrane staining). Differences in FRα positivity between groups, e.g. histologies, stage or grade, were assessed using 2×2 contingency tables and Fisher's exact test. Differences in mean values were statistically different if the p-value associated with the test was less than the Bonferroni adjusted type I error for that test (maximum Type I error=0.05).

Figure 16:
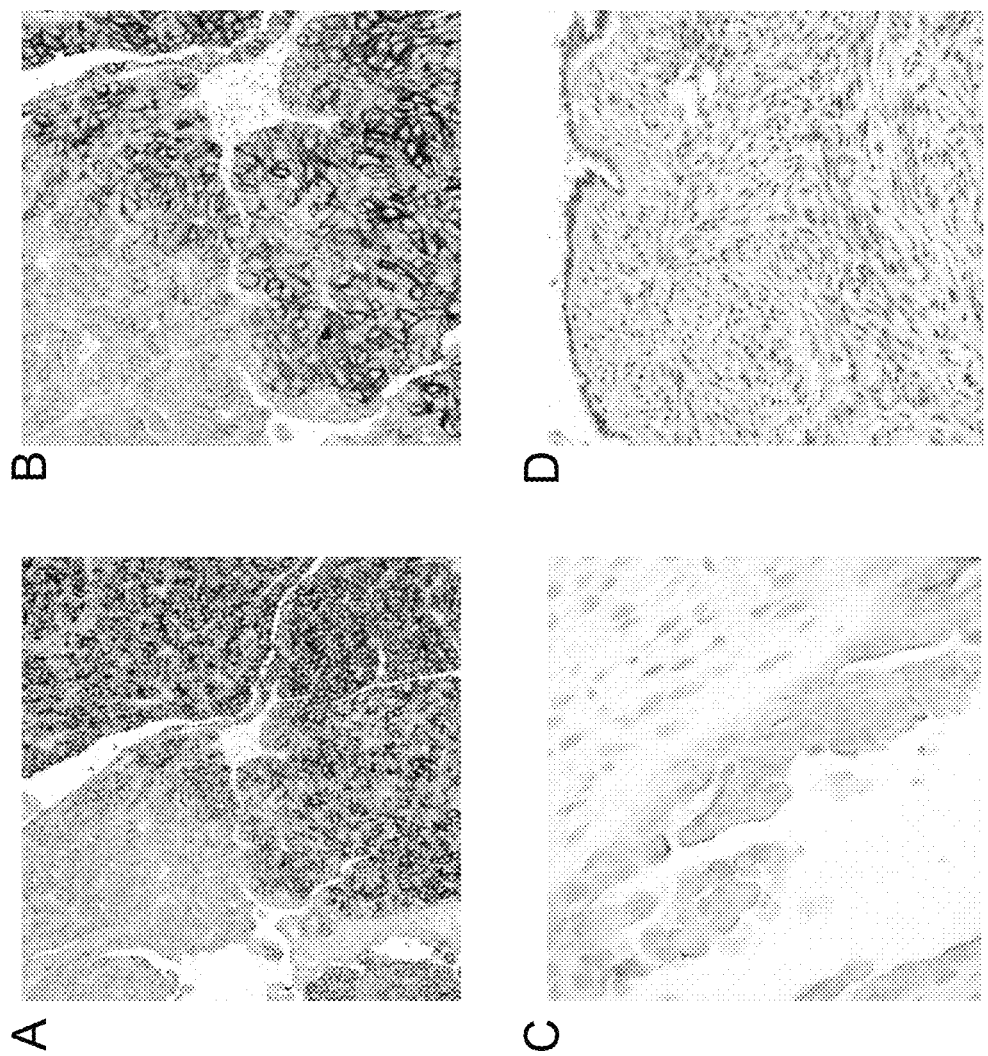
FIG. 16 shows FRα expression in ovarian serous carcinoma. (A) 3+ strong (right field) and 2+ moderate membrane staining (left upper field) are visible at 10× magnification. (B) Shows the same area as (A) at 20× magnification, confirming a 3+ strong, thick circumferential membrane staining (right field). 2+ moderate membrane staining (left upper field) has a weaker, thinner staining than 3+, and it is circumferential or localized to the luminal borders. (C) shows that 1+ weak membrane staining is limited to the luminal borders and requires 40× magnification to visualize. (D) Ovarian surface epithelial cells and the underlying cortical stromal cells are entirely negative (20× magnification).

Membrane and cytoplasmic staining intensity was scored as 0, no staining; 1+, weak; 2+, moderate and 3+, strong. The percent of cells for each intensity in the sample was also determined Tissue was analyzed under 4×, 10×, 20× and 40× objectives. Strong membrane staining (3+) was readily visualized under 4× and confirmed at 10×. Moderate membrane staining (2+) was visible at 10× and confirmed at 20×. Weak staining (1+) required 20× or 40× (FIG. 16). In the presence of 3+ staining, the membrane was thick occurring at apical and lateral cell borders. In tangential sections, a complete circumferential pattern was evident (FIGS. 16 (A) and (B)). 2+ membrane staining was weaker in intensity and thinner than 3+, usually localized on the apical luminal borders and occasionally on lateral cell borders. 1+ weak membrane was generally limited to the luminal borders. The accompanying cytoplasmic staining was variable, depending on the type of tumors.

Of the 94 evaluable samples on the ovarian tumor TMA, 70 (74%) were of the serous type, 10 (11%) were mucinous, 4 (4%) endometrioid, 3 (3%) clear cell type and the remaining 7 (8%) were miscellaneous rare tumors. Of the 87 samples of ovarian carcinomas, the FRα positive rate for each cell type was as follows: 100% (70/70) in serous type, 80% (8/10) mucinous type, 75% (3/4) endometrioid type, and 67% (2/3) clear cell type. The difference between serous and mucinous type is significant with p value at 0.014 by Fisher's exact test (Table 12). FRα status was not significant for histologic grade or clinical stage. Co-existing cytoplasmic staining was usually 2+ or 3+ in serous type and weaker and less frequent in other tumor types.

TABLE 12

Distribution of FRα positivity in relation to histology type, clinical stage and histologic grade in ovarian carcinomas

| Tumor Histology* | FRα negative N (%) | FRα positive N (%) | Total | P value** |
|---|---|---|---|---|
| Serous carcinoma | 0 (0%) | 70 (100%) | 70 | |
| Mucinous carcinoma | 2 (20%) | 8 (80%) | 10 | 0.014 |
| Endometrioid carcinoma | 1 (25%) | 3 (75%) | 4 | |
| Clear cell carcinoma | 1 (33%) | 2 (67%) | 3 | |
| Total | 4 (5%) | 83 (95%) | 87 | |
| Stage II | 4 (9%) | 41 (91%) | 45 | |
| Stage III | 0 (0%) | 29 (100%) | 29 | 0.15 |
| Stage IV | 0 (0%) | 13 (100%) | 13 | |
| Grade 1 | 2 (15%) | 11 (85%) | 13 | NS*** |
| Grade 2 | 1 (3%) | 31 (97%) | 32 | NS |
| Grade 3 | 1 (3%) | 39 (97%) | 40 | NS |

Figure 18:
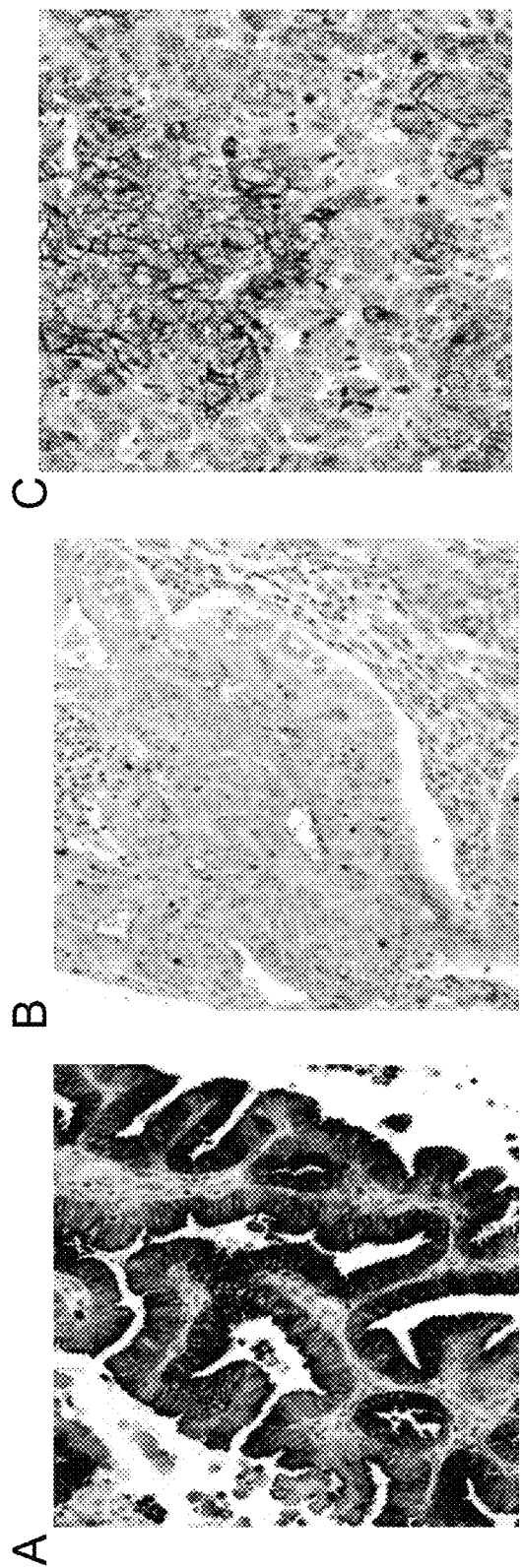
FIG. 18 shows strong (+3) FRα membrane staining on the luminal borders of grade 1 adenocarcinoma of endometrium (A). In addition, many tumor cells have 2+ or 3+ cytoplasmic staining (20× magnification). FRα membrane staining (2+ and 3+) is present on the luminal borders of grade 2 adenocarcinoma of endometrium; cytoplasmic staining is weak (20× magnification (B). About 50% of the tumor cells of grade 3 adenocarcinoma of endometrium demonstrate 3+ strong, circumferential membrane staining with weak cytoplasmic staining at 40× magnification (C).
Figure 19:
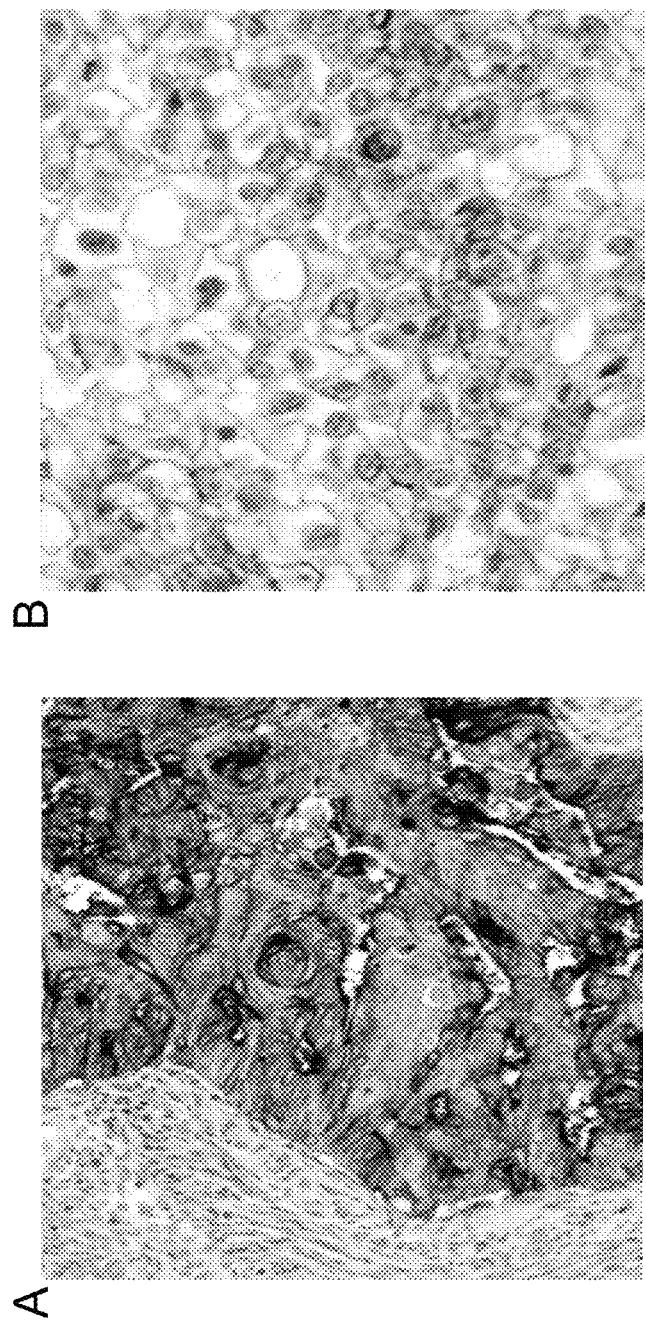
FIG. 19 shows adenocarcinoma with squamous metaplasia with about 80% of metaplastic squamous cells with 2+ and 3+ FRα membrane staining and 1+ and 2+ FRα cytoplasmic staining at 20× magnification (A). Clear cell carcinoma of endometrium tumor cells have large irregular nuclei, prominent nucleoli and abundant clear cytoplasm. The majority of these tumor cells have 2+ or 3+ FRα membrane staining at 40× magnification (B).

*1 transitional cell carcinoma, 1 squamous carcinoma, 1 Embryonal carcinoma, 2 yolk sac tumors and 2 granulosa cell tumors not included in analysis
**P values determined using Fisher's exact test or chi-square test: serous carcinoma versus mucinous carcinoma p = 0.014
***NS = Not Significant In the endometrial samples, FRα was expressed in 80% (4/5) of normal (FIG. 17(A)), 100% (6/6) of atypical complex hyperplasia (FIG. 17(B)), and 89% (80/90) of adenocarcinomas, including 88 endometrioid type and 1 clear cell type (FIGS. 18 and 19). Eight endometrioid adenocarcinomas contained areas of squamous metaplasia. In the normal endometrium, membrane staining was weak and limited to the apical luminal borders (FIG. 17(A)). In atypical complex hyperplasia and carcinomas, staining was predominantly luminal with additional staining on lateral cell borders in some cases (FIG. 17(B)). In the presence of 3+ membrane staining, cytoplasmic staining varied in intensity from strong (FIG. 18(A)) to weak (FIGS. 18(B) and (C)). Tumor cells with 1+ or 2+ membrane staining rarely expressed cytoplasmic staining. The majority of metaplastic squamous cells and clear cells exhibited moderate to strong membrane staining (FIGS. 19(A) and (B)).

FRα expression was positive in 100% of grade 1, 96% of grade 2 and 74% of grade 3 tumors (grade 1 vs. grade 3, p value=0.0029; grade 2 vs. grade 3, p=0.034). FRα status was not significant in relation to T1 vs. T2/3; N0 vs. N1, and stage I vs. stage II/III.

Figure 20:
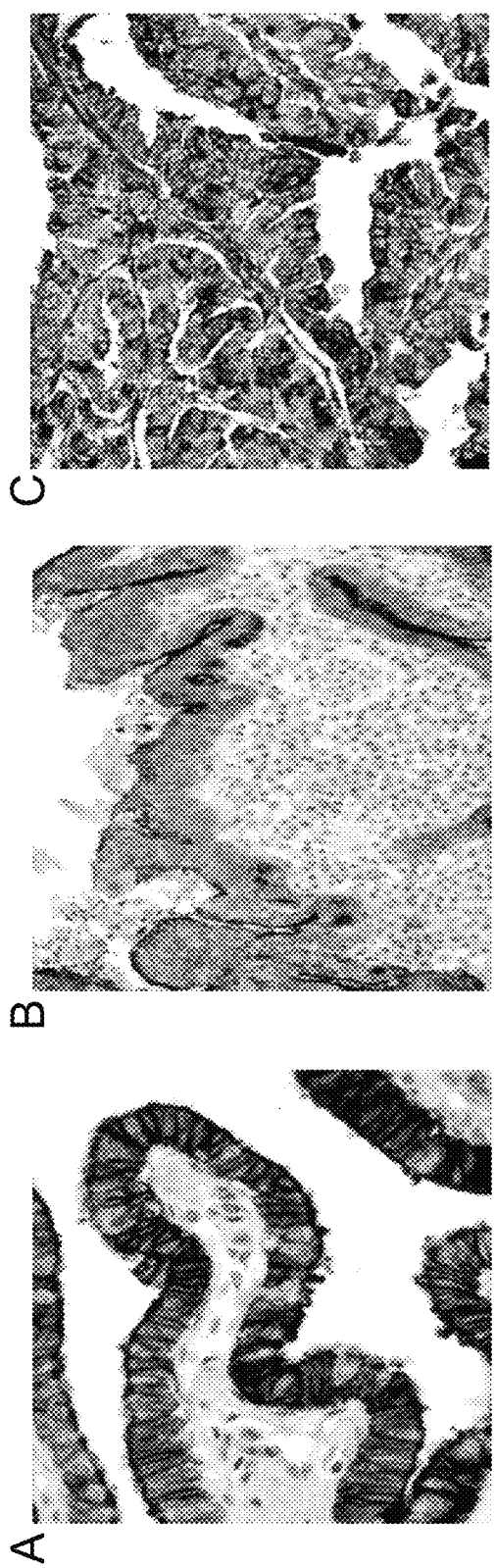
FIG. 20 shows that ciliated and non-ciliated cells of normal fallopian tube have 3+ FRα membrane staining on the luminal and lateral cell borders (A). Cytoplasmic staining is also evident (20× magnification). (B) Chronic salpingitis with abundant lymphocytes and plasma cells in the stroma. Mucosal cells retain 3+ FRα staining on the luminal borders (20× magnification). (C) Grade 2 tubal serous adenocarcinoma tumor cells form complex papillary projections and show 3+ FRα membrane staining on the luminal and lateral cell borders, with cytoplasmic staining also evident (20× magnification).
Figure 21:
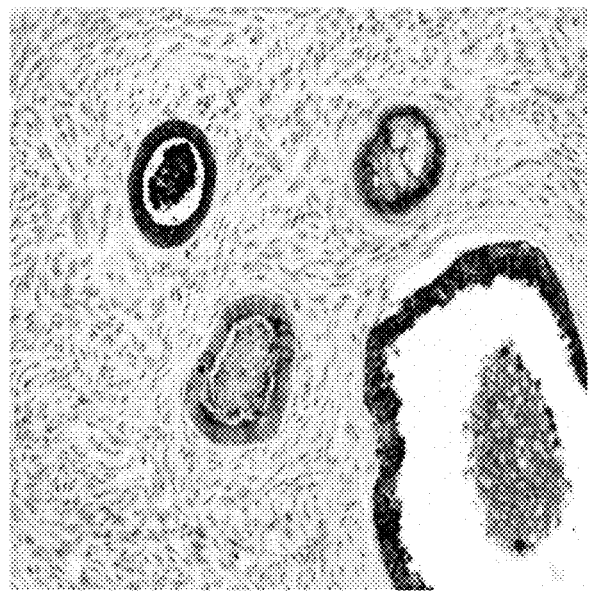
FIG. 21 depicts ovarian cortical serous/tubal cysts. Lining cells reveal 3+, strong membrane and cytoplasmic staining (20× magnification).

Seventeen cores of normal fallopian tubes, 16 samples of chronic salpingitis and 20 tubal serous carcinomas were all strongly positive for membrane and cytoplasmic staining (FIGS. 20 (A) to (C)).

Example 18

Evaluation of Histological Colorectal Samples for Expression of Folate Receptor Alpha Immunohistochemical studies were conducted to evaluate FRα expression in colorectal tissue samples. Analyses were conducted using tissue microarray (TMA) samples obtained from US Biomax (catalog #BC051111). The TMA contained 90 duplicate samples of tissues obtained from subjects known to have colorectal cancer and 10 normal colorectal samples. The samples were stained with antibody 26B3 as described in Example 7. Of the 90 samples obtained from subjects known to have colorectal cancer, 18 (20%) were positive for FRα expression, while none of the normal samples were positive. In addition, positive stating was generally medium to weak and no apparent relationship to stage of disease was discernible.

Example 19

Evaluation of Histological Thryoid Samples for Expression of Folate Receptor Alpha Immunohistochemical studies were conducted to evaluate FRα expression in thyroid tissue samples. Analyses were conducted using tissue microarray (TMA) samples obtained from US Biomax (catalog #TH802a). The samples were stained with antibody 26B3 as described in Example 7. Thyroid papillary carcinoma was strongly positive for FRα membrane expression (26/28, 93%) and was distinguishable from medullary carcinoma, where all 5 samples were negative for FRα staining, in agreement with previous reports. Interestingly, follicular adenomas were separable into macrofollicular type and microfollicular type with 3/13 (23%) and 18/22 (82%) showing positivity for FRα expression, respectively. Some positivity was also seen in the small number of Hurthle cell tumors (2/3, 67%) and follicular carcinoma (3/7, 43%) samples on this TMA. These results are summarized in Table 13.

TABLE 13

| Expression of FRα in thyroid tissue samples | | |
|---|---|---|
| Thyroid Cancer Hisotologic Subtype (N = 78) | FRα positive N (%) | FRα negative N (%) |
| Papillary carcinoma, 28 (36%) | 26 (93%) | 2 (7%) |
| Medullary carcinoma, 5 (6%) | 0 (0%) | 5 (100%) |
| Follicular Adenoma, macrofollicular type, 13 (17%) | 3 (23%) | 10 (77%) |
| Follicular Adenoma, microfollicular type, 22 (28%) | 18 (82%) | 4 (18%) |
| Hurthle cell tumor, 3 (4%) | 2 (67%) | 1 (33%) |
| Follicular carcinoma, 7 (9%) | 3 (43%) | 4 (57%) |

What is claimed:

1. An isolated polynucleotide encoding an antibody, or antigen-binding fragment thereof, specific for folate receptor alpha (FRα), said antibody or antigen-binding fragment comprising:
   a) a light chain CDR1 having the amino acid sequence of SEQ ID NO: 2, a light chain CDR2 having the amino acid sequence of SEQ ID NO: 3, a light chain CDR3 having the amino acid sequence of SEQ ID NO: 4, a heavy chain CDR1 having the amino acid sequence of SEQ ID NO: 6, a heavy chain CDR2 having the amino acid sequence of SEQ ID NO: 7, and a heavy chain CDR3 having the amino acid sequence of SEQ ID NO: 8;
   b) a light chain CDR1 having the amino acid sequence of SEQ ID NO: 10, a light chain CDR2 having the amino acid sequence of SEQ ID NO: 11, a light chain CDR3 having the amino acid sequence of SEQ ID NO: 12, a heavy chain CDR1 having the amino acid sequence of SEQ ID NO: 14, a heavy chain CDR2 having the amino acid sequence of SEQ ID NO: 15, and a heavy chain CDR3 having the amino acid sequence of SEQ ID NO: 16;
   c) a light chain CDR1 having the amino acid sequence of SEQ ID NO: 18, a light chain CDR2 having the amino acid sequence of SEQ ID NO: 19, a light chain CDR3 having the amino acid sequence of SEQ ID NO: 20, a heavy chain CDR1 having the amino acid sequence of SEQ ID NO: 22, a heavy chain CDR2 having the amino acid sequence of SEQ ID NO: 23, and a heavy chain CDR3 having the amino acid sequence of SEQ ID NO: 24; or
   d) a light chain CDR1 having the amino acid sequence of SEQ ID NO: 26, a light chain CDR2 having the amino acid sequence of SEQ ID NO: 27, a light chain CDR3 having the amino acid sequence of SEQ ID NO: 28, a heavy chain CDR1 having the amino acid sequence of SEQ ID NO: 30, a heavy chain CDR2 having the amino acid sequence of SEQ ID NO: 31, and a heavy chain CDR3 having the amino acid sequence of SEQ ID NO: 32.

2. A vector comprising the isolated polynucleotide of claim 1.

3. A cell comprising the isolated polynucleotide of claim 1.

4. The isolated polynucleotide of claim 1, wherein said polynucleotide encodes an antibody, or antigen-binding fragment thereof, specific for folate receptor alpha (FRα), said antibody or antigen-binding fragment comprising a light chain CDR1 having the amino acid sequence of SEQ ID NO: 26, a light chain CDR2 having the amino acid sequence of SEQ ID NO: 27, a light chain CDR3 having the amino acid sequence of SEQ ID NO: 28, a heavy chain CDR1 having the amino acid sequence of SEQ ID NO: 30, a heavy chain CDR2 having the amino acid sequence of SEQ ID NO: 31, and a heavy chain CDR3 having the amino acid sequence of SEQ ID NO: 32.

5. A vector comprising the isolated polynucleotide of claim 4.

6. A cell comprising the isolated polynucleotide of claim 4.

7. A cell that produces an antibody, or antigen-binding fragment thereof, specific for folate receptor alpha (FRα), said antibody or antigen-binding fragment comprising:
   a) a light chain CDR1 having the amino acid sequence of SEQ ID NO: 2, a light chain CDR2 having the amino acid sequence of SEQ ID NO: 3, a light chain CDR3 having the amino acid sequence of SEQ ID NO: 4, a heavy chain CDR1 having the amino acid sequence of SEQ ID NO: 6, a heavy chain CDR2 having the amino acid sequence of SEQ ID NO: 7, and a heavy chain CDR3 having the amino acid sequence of SEQ ID NO: 8;
   b) a light chain CDR1 having the amino acid sequence of SEQ ID NO: 10, a light chain CDR2 having the amino acid sequence of SEQ ID NO: 11, a light chain CDR3 having the amino acid sequence of SEQ ID NO: 12, a heavy chain CDR1 having the amino acid sequence of SEQ ID NO: 14, a heavy chain CDR2 having the amino acid sequence of SEQ ID NO: 15, and a heavy chain CDR3 having the amino acid sequence of SEQ ID NO: 16;

c) a light chain CDR1 having the amino acid sequence of SEQ ID NO: 18, a light chain CDR2 having the amino acid sequence of SEQ ID NO: 19, a light chain CDR3 having the amino acid sequence of SEQ ID NO: 20, a heavy chain CDR1 having the amino acid sequence of SEQ ID NO: 22, a heavy chain CDR2 having the amino acid sequence of SEQ ID NO: 23, and a heavy chain CDR3 having the amino acid sequence of SEQ ID NO: 24; or d) a light chain CDR1 having the amino acid sequence of SEQ ID NO: 26, a light chain CDR2 having the amino acid sequence of SEQ ID NO: 27, a light chain CDR3 having the amino acid sequence of SEQ ID NO: 28, a heavy chain CDR1 having the amino acid sequence of SEQ ID NO: 30, a heavy chain CDR2 having the amino acid sequence of SEQ ID NO: 31, and a heavy chain CDR3 having the amino acid sequence of SEQ ID NO: 32.

8. The cell of claim 7, wherein said cell is a hybridoma.

9. A recombinant polynucleotide encoding an antibody, or antigen-binding fragment thereof, specific for folate receptor alpha (FRα), said antibody or antigen-binding fragment comprising:

a) a light chain CDR1 having the amino acid sequence of SEQ ID NO: 2, a light chain CDR2 having the amino acid sequence of SEQ ID NO: 3, a light chain CDR3 having the amino acid sequence of SEQ ID NO: 4, a heavy chain CDR1 having the amino acid sequence of SEQ ID NO: 6, a heavy chain CDR2 having the amino acid sequence of SEQ ID NO: 7, and a heavy chain CDR3 having the amino acid sequence of SEQ ID NO: 8;

b) a light chain CDR1 having the amino acid sequence of SEQ ID NO: 10, a light chain CDR2 having the amino acid sequence of SEQ ID NO: 11, a light chain CDR3 having the amino acid sequence of SEQ ID NO: 12, a heavy chain CDR1 having the amino acid sequence of SEQ ID NO: 14, a heavy chain CDR2 having the amino acid sequence of SEQ ID NO: 15, and a heavy chain CDR3 having the amino acid sequence of SEQ ID NO: 16;

c) a light chain CDR1 having the amino acid sequence of SEQ ID NO: 18, a light chain CDR2 having the amino acid sequence of SEQ ID NO: 19, a light chain CDR3 having the amino acid sequence of SEQ ID NO: 20, a heavy chain CDR1 having the amino acid sequence of SEQ ID NO: 22, a heavy chain CDR2 having the amino acid sequence of SEQ ID NO: 23, and a heavy chain CDR3 having the amino acid sequence of SEQ ID NO: 24; or d) a light chain CDR1 having the amino acid sequence of SEQ ID NO: 26, a light chain CDR2 having the amino acid sequence of SEQ ID NO: 27, a light chain CDR3 having the amino acid sequence of SEQ ID NO: 28, a heavy chain CDR1 having the amino acid sequence of SEQ ID NO: 30, a heavy chain CDR2 having the amino acid sequence of SEQ ID NO: 31, and a heavy chain CDR3 having the amino acid sequence of SEQ ID NO: 32.

10. A cell comprising the recombinant polynucleotide of claim 9.

11. The recombinant polynucleotide of claim 9, wherein said polynucleotide encodes an antibody, or antigen-binding fragment thereof, specific for folate receptor alpha (FRα), said antibody or antigen-binding fragment comprising a light chain CDR1 having the amino acid sequence of SEQ ID NO: 26, a light chain CDR2 having the amino acid sequence of SEQ ID NO: 27, a light chain CDR3 having the amino acid sequence of SEQ ID NO: 28, a heavy chain CDR1 having the amino acid sequence of SEQ ID NO: 30, a heavy chain CDR2 having the amino acid sequence of SEQ ID NO: 31, and a heavy chain CDR3 having the amino acid sequence of SEQ ID NO: 32.

12. A vector comprising the recombinant polynucleotide of claim 11.

13. A cell comprising the recombinant polynucleotide of claim 11.

* * * * *